United States Patent
Mehra et al.

(10) Patent No.: US 12,370,204 B2
(45) Date of Patent: Jul. 29, 2025

(54) TREHALOSE FORMULATIONS AND USES THEREOF

(71) Applicant: Seelos Therapeutics, Inc., New York, NY (US)

(72) Inventors: Raj Mehra, New York, NY (US); Warren Wasiewski, New York, NY (US); Gopal Krishna, New York, NY (US)

(73) Assignee: Seelos Therapeutics, Inc., New York, NY (US)

( * ) Notice: Subject to any disclaimer, the term of this patent is extended or adjusted under 35 U.S.C. 154(b) by 783 days.

(21) Appl. No.: 17/765,059

(22) PCT Filed: Sep. 29, 2020

(86) PCT No.: PCT/US2020/053226
§ 371 (c)(1),
(2) Date: Mar. 30, 2022

(87) PCT Pub. No.: WO2021/067243
PCT Pub. Date: Apr. 8, 2021

(65) Prior Publication Data
US 2022/0387463 A1    Dec. 8, 2022

Related U.S. Application Data

(60) Provisional application No. 62/908,784, filed on Oct. 1, 2019.

(51) Int. Cl.
*A61K 9/00* (2006.01)
*A61K 31/7016* (2006.01)
*A61P 3/00* (2006.01)

(52) U.S. Cl.
CPC ............ *A61K 31/7016* (2013.01); *A61P 3/00* (2018.01)

(58) Field of Classification Search
None
See application file for complete search history.

(56) References Cited

U.S. PATENT DOCUMENTS

| | | |
|---|---|---|
| 6,440,446 B1 | 8/2002 | Yoshizane |
| 6,555,526 B2 | 4/2003 | Matsuo |
| 6,602,865 B1 | 8/2003 | Andrasi |
| 7,214,667 B2 | 5/2007 | Fukuda |
| 7,732,425 B2 | 6/2010 | Matsuo |
| 7,854,922 B2 | 12/2010 | Tanabe |
| 7,956,181 B2 | 6/2011 | Ehara |
| 8,163,713 B2 | 4/2012 | Nishizawa |
| 8,283,337 B2 | 10/2012 | Sasaki |
| 8,741,871 B2 | 6/2014 | Nishizawa |
| 8,889,651 B2 | 11/2014 | Liu |
| 9,084,720 B2 | 7/2015 | Megiddo |
| 9,125,924 B2 | 9/2015 | Megiddo |
| 9,155,751 B2 | 10/2015 | Suzuki |
| 9,186,356 B2 | 11/2015 | Shen |
| 9,572,825 B2 * | 2/2017 | Megiddo ............... A61K 9/0019 |
| 10,751,353 B2 | 8/2020 | Megiddo |
| 10,869,831 B2 | 12/2020 | Megiddo |
| 11,083,741 B2 * | 8/2021 | Sardiello ............ A61K 31/4375 |
| 2005/0215562 A1 | 9/2005 | Tremblay |
| 2009/0110671 A1 | 4/2009 | Miyata |
| 2009/0110746 A1 | 4/2009 | Gainer |
| 2009/0304664 A1 | 12/2009 | Lindquist et al. |
| 2010/0035837 A1 | 2/2010 | Sasaki |
| 2010/0093993 A1 | 4/2010 | Nishizawa |
| 2011/0224423 A1 | 9/2011 | Chung |
| 2011/0300074 A1 | 12/2011 | Clunas et al. |
| 2012/0121580 A1 | 5/2012 | Bhambhani et al. |
| 2013/0005681 A1 | 1/2013 | Su et al. |
| 2013/0310467 A1 | 11/2013 | Morkiaku |
| 2013/0316971 A1 | 11/2013 | Yang |
| 2014/0066439 A1 | 3/2014 | Gunst |
| 2014/0336145 A1 | 11/2014 | Megiddo |
| 2015/0025028 A1 | 1/2015 | Lee-Chen |
| 2015/0025035 A1 | 1/2015 | Chung |
| 2015/0118196 A1 | 4/2015 | Wada |
| 2015/0196575 A1 | 7/2015 | Megiddo |
| 2016/0022716 A1 | 1/2016 | Megiddo |
| 2016/0101122 A1 | 4/2016 | Megiddo |
| 2016/0120798 A1 | 5/2016 | Megiddo |
| 2016/0303150 A1 | 10/2016 | Megiddo |
| 2017/0020905 A1 | 1/2017 | Megiddo |
| 2017/0304339 A1 | 10/2017 | Sardiello |
| 2019/0336518 A1 | 11/2019 | Megiddo |
| 2019/0374463 A1 | 12/2019 | Megiddo |
| 2021/0008089 A1 | 1/2021 | Megiddo |

(Continued)

FOREIGN PATENT DOCUMENTS

| | | |
|---|---|---|
| EP | 1354590 | 10/2003 |
| JP | 2001302517 | 10/2001 |
| JP | 2003267874 | 9/2003 |

(Continued)

OTHER PUBLICATIONS

Extended European Search Report in European Appln. No. 22216238.0, dated Sep. 18, 2023, 19 pages.
Beckman et al., "A novel tau-based rhesus monkey model of Alzheimer's pathogenesis," Alzheimers Dementia, Feb. 2021, 17(6): 13 pages.
Fernandez-Estevez et al., "Trehalose Reverses Cell Malfunction in Fibroblasts from Normal and Huntington's Disease Patients Caused by Proteosome Inhibition," PLOS One, Jan. 2014, 9(2):e90202, 9 pages.
International Search Report and Written Opinion in for the International Application No. PCT/US2023/081629, mailed on Mar. 4, 2024, 14 pages.

(Continued)

*Primary Examiner* — Dale R Miller
(74) *Attorney, Agent, or Firm* — Fish & Richardson P.C.

(57) ABSTRACT

The present disclosure relates to methods of treating or alleviating one or more symptoms of mucopolysaccharidoses in a subject, via administering a trehalose formulation to the subject.

20 Claims, 1 Drawing Sheet

(56) References Cited

U.S. PATENT DOCUMENTS

| | | | |
|---|---|---|---|
| 2022/0117883 | A1 | 4/2022 | Megiddo |
| 2022/0288096 | A1 | 9/2022 | Megiddo |

FOREIGN PATENT DOCUMENTS

| | | |
|---|---|---|
| JP | 3455633 | 10/2003 |
| JP | 2006342108 | 12/2006 |
| JP | 2007510758 | 4/2007 |
| JP | 4033510 | 1/2008 |
| JP | 2008545628 | 12/2008 |
| JP | 4255101 | 4/2009 |
| JP | 2009517086 | 4/2009 |
| JP | 4950521 | 6/2012 |
| JP | 2012524035 | 10/2012 |
| JP | 5106109 | 12/2012 |
| JP | 2013006773 | 1/2013 |
| JP | 2014139160 | 7/2014 |
| JP | 2014227404 | 12/2014 |
| WO | WO 1997024129 | 7/1997 |
| WO | WO 2005046360 | 5/2005 |
| WO | WO 2006124892 | 11/2006 |
| WO | WO 2008014685 | 2/2008 |
| WO | WO 2008133884 | 11/2008 |
| WO | WO 2010008860 | 1/2010 |
| WO | WO 2010118888 | 10/2010 |
| WO | WO 2014018133 | 1/2014 |
| WO | WO 2014/181333 | 11/2014 |

OTHER PUBLICATIONS

Perucho et al., "Trehalose rescues glial cell dysfunction in striatal cultures from HDR6/1 mice at early postnatal development," Molecular and Cellular Neurosciences, May 2016, 74: 128-145.

U.S. Appl. No. 17/355,607, Megiddo.

[No Author Listed], "Amyotrophic Lateral Sclerosis: Developing Drugs for Treatment: Guidance for Industry," US Food and Drug Administration, Center for Drug Evaluation and Research and Center for Biologics Evaluation and Research, prepared by Division of Neurology Products, Sep. 2019, 11 pages.

[No Author Listed], "ICH guideline Q3C (R5) on impurities: guideline for residual solvents," European Medicines Agency, retrieved on Aug. 2011, retrieved from URL<www.tga.gov.au/pdf/euguide/ich822602006.pdf>, 26 pages.

[No Author Listed], International Conference on Harmonisation of Technical Requirements for Registration of Pharmaceuticals for Human Use: Impurities: Guideline for Residual Solvents Q3C(R5), European Medicine Agency, Feb. 4, 2011, 29 pages.

Alcantara-Ortigoza et al., "Wide allelic heterogeneity with predominance of large IDS gene complex rearrangements in a sample of Mexican patients with Hunter syndrome," Clin. Genet., Jan. 14, 2016, 89(5):574-583.

Al-Sannaa et al., "The clinical and genetic Spectrum of Maroteaux-Lamy syndrome (Mucopolysaccharidosis VI) in the Eastern Province of Saudi Arabia," J Community Genet., Jan. 2018, 9(1):65-70.

Alves et al., "Allele-specific RNA silencing of mutant ataxin-3 mediates neuroprotection in a rat model of Machado-Joseph disease," PLoS One, Oct. 8, 2008, 3(10): e3341, 12 pages.

Amartino et al., "Identification of 17 novel mutations in 40 Argentinean unrelated families with mucopolysaccharidosis type II (Hunter syndrome)," Mol. Genet. Metab. Rep., Dec. 2014, 1: 401-406.

Andrade et al., "Sanfilippo syndrome: Overall review," Pediatric Int., Jun. 2015, 57(3):331-338.

Anonymous, "Trehalose in oculopharyngeal muscular dystrophy: The Hopemd; NCT02015481 study," Integrity, Thomson-Pharma, Dec. 20, 2013, 1 page.

Bach et al., "Molecular analysis of Hurler syndrome in Druze and Muslim Arab patients in Israel: multiple allelic mutations of the IDUA gene in a small geographic area.," Am. J. Hum. Genet., Dec. 1993, 53(2):330-338.

Bachmanov et al., "Food Intake, Water Intake, and Drinking Spout Side Preference of 28 Mouse Strains," Behav. Genet., Nov. 2002, 32(6):435-443.

Banerjee, et al., "PABPN1: molecular function and muscle disease," FEBS J. Sep. 2013, 280(17):4230-4250.

Beal, "Parkinson's disease: a model dilemma," Nature, Aug. 26, 2010, 466(7310):S8-10.

Bean et al., "Free the Data: One Laboratory's Approach to Knowledge-Based Genomic Variant Classification and Preparation for EMR Integration of Genomic Data," Hum. Mutat., Jun. 11, 2013, 34(9):1183-1188.

Becher et al., "Oculopharyngeal muscular dystrophy in Hispanic New Mexicans," Jama., Nov. 21, 2001, 286(19):2437-40.

Becker, et al. "Final Report of the Safety assessment of Hyaluronic Acid, Potassium Hyaluronate, and Sodium Hyaluronate," International J. of Toxicology, Jul. 2009, 28(4S):5-67.

Beesley et al., "Identification of 12 novel mutations in the a-N-acetylglucosaminidase gene in 14 patients with Sanfilippo syndrome type B (mucopolysaccharidosis type IIIB)," J. Med. Genet., 1998, 35(11):910-914.

Beesley et al., "Mutational analysis of Sanfilippo syndrome type A (MPS IIIA): identification of 13 novel mutations," J. Med. Genet., 2000, 37(9):704-707.

Beesley et al., "Sanfilippo syndrome type D: identification of the first mutation in the N-acetylglucosamine-6-sulphatase gene," J. Med. Genet., 2003, 40(3):192-194.

Berg et al., "Correlation between morphological alterations and enzyme activities in the mucosa of the small intestine," Scandinavian Journal of Gastroenterology, Nov. 30, 1973, 8(8):703-12.

Binda et al., "Cerebellar Development and Circuit Maturation: A Common Framework for Spinocerebellar Ataxias," Front. Neurosci., Apr. 2, 2020, Article 293, 14: 12 pages.

Blumen et al., "Epidemiology and inheritance of oculopharyngeal muscular dystrophy in Israel", Neuromuscul. Disord, Oct. 1, 1997, 7:S38-40.

Boelens et al., "Current International Perspectives on Hematopoietic Stem Cell Transplant for Inherited Metabolic Disorders," Pediatr. Clin. North America, Feb. 2010, 57:123-145.

Bouchard et al., "Recent studies on oculopharyngeal muscular dystrophy in Quebec," Neuromuscul. Disorders, Oct. 1997, 7(1):S22-S29.

Brands et al., "Mucopolysaccharidosis type VI phenotypes-genotypes and antibody response to galsulfase," Orphanet J. Rare Dis., 2013, 8(51), 10 pages.

Brunet et al., "Dystrophie musculaire oculo-pharyngee. Recensement des familles frarnaises et etudes genealogiques," Rev. Neurol., 1990, 4:425-429(with English Abstract).

Buck et al., "Prediction of human pharmacokinetics using physiologically based modeling: a retrospective analysis of 26 clinically tested drugs," Drug Metabolism and Disposition, Oct. 1, 2007, 35(10):1766-1780.

Buijsen, et al., "Genetics, Mechanisms, and Therapeutic Progress in Polyglutamine Spinocerebellar Ataxias," Neurotherapeutics, Jan. 3, 2019, (2):263-286.

Bunge et al., "Identification of 16 sulfamidase gene mutations including the common R74C in patients with mucopolysaccharidosis type IIIA (Sanfilippo A)," Hum. Mutat., 1997, 10(6):479-485.

Bunge et al., "Identification of 31 novel mutations in the N-acetylgalactosamine-6-sulfatase gene reveals excessive allelic heterogeneity among patients with Morquio A syndrome," Hum. Mutat., 1997, 10(3):223-232.

Bunge et al., "Mucopolysaccharidosis is Type 1: Identification of 13 Novel Mutations of the a-L-Iduronidase Gene," Hum. Mutat., 1995, 6(1):91-94.

Bunge et al., "Mucopolysaccharidosis type IIIB (Sanfilippo B): identification of 18 novel á-N-acetylglucosaminidase gene mutations," J. Med. Genet., 1999, 36(1):28-31.

Bunge et al., "Mutation analysis of the iduronate-2-sulfatase gene in patients with mucopolysaccharidosis type II (Hunter syndrome)," Hum. Mol. Genet., 1992, 1(5):335-339.

Buteau, "Deuterated Drugs: Unexpectedly Nonobvious?", Journal of High Technology Law 22, 2009, 53 pages.

(56) References Cited

OTHER PUBLICATIONS

Caciotti et al., "GM1 gangliosidosis and Morquio B disease: An update on genetic alterations and clinical findings," Biochem. Biophys. Acta., 2011, 1812:782-790.

Castillo et al., "Trehalose delays the progression of amyotrophic lateral sclerosis by enhancing autophagy in motoneurons," Autophagy, 2013, 9(9):1308-1320.

Chen et al., "Trehalose Attenuates the Gait Ataxia and Gliosis of Spinocerebellar Ataxia Type 17 Mice," Neurochem. Res. 2015, 40(4):800-810.

Clarke et al., "Mucopolysaccharidosis Type I," Univ. of Wash., Oct. 31, 2002, 33 pages.

ClinicalTrials.gov, [online] "Oral Trehalose Therapy to Reverse Arterial Aging in Middle-Aged and Older Adults," available no later than Apr. 11, 2012, retrieved on Jul. 2, 2019, retrieved from URL<http://clinicaltrials.gov/ct2/show/NCT01575288, 5 pages.

Coarelli et al., "Recent advances in understanding dominant spinocerebellar ataxias from clinical and genetic points of view," F1000Res., Nov. 12, 2018, 7(F1000 Faculty Rev):1781: 10 pages.

Coll et al., "Allelic heterogeneity in Spanish patients with Sanfilippo disease type B. Identification of eight new mutations," J. Inherit. Metab. Dis., Feb. 2001, 24(1):83-84.

Couthino, et al., "Glycosaminoglycan Storage Disorders: A Review," Biochem. Res. Intl., Oct. 2011, Article ID 471325, 17 pages.

Coutinho et al., "Molecular characterization of Portuguese patients with mucopolysaccharidosis IIIC: Two novel mutations in the HGSNAT gene," Clin. Genet., Jul. 9, 2008, 74(2):194-195.

Crook et al., "Huntington's disease: can mice lead the way to treatment?" Neuron, Feb. 10, 2011,69(3):423-35.

Crotty et al., "Mutation R468W of the iduronate-2-sulfatase gene in mild Hunter syndrome (mucopolysaccharidosis type II) confirmed by in vitro mutagenesis and expression," Hum. Mol. Genet., 1992, 1(9):755-757.

Davies et al "Trehalose reduces aggregate formation and delays pathology in a transgenic mouse model of oculopharyngeal muscular dystrophy", Human Molecular Genetics, Nov. 30, 2005, 15(1):23-31.

Davies et al., "Oculopharyngeal muscular dystrophy: potential therapies for an aggregate-associated disorder," The International Journal of Biochemistry & Cell Biology, Jan. 1, 2006, 38(9):1457-1462.

Debnath et al., "Poly(trehalose) nanoparticles prevent amyloid aggregation and suppress polyglutamine aggregation in a Huntington's disease model mouse," ACS Appl Mater Interfaces, Jun. 20, 2017; 9(28):24126-24139.

DeBosch et al., "Trehalose inhibits solute carrier 2A (SLC2A) proteins to induce autophagy and prevent hepatic steatosis," Science Signaling, Feb. 23, 2016, 9(416):1-14.

Dehay et al., "Pathogenic Lysosomal Depletion in Parkinson's Disease," J Neuroscience, Sep. 15, 2010, 30:12535-12544.

Delaney et al., "Methods of Neurodevelopmental assessment in children with neurodegenerative disease: Sanfilippo syndrome," JIMD Reports Nov. 5, 2023, 13:129-37.

Demydchuk et al., "Insights into Hunter syndrome from the structure of iduronate-2-sulfatase," Nat. Commun's., Jun. 8, 2017, 8: 15786, 9 pages.

Di Natale et al., "Analysis of Sanfilippo A gene mutations in a large pedigree," Clin, Genet., Apr. 2003, 63(4):314-318.

Dickson, "Neuropathology of non-Alzheimer degenerative disorders," Int. J. Clin. Exp. Pathol., 2010, 3(1):1-23.

Elbein et al., "New insights on trehalose: a multifunctional molecule," Glycobiology, 2003, 13(4):17R-27R.

Elcioglu et al., "A Novel Loss-of-Function Mutation in The GNS Gene Causes Sanfilippo Syndrome Type D," Genet. Couns., 2009, 20(2):133-139.

Emanuele, "Can Trehalose Prevent Neurodegeneration? Insights from Experimental Studies," Current Drug Targets, May 1, 2014, 15(5):551-557.

EMEA, "Avastin: EPAR-European Medicines Agency," Jan. 1, 2005, pp. 1-61.

Fabbri et al., "Measuring Subjective Sleep Quality: A Review," Int. J. Environ. Res. Public Health, Jan. 26, 2021, 18(3):1082, 50 pages.

Fan et al., "Polyglutamine (PolyQ) Diseases: Genetics to Treatments," Cell Transplantation, 2014; 23:441-458.

Fedele Sanfilippo syndrome: causes, consequences, and treatments. Appl. Clin. Genet., Nov. 25, 2015, 8:269-281.

Feldhammer et al., "Sanfilippo Syndrome Type C: Mutation Spectrum in the Heparan Sulfate Acetyl-CoA: a-Glucosaminide N-Acetyltransferase (HGSNAT) Gene," Hum. Mutat., Jan. 29, 2009, 30(6):918-925.

Ferla et al., "Prevalence of anti-adeno-associated virus serotype 8 neutralizing antibodies and arylsulfatase B cross-reactive immunologic material in mucopolysaccharidosis VI patient candidates for a gene therapy trial," Hum. Gene. Ther., Mar. 2015, 26(3):145-152.

Flomen et al., "Detection of point mutations and a gross deletion in six Hunter Syndrome patients," Genomics, Jul. 1992, 13(3):543-550.

Fukuda et al., "Mucopolysaccharidosis Type IVA N-Acetylgalactosamine-6-Sulfate Sulfatase Exonic Point Mutations in Classical Morquio and Mild Cases," J. Clin. Invest., Sep. 1992, 90(3):1049-1053.

Gabrielli et al., "An adult Sanfilippo type A patient with homozygous mutation R206P in the sulfamidase gene," Am. J. Med. Genet A., Feb. 15, 2005, 133A(1):85-89.

Garrido et al., "Maroteaux-Lamy syndrome: Functional characterization of pathogenic mutations and polymorphisms in the arylsulfatase B gene," Mol. Genet. Metab., 2008, 94(3):305-312.

Ghosh et al., "Recommendations on clinical trial design for treatment of Mucopolysaccharidosis Type III," Orphanet J. Rare Dis. 2017, 12:117, 15 pages.

Goddijn et al., "Inhibition of trehalase activity enhances trehalose accumulation in transgenic plants," Plant Physiology, Jan. 1997, 113(1):181-190.

Gomes et al., "Mutant superoxide dismutase 1 overexpression in NSC-34 cells: Effect of trehalose on aggregation, TDP-43 localization and levels of co-expressed glycoproteins," Neuroscience Letters, 2010, 475:145-149.

Gonçalves et al., "Caffeine and adenosine A2A receptor inactivation decreases striatal neuropathology in a lentiviral-based model of Machado-Joseph Disease," Ann. Neurol., 2013, 73: 655-666.

Goodman, "Neuroinflammation (Part 2): another role for trehalose?," Huntington's Disease Drug Works, Nov. 30, 2008, 3 pages.

Grewal et al., "Mutation analysis of oculopharyngeal muscular dystrophy in hispanic American families", Arch. Neurol., 1999, 56(11): 1378-1381.

Haer-Wigman et al., "Non-syndromic retinitis pigmentosa due to mutations in the mucopolysaccharidosis type IIIC gene, heparanalpha-glucosaminide N-acetyltransferase (HGSNAT)," Hum. Mol. Genet., Apr. 9, 2015, 24(13):3742-3751.

Hardiman et al., "Amyotrophic lateral sclerosis," Nature Reviews, Disease Primers, Oct. 5, 2017, 3(17071): 19 pages.

Harmatz et al., "A novel Blind Start study design to investigate vestronidase alfa for mucopolysaccharidoses VII, an ultra-rare genetic disease," Mol. Genet. Metab. 2018, 123:488-494.

Harris, "Mucopolysaccharides Disorder: A Possible New Genotype of Hurler's Syndrome," Am. J. Dis. Child., 1961, 102:741-742.

Heŕon et al., "Incidence and natural history of mucopolysaccharidosis type III in France and comparison with United Kingdom and Greece," Am. J. Med. Genet. A., 2011, 155A(1):58-68.

Hinek et al., "Impaired Elastic-Fiber Assembly by Fibroblasts from Patients with Either Morquio B Disease or Infantile GM1-Gangliosidosis is Linked to Deficiency in the 67-kD Spliced Variant of b-Galactosidase," Am. J. Hum. Genet., 2000, 67(1):23-36.

Hofer et al., "GM1 Gangliosidosis and Morquio B Disease: Expression Analysis of Missense Mutations Affecting the Catalytic Site of Acid b-Galactosidase," Hum. Mutat., Apr. 4, 2009, 30(8):1214-1221.

Hofer et al., "Phenotype determining alleles in GM1 gangliosidosis patients bearing novel GLB1 mutations," Clin. Genet., Jan. 11, 2010, 78(3):236-246.

Hopkins et al., "Large-volume IM injections: a Review of Best Practices," Oncology Nurse Advisor, Feb. 2013, 4(1):32-37.

(56) References Cited

OTHER PUBLICATIONS

Hopwood et al., "Molecular basis of mucopolysaccharidosis type II: Mutations in the iduronate-2-sulphatase gene," Hum Mutat., 1993, 2(6):435-442.

Hore et al., "Studies on disaccharidase activities of the small intestine of the domestic cat and other carnivorous mammals," Comp. Biochem. Physiol., 1968, 24: 717-725.

Hřebíček et al., "Mutations in TMEM76* Cause Mucopolysaccharidosis IIIC (Sanfilippo C Syndrome)," Am. J. Hum. Genet., Nov. 2006, 79:807-819.

Inchem.org [online], "WHO Food Additives Series 46: Trehalose," Jul. 2, 2019, retrieved on Jul. 2, 2019, retrieved from URL<http://Avww.inchem.orgldocuments/jecfa/jecmonolv46je05.htm>, 15 pages.

Innovation.ox.ac.uk.com [online], "University of Oxford Health Services Research Unit," Jun. 4, 2016, retrieved on Jul. 6, 2023, retrieved from URL<https://innovation.ox.ac.uk/outcome-measures/amyotrophic-lateral-sclerosis-assessment-questionnaire-alsaq/>, 3 pages.

International Preliminary Report on Patentability in Appl. No. PCT/IL2014/050411, mailed on Nov. 10, 2015, 19 pages.

International Preliminary Report on Patentability in Appln. No. PCT/US2020/053226, mailed Apr. 5, 2022, 8 pages.

International Search Report and Written Opinion in International Appln. No. PCT/IL2014/050411, mailed on Nov. 19, 2014, 28 pages.

International Search Report and Written Opinion for the International Application No. PCT/US2020/053226, mailed Dec. 23, 2020, 10 pages.

Ishii et al., "Clinical and molecular analysis of a Japanese boy with Morquio B disease," Clin. Genet., 1995, 48(2):103-108.

Jacobi et al., "Long-term disease progression in spinocerebellar ataxia types 1, 2, 3, and 6: a longitudinal cohort study," Lancet Neurol., Sep. 14, 2015, 201;14(11): 8 pages.

Jansen et al., "Sanfilippo syndrome type D: natural history and identification of 3 novel mutations in the GNS Gene," Arch. Neurol., Nov. 2007, 64(11):1629-1634.

Jenkinson et al., "Development and validation of short measure of health status for individuals with amyotrophic lateral sclerosis/motor neurone disease: the ALSAQ-40," J Neurol., 1999; 246 (Supplement 3): III/16-III/21.

Jenner, "Animal models of Parkinson's disease: a source of novel treatments and clues to the cause of the disease," British Journal of Pharmacology, Oct. 2011, 164(4):1357-1391.

Kaplan et al., "Sanfilippo syndrome type D," J. Pediatr., Feb. 1987, 110(2):267-271.

Karageorgos et al., "Mutational analysis of mucopolysaccharidosis type VI patients undergoing a trial of enzyme replacement therapy," Hum. Mutat., Mar. 23, 2004, 23(3):229-233.

Kato et al., "A novel common missense mutation G301C in the N-acetylgalactosamine-6-sulfate sulfatase gene in mucopolysaccharidosis IVA," Hum. Genet., Nov. 1997, 101(1):97-101.

Kaye et al., "Beta-galactosidase gene mutations in patients with slowly progressive GM1 gangliosidosis," J. Child. Neurol., Jun. 1997, 12(4):242-247.

Kresse et al., "Sanfilippo disease type D: Deficiency of N-acetylglucosamine-6-sulfate sulfatase required for heparan sulfate degradation," Proc. Natl. Acad. Sci. USA, Nov. 1980, 77(11):6822-6826.

Kruger, et al., "Autophagic degradation of tau in primary neurons and its enhancement by trehalose," Neurobiology of Aging, 2012, 33:2291-2305.

Kulisevsky, et al., "Neuropsychiatric assessment of Gilles de la Tourette Patients: comparative study with other hyperkinetic and hypokinetic movement disorders," Total Functional Capacity (TFC) Scale Movement Disorders, Nov. 6, 2001, 16(6): 1098-1104.

Kwak et al., "Report of 5 novel mutations of the α-Liduronidase gene and comparison of Korean mutations in relation with those of Japan or China in patients with mucopolysaccharidosis I," BMC Med. Genet., 2016, 17(58): 5 pages.

Lange, "Current research on the neuroprotective therapy of Huntington's Disease," Materialien zur Huntington-Krankheit, Nr. 180, Jun. 1, 2008, pp. 1-32.

Langer, "New methods of drug delivery," Science, Sep. 28, 1990, 249(4976):1527-33.

Lee et al., "Clinical, radiologic, and genetic features of Korean patients with Mucopolysaccharidosis IVA," Korean J. Pediatr., 2012, 55(11):430-437.

Lee et al., "The Potential of Lactulose and Melibiose, Two Novel Trehalase-Indigestible and Autophagy-Inducing Disaccharides, for PolyQ-Mediated Neurodegenerative Disease Treatment," Neurotoxicology, 2015, 48:120-130.

Lee-Chen et al., "Mucopolysaccharidosis type I: identification of novel mutations that cause Hurler/Scheie syndrome in Chinese families," J. Med. Genet., 1997, 34(11):939-941.

Li et al., "Detection of four novel mutations in the iduronate-2-sulphatase gene by single-strand conformation polymorphism analysis of genomic amplicons," J. Inherit. Metab. Dis., 1996, 19(1):93-94.

Li et al., "The Use of the R6 Transgenic Mouse Models of Huntington's Disease in Attempts to Develop Novel Therapeutic Strategies," The Journal of the American Society for Experimental NeuroTherapeutics, 2005, 2:447-464.

Li et al., "Trehalose Decreases Mutant SOD1 Expression and Alleviates Motor Deficiency in Early But Not End-Stage Amyotrophic Lateral Sclerosis in A Sod1-G03A Mouse Model," Neuroscience, 2015, 298:12-25.

Li, "The Role of Autophagic Degradation of Disease-related Proteins in ALS and Intervention Study of Trehalose in ALS Transgenic Mice," Dissertation, Hebei Medical University, 2013, 108 pages (English Translation).

Lin et al., "Novel Lactulose and Melibiose Targeting Autophagy to Reduce PolyQ Aggregation in Cell Models of Spinocerebellar Ataxia 3," CNS Neurol. Disord. Drug Targets, 2016, 15(3):351-359.

Litjens et al., "Identification, Expression, and Biochemical Characterization of N-Acetylgalactosamine-4-Sulfatase Mutations and Relationship with Clinical Phenotype in MPS-VI Patients," Am. J. Hum. Genet., 1996, 58(6):1127-1134.

Lotfi et al., "Trehalose reduces retinal degeneration, neuroinflammation and storage burden caused by a lysosomal hydro lase deficiency," Autophagy, Jul. 23, 2018, 14(8):1419-1434.

Luyckx et al., "Trehalose: an intriguing disaccharide with potential for medical application in ophthalmology," Clinical Ophthalmology, May 1, 2011, 5:577-581.

Mangas et al., "Molecular analysis of mucopolysaccharidosis type IIIB in Portugal: evidence of a single origin for a common mutation (R234C) in the Iberian Peninsula," Clin, Genet., Nov. 20, 2007, 73(3):251-256.

March, "Advanced Organic Chemistry: Reactions, Mechanisms and Structure," 4th Ed., New York: Wiley-Interscience, Feb. 1993, 70(2), 1 page.

Mardones et al., "Mystery solved: Trehalose Kickstarts Autophagy by Blocking Glucose Transport," Science Signaling, Feb. 23, 2016, 9(416)fs2: 4 pages.

Mathew et al., "Mutations in ARSB in MPS VI patients in India," Mol. Genet. Metab. Rep., Jul. 2015, 4:53-61.

Mauri, "Trehalose-Mediated Enhancement of Glycosaminoglycan Degradation in the Lysosomal Storage Disorder Mucopolysaccharidosis III," Thesis for the degree of Doctor, University of Cologne, Jan. 29, 2014, 172 pages.

Mayer et al., "SLC2A8 (GLUT8) is a mammalian trehalose transporter required for trehalose-induced autophagy," Sci Rep., Dec. 6, 2016, 6(38586), 15 pages.

McClellan et al., "Molecular chaperones and the art of recognizing a lost cause," Nature Cell Biology, Feb. 2001, 3(2):E51-53.

Medina et al., "Transcriptional activation of lysosomal exocytosis promotes cellular clearance," Developmental Cell Article, Sep. 13, 2011, 21:421-430.

Mendonça, et al., "Transplantation of cerebellar neural stem cells improves motor coordination and neuropathology in Machado-Joseph disease mice," Brain, 2015, 138(Pt 2):320-335.

(56) References Cited

OTHER PUBLICATIONS

Meyer et al., "Scoring evaluation of the natural course of mucopolysaccharidosis type IIIA (Sanfilippo type A)," Pediatrics, Nov. 2007, 120:e1255-e1261.

Meyer-Luehmann et al., "Rapid appearance and local toxicity of amyloid-β plaques in a mouse model of Alzheimer's disease," Nature, Feb. 7, 2008, 451(7179):720-724.

Montano et al., "Mucopolysaccharidosis IVA: Characterization of a common mutation found in Finnish patients with attenuated phenotype," Hum. Genet., Apr. 30, 2003, 113(2):162-169.

Morrone et al., "Molecular testing of 163 patients with Morquio A (Mucopolysaccharidosis IVA) identifies 39 novel GALNS mutations," Mol. Genet. Metab., Mar. 2014, 112(2):160-170.

Morrone et al., "β-galactosidase gene mutations affecting the lysosomal enzyme and the elastin-binding protein in GM1-gangliosidosis patients with cardiac involvement," Hum. Mutat., Mar. 2000, 15(4):354-366.

Muenzer, "Overview of the mucopolysaccharidoses," Rheumatology, Dec. 2011, vol. 50(5):v4-v12.

Muschol et al., "Transport, enzymatic activity, and stability of mutant sulfamidase (SGSH) identified in patients with mucopolysaccharidosis type III A," Hum. Mutat., Apr. 2004, 23(6):559-566.

Myers "Huntington's Disease Genetics," The Journal for the American Society for Experimental NeuroTherapeutics, Apr. 2004; 1:255-262.

Nascimento-Ferreira et al., "Beclin 1 mitigates motor and neuropathological deficits in genetic mouse models of Machado-Joseph disease," Brain, 2013, 136(Pt7): 2173-2188.

Nascimento-Ferreira et al., "Overexpression of the autophagic beclin-1 protein clears mutant ataxin-3 and alleviates Machado-Joseph disease," Brain, May 2011, 134: 1400-1415.

Natowicz et al., "Clinical and Biochemical Manifestations of Hyaluronidase Deficiency," N. Engl. J. Med., Oct. 1996, 335(14):1029-33.

Neumann et al., "Ubiquitinated TDP-43 in Frontotemporal Lobar Degeneration and Amyotrophic Lateral Sclerosis," Science, Oct. 6, 2006, 314(5796):130-133.

Ninds.nih.gov, [online] "Amyotrophic Lateral Sclerosis (ALS) Fact Sheet," Jun. 2013, retrieved on Jan. 11, 2017, retrieved from URL<https://www.ninds.nih.gov/health-information/disorders/amyotrophic-lateral-sclerosis-alsADD>, 12 pages.

Nóbrega et al., "Overexpression of Mutant Ataxin-3 in Mouse Cerebellum Induces Ataxia and Cerebellar Neuropathology," Cerebellum, 2013, 12(4): 441-455.

Nykamp et al., "Sherloc: a comprehensive refinement of the ACMG-AMP variant classification criteria," Genet. Med., Oct. 2017, (10):1105-1117.

Ohtake et al., "Trehalose: Current use and future applications," Journal of Pharmaceutical Science, Jun. 1, 2011, 100(6):2020-2053.

Oshima et al., "Human beta-galactosidase gene mutations in morquio B disease," Am. J. Hum. Genet., Nov. 1991, 49(5):1091-1093.

Oskarsson et al., "Amyotrophic lateral sclerosis: An update for 2018," Mayo Clin. Proc., Nov. 2018, (93)11:1617-1628.

Quesleti et al., "Molecular characterization of MPS IIIA, MPS IIIB and MPS IIIC in Tunisian patients," Clin. Chim. Acta., Nov. 2011, 412(23-24):2326-31.

Partial European Search Report in European Appln. 22216238.0, dated Jun. 16, 2023, 22 pages.

Perlman, "Hereditary Ataxia Overview," U.S. National Library of Medicine: National Center for Biotechnology Information, Gene Reviews [Internet], University of Washington, Oct. 28, 1998, 20 pages.

Perucho et al., "Trehalose Protects from Aggravation of Amyloid Pathology Induced by Isoflurane Anesthesia in APPswe Mutant Mice," Current Alzheimer's Research, Jan. 2012, 9(3):334-343.

Petry et al., "Mucopolysaccharidosis type VI: Identification of novel mutations on the arylsulphatase B gene in South American patients," J. Inherit. Metab. Dis., Jul. 2005, 28(6):1027-1034.

Piotrowska et al., "Correlation between severity of mucopolysaccharidoses and combination of the residual enzyme activity and efficiency of glycosaminoglycan synthesis," Acta Paediatr., Apr. 2009, 98(4):743-9.

Pollard et al., "Molecular characterization of 355 mucopolysaccharidosis patients reveals 104 novel mutations," J. Inherit. Metab. Dis., Mar. 2013, 36(2):179-87.

RareDiseases.org [online], "Autosomal Dominant Hereditary Ataxia," Mar. 14, 2017, retrieved on Jun. 30, 2023, retrieved from URL<https://rarediseases.org/rare-diseases/autosomal-dominant-hereditary-ataxia/>, 16 pages.

Richards et al., "Standards and guidelines for the interpretation of sequence variants: a joint consensus recommendation of the American College of Medical Genetics and Genomics and the Association for Molecular Pathology," Genet. Med., May 2015, 17(5):405-424.

Rodríguez-Navarro et al. "Trehalose ameliorates dopaminergic and tau pathology in parkin deleted/tau overexpressing mice through autophagy activation," Neurobiology of Disease, May 2010, 39:423-438.

Ross et al., "Movement Disorder Society Task Force Viewpoint: Huntington's Disease Diagnostic Categories," Movement Disorders Clinical Practice, Sep. 2019, 6(7):541-546.

Rowe et al., Handbook of Pharmaceutical Excipients, McGraw Hill, 2006, 7 pages.

Ruijter et al., "Clinical and genetic spectrum of Sanfilippo type C (MPS IIIC) disease in The Netherlands," Mol. Genet. Metab., Feb. 2008, 93(2):104-111.

Rusmini et al., "Trehalose induces autophagy via lysosomal-mediated TFEB activation in models of motoneuron degeneration," Autophagy, Apr. 2019, 15(4):631-651.

Sanfilippo, et al., "Mental retardation associated with acid mucopolysachariduria (heparitin sulfate type)," J. Pediatrics, Oct. 1, 1963, 63(4):837-838.

Santamaria et al., "Twenty-one novel mutations in the GLB1 gene identified in a large group of GM1-gangliosidosis and Morquio B patients: possible common origin for the prevalent p.R59H mutation among gypsies," Hum. Mutat., Oct. 2006, 27(10):1060, 11 pages.

Sarkar et al., "Neuroprotective effect of the chemical chaperone, trehalose in a chronic MPTP-induced Parkinson's disease mouse model," Neurotoxicology, 2014, 44:250-262.

Sarkar et al., "Trehalose, a novel mTOR-independent autophagy enhancer, accelerates the clearance of mutant huntingtin and alpha-synuclein," J. Biol. Chem., Feb. 23, 2007, 282:5641-5652.

Schmidtchen et al., "NAGLU Mutations Underlying Sanfilippo Syndrome Type B," Am. J. Hum. Genet, Jan. 1998, 62(1):64-69.

Schmitz-Hübsch et al., "Scale for the assessment and rating of ataxia: development of a new clinical scale," Neurology, Jun. 13, 2006, 66(11):1717-1720.

Scott et al., "Identification of mutations in the alpha-L-iduronidase gene (IDUA) that cause Hurler and Scheie syndromes," Am. J. Hum. Genet., Nov. 1993, 53(5):973-986.

Seidel et al., "Brain pathology of spinocerebellar ataxias," Acta Neuropathol, 2012,124:1-21.

Seki et al., "Effect of Trehalose on the Properties of Mutant γPKC, Which Causes Spinocerebellar Ataxia Type 14, in Neuronal Cell lines and Cultured Purkinje Cells," Journal of Biological Chemistry, Oct. 22, 2010, 285(43):33252-33264.

Seyedhassani et al., "Novel missense mutation in the GALNS gene in an affected patient with severe form of mucopolysaccharidosis type IVA," Clin Chim. Acta., Oct. 2015, 450:121-124.

Shamseldin et al., "Identification of embryonic lethal genes in humans by autozygosity mapping and exome sequencing in consanguineous families," Genome Biol., Jun. 2015, 16(1):116, 7 pages.

Shapiro et al., "A Prospective Natural History Study of Mucopolysaccharidosis Type IIIA," The Journal of Pediatrics, Mar. 2016, 170:278-287.

Shapiro et al., "Assessments of neurocognitive and behavioral function in the mucopolysaccharidoses," Mol. Genet. Metab., Dec. 2017, 122:8-16.

Shatsky "Evidence for the Use of Intramuscular Injection in Outpatient Practice," American Academy of Family Physicians, Feb. 15, 2009, 79(4):297-300.

(56) References Cited

OTHER PUBLICATIONS

Shefner et al., "Quantitative strength testing in ALS clinical trials," Neurology, Aug. 9, 2016, 87(6):617-624.

Shepherd et al., "Short-Chain Carbohydrates and Functional Gastrointestinal Disorders," American Journal of Gastroenterology, May 1, 2013,108(5):707-717.

Shipley et al., "Mutational Analysis of a Patient with Mucopolysaccharidosis Type VII, and Identification of Pseudogenes," Am. J. Hum. Genet., 1993, 52(3):517-526.

Shoulson, "Huntington disease: Functional capacities in patients treated with neuroleptic and antidepressant drugs," Neurology, Oct. 1981, 31:1333-1335.

Silva et al., "Six Novel β-Galactosidase Gene Mutations in Brazilian Patients with GM1-Gangliosidosis," Hum. Mutat., Jul. 17, 2019, 13(5):401-409.

Simões et al., "Calpastatin-mediated inhibition of calpains in the mouse brain prevents mutant ataxin 3 proteolysis, nuclear localization and aggregation, relieving Machado-Joseph disease," Brain, May 2012, 135:2428-2439.

Spires-Jones et al., "Passive immunotherapy rapidly increases structural plasticity in a mouse model of Alzheimer disease," Neurobiol Dis., Feb. 1, 2009, 33(2):213-220.

Stephan, et al., "A case for a non-transgenic animal model of Alzheimer's disease," Genes, Brain and Behavior, Jan. 2005, 4(3):157-172.

Storch et al., "Mutational analysis in longest known survivor of mucopolysaccharidosis type VII," Hum. Genet., Feb. 2003, 112(2):190-194.

Tanaka et al., "A novel therapeutic strategy for polyglutamine diseases by stabilizing aggregation prone proteins with small Molecules," Journal of Molecular Medicine, May 2005, 83:343-352.

Tanaka et al., "Molecular analysis of the α-N-acetylglucosaminidase gene in seven Japanese patients from six unrelated families with mucopolysaccharidosis IIIB (Sanfilippo type B), including two novel mutations," J. Hum. Genet., Mar. 2002, 47(9):484-487.

Tanaka et al., "Trehalose alleviates polyglutamine-mediated pathology in a mouse model of Huntington disease," Nature Medicine, Feb. 1, 2004,10(2):148-154.

Tang et al., "Mucopolysaccharidosis type IIIB mutations in Chinese patients: Identification of two novel NAGLU mutations and analysis of two cases involving prenatal diagnosis," Clin. Chim. Acta., Apr. 2013, 419:33-38.

Tessitore et al., "Molecular defects in the α-N-acetylglucosaminidase gene in Italian Sanfilippo type B patients," Hum. Genet., Dec. 2000, 107:568-576.

Tétreault et al., "Adult-onset painful axonal polyneuropathy caused by a dominant NAGLU mutation," Brain, Jun. 2015, 138(6):1477-1483.

Tieu et al., "Four novel mutations underlying mild or intermediate forms of alpha-L-iduronidase deficiency (MPS IS and MPS IH/S)," Hum. Mutat., 1995, 6(1):55-59.

Tomanin et al., "Mucopolysaccharidosis type VI (MPS VI) and molecular analysis: Review and classification of published variants in the ARSB gene," Hum. Mutat., Dec. 2018, 39(12):1788-1802.

Tomatsu et al., "Fourteen novel mucopolysaccharidosis IVA producing mutations in GALNS gene," Hum. Mutat., Jan. 1999, 10(5):368-375.

Tomatsu et al., "Mucopolysaccharidosis type VII: Characterization of mutations and molecular heterogeneity," Am. J. Hum. Genet., Jan. 1991, 48(1):89-96.

Tomatsu et al., "Two new mutations, Q473X and N487S, in a Caucasian patient with mucopolysaccharidosis IVA (Morquio disease)," Hum. Mutat., 1995, 6(2):195-196.

Torashima et al., "Lentivector-mediated rescue from cerebellar ataxia in a mouse model of spinocerebellar ataxia," EMBO Rep., Mar. 14, 2008, 9(4):393-399.

Triggs-Raine et al., "Mutations in HYAL1, a member of a tandemly distributed multigene family encoding disparate hyaluronidase activities, cause a newly described lysosomal disorder, mucopolysaccharidosis IX," Proc. Natl. Academy Sci., May 1999, 96(11):6296-6300.

Truxal et al., "A prospective one-year natural history study of mucopolysaccharidosis types IIIA and IIIB: Implications for clinical trial design," Mol. Genet. Metab., Nov. 2016, 119(3):239-248.

Uchida et al., "Activation of Master Autophagy Regulator TFEB during Systemic LPS Administration in the Cornea," J. Toxicol. Pathol., 2014, 27:153-158.

Valstar et al. "Sanfilippo syndrome: A mini-review," J. Inherit. Metab. Dis., Apr. 4, 2008, 31:240-252.

Valstar et al., "Mucopolysaccharidosis Type IIIA: Clinical Spectrum and Genotype-Phenotype Correlations," Ann. Neurol., May 19, 2010, 68:876-887.

Valstar et al., "Mucopolysaccharidosis type IIID: 12 new patients and 15 novel mutations," Hum. Mutat. 2010; 31:E1348-1360.

Van Goor et al., "Effect of ivacaftor on CFTR forms with missense mutations associated with defects in protein processing or function," J. Cyst. Fibros., Jan. 2014, 13(1):29-36.

Van Hove et al., "Late-Onset visceral presentation with cardiomyopathy and without neurological symptoms of adult Sanfilippo A syndrome," Am. J. Med. Genet. A., Mar. 2003, 118A(4):382-387.

Velasco et al., "Natural History of Sanfilippo Syndrome Type C in Boyacá, Colombia: A Neurogenetic Description," J. Child. Neurol., 32(2):177-183.

Venturi et al., "Molecular analysis of 30 mucopolysaccharidosis type I patients: evaluation of the mutational spectrum in Italian population and identification of 13 novel mutations," Hum. Mutat., Aug. 2002, 20(3):231, 9 pages.

Vervoort et al., "A mutation (IVS8+ 0.6 kbdelTC) creating a new donor splice site activates a cryptic exon in an Alu-element in intron 8 of the human β-glucuronidase gene," Hum. Genet., Dec. 1998, 103(6):686-693.

Villani et al., "Large Deletion Involving Exon 5 of the Arylsulfatase B Gene Caused Apparent Homozygosity in a Mucopolysaccharidosis Type VI Patient," Genet. Test. Mol. Biomark., 2010, 14(1):113-120.

Vonsattel, "Huntington disease models and human neuropathology: similarities and differences," Acta Neuropathologica, Jan. 2008, 115:55-69.

Wallace et al., "Development and validation of a self-report symptom inventory to assess the severity of oral-pharyngeal dysphagia," Thesis for the degree of Master of Science, University of New South Wales, Gastroenterology, 2000, 118:99 pages.

Wang et al., "Mucopolysaccharidosis IVA mutations in Chinese patients: 16 novel mutations," J. Hum. Genet., Jun. 24, 2010, 55(8):534-540.

Weber et al., "Novel Mutations in Sanfilippo a Syndrome: Implications for Enzyme function," Hum. Mol. Genet., Sep. 1997, 6(9):1573-1579.

Weber et al., "Sanfilippo type B syndrome (mucopolysaccharidosis III B): allelic heterogeneity corresponds to the wide spectrum of clinical phenotypes," *Eur. J. Hum. Genet.*, Mar. 1999, 7(1):34-44.

Whitely et al., Observational Prospective Natural History of Patients with Sanfilippo Syndrome Type B, The Journal of Pediatrics, Jun. 2018, pp. 198-206.

Winklhofer et al., "Geldanamycin Restores a Defective Heat Shock Response in Vivo," J. Biol. Chem., 2001, 276(48):45160-45167.

Wirths et al., "Neuron Loss in Transgenic Mouse Models of Alzheimer's Disease," International Journal of Alzheimer's Disease, Aug. 12, 2010, 6 pages.

Wraith, "The mucopolysaccharidoses: a clinical review and guide to management," Arch. Dis. Child., Mar. 1995, 72(3):263-267.

Wu et al., "Mutational studies in a patient with the hydrops fetalis form of mucopolysaccharidosis type VII," Hum. Mutat., 2(6):446-57 (1993).

Yamada et al., "Four novel mutations in Mucopolysaccharidosis type VII including a unique base substitution in exon 10 of the β-glucuronidase gene that creates a novel 5'-splice site," Hum. Mol. Genet., 1995, 4(4):651-655.

Yamada et al., "Molecular Heterogeneity in Mucopolysaccharidosis IVA in Australia and Northern Ireland: Nine Novel Mutations

(56) References Cited

OTHER PUBLICATIONS

Including T312S, a Common Allele That Confers a Mild Phenotype," Hum. Mutat., 1998, 11(3):202-208.

Yamamoto et al., "Reversal of neuropathology and motor dysfunction in a conditional model of Huntington's disease," Cell, Mar. 31, 2000, 101(1):57-66.

Yang et al., "Theme 3 In vitro experimental models," Amyotrophic Lateral Sclerosis and Frontotemporal Degeneration, Nov. 8, 2019, 20 (Suppl. S1):135-59.

Yang, "Intracerebral Transplantation of Neural Stem Cells Combined with Trehalose Ingestion Alleviates Pathology in a Mouse Model of Huntington's Disease," Journal of Neuroscience Research, Aug. 2008, 87:26-33.

Yassaee et al., "Clinical, biochemical and molecular features of Iranian families with mucopolysaccharidosis: A case series," Clin. Chim. Acta., Nov. 2017, 474:88-95.

Yogalingam et al., "Mucopolysaccharidosis type IIIB: characterisation and expression of wild-type and mutant recombinant α-N-acetylglucosaminidase and relationship with Sanfilippo phenotype in an attenuated patient," Biochim. Biophys. Acta. (BBA)-Molecular Basis of Disease, Nov. 2000, 1502(3):415-425.

Yoshida et al., "Human beta-Galactosidase Gene Mutations in GM1-Gangliosidosis: A Common Mutation among Japanese Adult/Chronic Cases," Am. J. Hum. Genet., 1991, 49(2):435-442.

Zhang et al., "MTOR-independent, autophagic enhancer trehalose prolongs motor neuron survival and ameliorates the autophagic flux defect in a mouse model of amyotrophic lateral sclerosis," Autophagy, Apr. 2014, 10(4):588-602.

Zhao et al., "Genotype-Phenotype Correspondence in Sanfilippo Syndrome Type B," Am. J. Hum. Genet., Jan. 1998, 62(1):53-63.

Zhao et al., "The molecular basis of Sanfilippo syndrome type B," Proc. Natl. Acad. Sci. USA, 1996, 93(12):6101-6105.

\* cited by examiner

| Mucopolysaccharidosis | Gene | Enzyme | Aggregation Product(s) |
|---|---|---|---|
| Hurler syndrome (MPS IH) | IDUA | α-L-iduronidase | Heparan sulfate, dermatan sulfate |
| Hurler-Scheie syndrome (MPS IH/S) | IDUA | α-L-iduronidase | Heparan sulfate, dermatan sulfate |
| Scheie syndrome (MPS IS or MPS V) | IDUA | α-L-iduronidase | Heparan sulfate, dermatan sulfate |
| Hunter syndrome (MPS II) | IDS | iduronate sulfatase | Heparan sulfate, dermatan sulfate |
| Sanfillippo syndrome A (MPS IIIA) | SGSH | heparan sulfamidase | Heparan sulfate |
| Sanfillippo syndrome B (MPS IIIB) | NAGLU | N-acetylglucosaminidase | Heparan sulfate |
| Sanfillippo syndrome C (MPS IIIC) | HGSNAT | heparan-α-glucosaminide N-acetyltransferase | Heparan sulfate |
| Sanfillippo syndrome D (MPS IIID) | GNS | N-acetylglucosamine 6-sulfatase | Heparan sulfate, keratan sulfate |
| Morquio syndrome A (MPS IVA) | GALNS | galactose-6-sulfate sulfatase | Chondroitin sulfate, keratan sulfate |
| Morquio syndrome B (MPS IVB) | GLB1 | β-galactosidase | Keratan sulfate |
| Maroteaux-Lamy syndrome (MPS VI) | ARSB | arylsulfatase B | Dermatan sulfate |
| Sly syndrome (MPS VII) | GUSB | β-glucuronidase | Heparan sulfate |
| Natowicz syndrome (MPS IX) | HYAL1 | hyaluronidase | Hyaluronic acid |

TREHALOSE FORMULATIONS AND USES THEREOF

RELATED APPLICATION

This application is a National Stage application under 35 U.S.C. § 371 of International Application No. PCT/US2020/053226 having an International Filing Date of Sep. 29, 2020, which claims the benefit of U.S. Provisional Application No. 62/908,784, filed Oct. 1, 2019, which are incorporated herein by reference in their entirety.

TECHNICAL FIELD

The present disclosure relates to novel trehalose compositions, processes for making the compositions, and the use of the compositions in therapy. More particularly, it relates to trehalose compositions useful in the treatment and/or amelioration of symptoms of mucopolysaccharidoses.

BACKGROUND

The mucopolysaccharidoses (MPSs) are a group of inherited lysosomal storage disorders (LDSs) that are characterized by abnormalities in multiple organ systems and reduced life expectancy. The MPSs are heterogeneous, progressive disorders where subjects typically appear normal at birth, but during early childhood they experience the onset of clinical disease, including skeletal, joint, airway and cardiac symptoms, and hearing, vision, and cognitive impairment. MPSs are caused by deficiency in the activity of a single, specific lysosomal enzyme required for glycosaminoglycan (GAG) degradation. See Muenzer, et al., *Rheumatology*, Volume 50, Suppl. Issue No. 5, pp. v4-v12 (2011).

Glycosaminoglycans, with the exception of hyaluronic acid, are the degradation products of proteoglycans in the extracellular matrix. The proteoglycans are proteolytic cleaved, giving rise to GAGs, which enter the lysosome for intracellular digestion. There are four different pathways of lysosomal degradation of GAGs, depending on the molecule to be degraded: dermatan sulfate, heparan sulfate, keratan sulfate, and chondroitin sulfate. The stepwise degradation of glycosaminoglycans requires ten different enzymes. Deficiencies of each one of these enzymes have been reported and result in seven different MPSs, all of them sharing a series of clinical features to varying degrees. See Couthino, et al., *Biochem. Res. Intl.*, Volume 2012, Article ID 471325, pp. 1-16.

Current treatment options for MPSs include hematopoietic stem cell transplant (HSCT) and enzyme replacement therapy (ERT). However, HSCT is invasive and expensive, and ERT is also expensive, and provides an uneven distribution of enzyme, leaving certain areas such as the bones, lungs, and brain untreated. Both of these treatments also require access to advanced medical care facilities. Thus, there is a need for MPS treatments that efficacious and less invasive.

SUMMARY

Provided herein are methods of treating a mucopolysaccharidosis in a subject in need thereof, comprising administering intravenously an aqueous pharmaceutical formulation to the subject, wherein the formulation comprises a single active ingredient consisting essentially of substantially purified trehalose, wherein: the pH of the formulation is about 4.5 to 7.0; the formulation contains less than about 0.75 endotoxin units per mL; the formulation has an osmolality of about 280 mOsm/kg to 330 mOsm/kg; the formulation is administered over about 15 minutes to about 150 minutes; wherein the substantially purified trehalose is present in the formulation in an amount of about 5% (w/v) to about 15% (w/v); and wherein the substantially purified trehalose contains less than about 0.5% contaminants.

Also provided herein are methods of alleviating one or more symptoms of a mucopolysaccharidosis in a subject in need thereof, comprising administering intravenously an aqueous pharmaceutical formulation to the subject, wherein the formulation comprises a single active ingredient consisting essentially of substantially purified trehalose, wherein: the pH of the formulation is about 4.5 to 7.5; the formulation contains less than about 0.75 endotoxin units per mL; the formulation has an osmolality of about 280 mOsm/kg to 330 mOsm/kg; the formulation is administered over about 15 minutes to about 150 minutes; wherein the substantially purified trehalose is present in the formulation in an amount of about 5% (w/v) to about 15% (w/v); and wherein the substantially purified trehalose contains less than about 0.5% contaminants.

Also provided herein are methods of treating a mucopolysaccharidosis in a subject in need thereof, comprising administering intravenously an aqueous pharmaceutical formulation to the subject, wherein the formulation comprises substantially purified trehalose and a trehalase inhibitor as the sole active ingredients, wherein: the pH of the formulation is about 4.5 to 7.0; the formulation contains less than about 0.75 endotoxin units per mL; the formulation has an osmolality of about 280 mOsm/kg to 330 mOsm/kg; the formulation is administered over about 15 minutes to about 150 minutes; wherein the substantially purified trehalose is present in the formulation in an amount of about 5% (w/v) to about 15% (w/v); and wherein the substantially purified trehalose contains less than about 0.5% contaminants.

Also provided herein are methods of alleviating one or more symptoms of a mucopolysaccharidosis in a subject in need thereof, comprising administering intravenously an aqueous pharmaceutical formulation to the subject, wherein the formulation comprises substantially purified trehalose and a trehalase inhibitor as the sole active ingredients, wherein: the pH of the formulation is about 4.5 to 7.0; the formulation contains less than about 0.75 endotoxin units per mL; the formulation has an osmolality of about 280 mOsm/kg to 330 mOsm/kg; the formulation is administered over about 15 minutes to about 150 minutes; wherein the substantially purified trehalose is present in the formulation in an amount of about 5% (w/v) to about 15% (w/v); and wherein the substantially purified trehalose contains less than about 0.5% contaminants.

Also provided herein are methods of treating a mucopolysaccharidosis in a subject in need thereof, comprising (a) determining that the subject has a lysosomal enzyme deficiency; and (b) administering intravenously an aqueous pharmaceutical formulation to the subject, wherein the formulation comprises a single active ingredient consisting essentially of substantially purified trehalose, wherein: the pH of the formulation is about 4.5 to 7.0; the formulation contains less than about 0.75 endotoxin units per mL; the formulation has an osmolality of about 280 mOsm/kg to 330 mOsm/kg; the formulation is administered over about 15 minutes to about 150 minutes; wherein the substantially purified trehalose is present in the formulation in an amount of about 5% (w/v) to about 15% (w/v); and wherein the substantially purified trehalose contains less than about 0.5% contaminants.

Also provided herein are methods of alleviating one or more symptoms of a mucopolysaccharidosis in a subject in need thereof, comprising (a) determining that the subject has a lysosomal enzyme deficiency; and (b) administering intravenously an aqueous pharmaceutical formulation to the subject, wherein the formulation comprises a single active ingredient consisting essentially of substantially purified trehalose, wherein: the pH of the formulation is about 4.5 to 7.0; the formulation contains less than about 0.75 endotoxin units per mL; the formulation has an osmolality of about 280 mOsm/kg to 330 mOsm/kg; the formulation is administered over about 15 minutes to about 150 minutes; wherein the substantially purified trehalose is present in the formulation in an amount of about 5% (w/v) to about 15% (w/v); and wherein the substantially purified trehalose contains less than about 0.5% contaminants.

Also provided herein are methods of treating a mucopolysaccharidosis in a subject in need thereof, comprising (a) determining that the subject has a lysosomal enzyme deficiency; and (b) administering intravenously an aqueous pharmaceutical formulation to the subject, wherein the formulation comprises substantially purified trehalose and a trehalase inhibitor as the sole active ingredients, wherein: the pH of the formulation is about 4.5 to 7.0; the formulation contains less than about 0.75 endotoxin units per mL; the formulation has an osmolality of about 280 mOsm/kg to 330 mOsm/kg; the formulation is administered over about 15 minutes to about 150 minutes; wherein the substantially purified trehalose is present in the formulation in an amount of about 5% (w/v) to about 15% (w/v); and wherein the substantially purified trehalose contains less than about 0.5% contaminants.

Also provided herein are methods of alleviating one or more symptoms of a mucopolysaccharidosis in a subject in need thereof, comprising (a) determining that the subject has a lysosomal enzyme deficiency; and (b) administering intravenously an aqueous pharmaceutical formulation to the subject, wherein the formulation comprises substantially purified trehalose and a trehalase inhibitor as the sole active ingredients, wherein: the pH of the formulation is about 4.5 to 7.0; the formulation contains less than about 0.75 endotoxin units per mL; the formulation has an osmolality of about 280 mOsm/kg to 330 mOsm/kg; the formulation is administered over about 15 minutes to about 150 minutes; wherein the substantially purified trehalose is present in the formulation in an amount of about 5% (w/v) to about 15% (w/v); and wherein the substantially purified trehalose contains less than about 0.5% contaminants.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the invention will be apparent from the following detailed description and FIGURES, and from the claims.

DESCRIPTION OF DRAWINGS

FIG. 1 illustrates the different known MPSs, the gene and protein associated with each MPS, and the saccharide compound(s) that aggregates due to the dysregulation of the MPS-associated gene and/or MPS-associated protein.

DETAILED DESCRIPTION

Definitions

As used herein, the terms "treat" or "treatment," refer to therapeutic measures. Beneficial or desired clinical results include, but are not limited to, stabilized (i.e., not worsening) state of disease, delay or slowing of disease progression, and remission (whether partial or total), whether detectable or undetectable. "Treatment" can also mean prolonging survival as compared to expected survival if not receiving treatment. In some embodiments, treatment includes alleviation of one or more symptoms of a disease, as defined herein.

As used herein, "alleviate" or "alleviation," refer to reduction, in whole or in part, of symptoms associated with a disease or disorder or condition, diminishment of the extent of disease, and amelioration or palliation of the disease state (e.g., one or more symptoms of the disease).

As used herein, the term "MPS-associated," refers to nucleic acids (e.g., DNA or RNA) and/or proteins associated with a mucopolysaccharidosis, e.g., having a dysregulation of an MPS-associated gene, an MPS-associated protein, or the expression or activity or level of any of the same, leads to the development of a mucopolysaccharidosis. Non-limiting examples of MPS-associated genes include, for example, IDUA, IDS, SGSH, NAGLU, HGSNAT, GNS, GALNS, GLB1, ARSB, GUSB, and HYAL1. Non-limiting examples of MPS-associated proteins include, for example, α-L-iduronidase, iduronate sulfatase, heparan sulfamidase, N-acetylglucosaminidase, heparan-α-glucosaminide N-acetyltransferase, N-acetylglucosamine 6-sulfatase, galactose-6-sulfate sulfatase, β-galactosidase, N-acetylgalactosamine-4-sulfatase, β-glucuronidase, and hyaluronidase.

As used herein, the term "subject" refers to any animal, including mammals such as mice, rats, other rodents, rabbits, dogs, cats, swine, cattle, sheep, horses, primates, and humans. In some embodiments, the subject is a human. In some embodiments, the subject has experienced and/or exhibited at least one symptom of the disease or disorder to be treated and/or alleviated. In some embodiments, the subject has been identified or diagnosed as having an MPS with a dysregulation of an MPS-associated gene, an MPS-associated protein, or activity or level of any of the same (e.g., as determined using a regulatory agency-approved, e.g., FDA-approved, assay or kit). In some embodiments, the subject has a sample that is positive for a dysregulation of an MPS-associated gene, an MPS-associated protein, or activity or level of any of the same (e.g., as determined using a regulatory agency-approved assay or kit). In some embodiments, the subject is suspected of having an MPS. In some embodiments, the subject has a clinical record indicating that the subject has a sample that has a dysregulation of an MPS-associated gene, an MPS-associated protein, or activity or level of any of the same (and optionally the clinical record indicates that the subject should be treated with any of the compositions provided herein). In some embodiments, the subject is a pediatric subject.

The term "pediatric subject" as used herein refers to a subject under the age of 21 years at the time of diagnosis or treatment. The term "pediatric" can be further be divided into various subpopulations including: neonates (from birth through the first month of life); infants (1 month up to two years of age); children (two years of age up to 12 years of age); and adolescents (12 years of age through 21 years of age (up to, but not including, the twenty-second birthday)). Berhman R E, Kliegman R, Arvin A M, Nelson W E. Nelson *Textbook of Pediatrics,* 15th Ed. Philadelphia: W.B. Saunders Company, 1996; Rudolph A M, et al. *Rudolph's Pediatrics,* 21st Ed. New York: McGraw-Hill, 2002; and Avery M D, First L R. *Pediatric Medicine,* 2nd Ed. Baltimore: Williams & Wilkins; 1994. In some embodiments, a pediatric subject is from birth through the first 28 days of life, from 29 days of age to less than two years of age, from two years of age to less than 12 years of age, or 12 years of age through 21 years of age (up to, but not including, the twenty-second birthday). In some embodiments, a pediatric subject is from birth through the first 28 days of life, from 29 days of age to less than 1 year of age, from one month of age to less than four months of age, from three months of age to less than seven months of age, from six months of age to less than 1 year of age, from 1 year of age to less than 2 years of age, from 2 years of age to less than 3 years of age, from 2 years of age to less than seven years of age, from 3 years of age to less than 5 years of age, from 5 years of age to less than 10 years of age, from κ years of age to less than 13 years of age, from 10 years of age to less than 15 years of age, or from 15 years of age to less than 21 years of age.

The phrase "dysregulation of an MPS-associated gene, an MPS-associated protein, or the expression or activity or level of any of the same" refers to a genetic mutation. For example, a mutation in an IDUA gene that results in the expression of a α-L-iduronidase protein that includes a deletion of at least one amino acid as compared to a wild type α-L-iduronidase protein, a mutation in an IDUA gene that results in the expression of a α-L-iduronidase protein with one or more point mutations as compared to a wild type α-L-iduronidase protein, or a mutation in an IDUA gene that results in the expression of a α-L-iduronidase protein with at least one inserted amino acid as compared to a wild type α-L-iduronidase protein. Non-limiting examples of particular an MPS-associated protein point mutations/insertions/deletions are described in Table 1.

The term "wild type" describes a nucleic acid (e.g., a particular gene or mRNA, such as IDUA) or protein (e.g., an α-L-iduronidase protein) that is found in a subject that does not have an MPS (and optionally also does not have an increased risk of developing an MPS and/or is not suspected of having an MPS), or is found in a cell or tissue from a subject that does not have an MPS (and optionally also does not have an increased risk of developing an MPS and/or is not suspected of having an MPS).

The phrases "consisting essentially of" or "consisting of" exclude any element, step, or ingredient not specified, e.g., excluding materials other than those recited except for impurities ordinarily associated therewith.

The term "regulatory agency" refers to a country's agency for the approval of the medical use of pharmaceutical agents with the country. For example, a non-limiting example of a regulatory agency is the U.S. Food and Drug Administration (FDA).

Methods of Treatment

Some embodiments provide methods of treating a mucopolysaccharidosis in a subject in need thereof, comprising administering intravenously an aqueous pharmaceutical formulation to the subject, wherein the formulation comprises a single active ingredient consisting essentially of substantially purified trehalose, wherein:
  the pH of the formulation is about 4.5 to 7.0;
  the formulation contains less than about 0.75 endotoxin units per mL;
  the formulation has an osmolality of about 280 mOsm/kg to 330 mOsm/kg;
  the formulation is administered over about 15 minutes to about 150 minutes;
  wherein the substantially purified trehalose is present in the formulation in an amount of about 5% (w/v) to about 15% (w/v); and
  wherein the substantially purified trehalose contains less than about 0.5% contaminants.

Some embodiments provide methods of alleviating one or more symptoms of a mucopolysaccharidosis in a subject in need thereof, comprising administering intravenously an aqueous pharmaceutical formulation to the subject, wherein the formulation comprises a single active ingredient consisting essentially of substantially purified trehalose, wherein:
  the pH of the formulation is about 4.5 to 7.5;
  the formulation contains less than about 0.75 endotoxin units per mL;
  the formulation has an osmolality of about 280 mOsm/kg to 330 mOsm/kg;
  the formulation is administered over about 15 minutes to about 150 minutes;
  wherein the substantially purified trehalose is present in the formulation in an amount of about 5% (w/v) to about 15% (w/v); and
  wherein the substantially purified trehalose contains less than about 0.5% contaminants.

Some embodiments provide methods of treating a mucopolysaccharidosis in a subject in need thereof, comprising administering intravenously an aqueous pharmaceutical formulation to the subject, wherein the formulation comprises substantially purified trehalose and a trehalase inhibitor as the sole active ingredients, wherein:
  the pH of the formulation is about 4.5 to 7.0;
  the formulation contains less than about 0.75 endotoxin units per mL;
  the formulation has an osmolality of about 280 mOsm/kg to 330 mOsm/kg;
  the formulation is administered over about 15 minutes to about 150 minutes;
  wherein the substantially purified trehalose is present in the formulation in an amount of about 5% (w/v) to about 15% (w/v); and
  wherein the substantially purified trehalose contains less than about 0.5% contaminants.

Some embodiments provide methods of alleviating one or more symptoms of a mucopolysaccharidosis in a subject in need thereof, comprising administering intravenously an aqueous pharmaceutical formulation to the subject, wherein the formulation comprises substantially purified trehalose and a trehalase inhibitor as the sole active ingredients, wherein:
  the pH of the formulation is about 4.5 to 7.0;
  the formulation contains less than about 0.75 endotoxin units per mL;
  the formulation has an osmolality of about 280 mOsm/kg to 330 mOsm/kg;
  the formulation is administered over about 15 minutes to about 150 minutes;
  wherein the substantially purified trehalose is present in the formulation in an amount of about 5% (w/v) to about 15% (w/v); and wherein the substantially purified trehalose contains less than about 0.5% contaminants.

Some embodiments provide methods of treating a mucopolysaccharidosis in a subject in need thereof, comprising
(a) determining that the subject has a lysosomal enzyme deficiency; and
(b) administering intravenously an aqueous pharmaceutical formulation to the subject, wherein the formulation comprises a single active ingredient consisting essentially of substantially purified trehalose, wherein:
the pH of the formulation is about 4.5 to 7.0;
the formulation contains less than about 0.75 endotoxin units per mL;
the formulation has an osmolality of about 280 mOsm/kg to 330 mOsm/kg;
the formulation is administered over about 15 minutes to about 150 minutes;
wherein the substantially purified trehalose is present in the formulation in an amount of about 5% (w/v) to about 15% (w/v); and
wherein the substantially purified trehalose contains less than about 0.5% contaminants.

Some embodiments provide methods of alleviating one or more symptoms of a mucopolysaccharidosis in a subject in need thereof, comprising
(a) determining that the subject has a lysosomal enzyme deficiency; and
(b) administering intravenously an aqueous pharmaceutical formulation to the subject, wherein the formulation comprises a single active ingredient consisting essentially of substantially purified trehalose, wherein:
the pH of the formulation is about 4.5 to 7.0;
the formulation contains less than about 0.75 endotoxin units per mL;
the formulation has an osmolality of about 280 mOsm/kg to 330 mOsm/kg;
the formulation is administered over about 15 minutes to about 150 minutes;
wherein the substantially purified trehalose is present in the formulation in an amount of about 5% (w/v) to about 15% (w/v); and
wherein the substantially purified trehalose contains less than about 0.5% contaminants.

Some embodiments provide methods of treating a mucopolysaccharidosis in a subject in need thereof, comprising
(a) determining that the subject has a lysosomal enzyme deficiency; and
(b) administering intravenously an aqueous pharmaceutical formulation to the subject, wherein the formulation comprises substantially purified trehalose and a trehalase inhibitor as the sole active ingredients, wherein:
the pH of the formulation is about 4.5 to 7.0;
the formulation contains less than about 0.75 endotoxin units per mL;
the formulation has an osmolality of about 280 mOsm/kg to 330 mOsm/kg;
the formulation is administered over about 15 minutes to about 150 minutes;
wherein the substantially purified trehalose is present in the formulation in an amount of about 5% (w/v) to about 15% (w/v); and
wherein the substantially purified trehalose contains less than about 0.5% contaminants.

Some embodiments provide methods of alleviating one or more symptoms of a mucopolysaccharidosis in a subject in need thereof, comprising
(a) determining that the subject has a lysosomal enzyme deficiency; and
(b) administering intravenously an aqueous pharmaceutical formulation to the subject, wherein the formulation comprises substantially purified trehalose and a trehalase inhibitor as the sole active ingredients, wherein:
the pH of the formulation is about 4.5 to 7.0;
the formulation contains less than about 0.75 endotoxin units per mL;
the formulation has an osmolality of about 280 mOsm/kg to 330 mOsm/kg;
the formulation is administered over about 15 minutes to about 150 minutes;
wherein the substantially purified trehalose is present in the formulation in an amount of about 5% (w/v) to about 15% (w/v); and
wherein the substantially purified trehalose contains less than about 0.5% contaminants.

Some embodiments provide methods of treating a mucopolysaccharidosis in a subject in need thereof, comprising administering intravenously an aqueous pharmaceutical formulation to the subject, wherein the formulation comprises a single active ingredient consisting essentially of substantially purified trehalose, wherein: the pH of the formulation is about 5.0 to 6.0; the formulation contains less than about 0.25 endotoxin units per mL; the formulation has an osmolality of about 300 mOsm/kg to 310 mOsm/kg; the formulation is administered over about 15 minutes to about 60 minutes; wherein the substantially purified trehalose is present in the formulation in an amount of about 8% (w/v) to about 10% (w/v); and wherein the substantially purified trehalose contains less than about 0.5% contaminants. In some embodiments, the mucopolysaccharidosis is selected from: Sanfillippo syndrome A (MPS IIIA), Sanfillippo syndrome B (MPS IIIB), Sanfillippo syndrome C (MPS IIIC), and Sanfillippo syndrome D (MPS IIID). Other embodiments provide methods of alleviating one or more symptoms of a mucopolysaccharidosis in a subject in need thereof, comprising administering intravenously an aqueous pharmaceutical formulation to the subject, wherein the formulation comprises a single active ingredient consisting essentially of substantially purified trehalose, wherein: the pH of the formulation is about 5.0 to 6.0; the formulation contains less than about 0.25 endotoxin units per mL; the formulation has an osmolality of about 300 mOsm/kg to 310 mOsm/kg; the formulation is administered over about 15 minutes to about 60 minutes; wherein the substantially purified trehalose is present in the formulation in an amount of about 8% (w/v) to about 10% (w/v); and wherein the substantially purified trehalose contains less than about 0.5% contaminants. In some embodiments, the mucopolysaccharidosis is selected from: Sanfillippo syndrome A (MPS IIIA), Sanfillippo syndrome B (MPS IIIB), Sanfillippo syndrome C (MPS IIIC), and Sanfillippo syndrome D (MPS IIID).

In some embodiments, the pH of the formulation is about 4.5 to 7.0. In some embodiments, the pH of the formulation is about 4.5, about 4.8, about 5, about 5.3, about 5.5, about 5.8, about 6, about 6.3, about 6.5, about 6.8, about 7, or any value in between. In some embodiments, the pH of the formulation, is about 4.4 to about 6.6. In other embodiments, the pH of the formulation, is about 4.5 to about 6.5. In still other embodiments, the pH of the formulation is about 5 to about 6. In some embodiments, the pH of the formulation is about 5.5.

In some embodiments, the formulation contains less than about 0.75 endotoxin units per mL, e.g., between an undetectable level of endotoxin units per mL, up to about 0.75 endotoxin units per mL, such as about 0.05, about 0.10, about 0.15, about 0.20, about 0.25, about 0.30, about 0.35, about 0.40, about 0.45, about 0.50, about 0.55, about 0.60, about 0.65, or about 0.70 endotoxin units per mL. In some embodiments, the formulation contains than about 0.50 endotoxin units per mL. In other embodiments, the formulation contains than about 0.25 endotoxin units per mL. In still other embodiments, the formulation contains than about 0.20 endotoxin units per mL. In some embodiments, the formulation contains about 0.01 to about 0.15 endotoxin units per mL, or any value in between. In some embodiments, the formulation contains less than about 0.15 endotoxin units per mL. In other embodiments, the formulation contains less than about 0.10 endotoxin units per mL. In still other embodiments, the formulation contains less than about 0.05 endotoxin units per mL. In some embodiments, the formulation contains less than about 0.02 endotoxin units per mL. In other embodiments, the formulation contains less than about 0.01 endotoxin units per mL. In still other embodiments, the formulation contains an undetectable amount of endotoxin units per mL. Methods for detecting endotoxin levels are known in the art, and include, for example, the rabbit pyrogen test (USP <151>), the monocyte activation test, the limulus amoebocyte lysate assay, and HPLC-based methods.

In some embodiments, the formulation has an osmolality of about 290 mOsm/kg to 320 mOsm/kg, or any value in between, for example, about 290, about 295, about 300, about 305, about 310, about 315, or about 320 mOsm/kg. In other embodiments, the formulation has an osmolality of about 300 mOsm/kg to about 310 mOsm/kg. In some embodiments, the formulation has an osmolality of about 290 mOsm/kg, about 300 mOsm/kg, about 310 mOsm/kg, or about 320 mOsm/kg.

In some embodiments, the formulation is administered over about 15 minutes to about 150 minutes, or any value in between. In some embodiments, the formulation is administered over about 15 minutes to about 90 minutes. In other embodiments, the formulation is administered over about 15 minutes to about 60 minutes. In other embodiments, the formulation is administered over about 15 minutes to about 45 minutes. In some embodiments, the formulation is administered over about 15 minutes to about 30 minutes. In other embodiments, the formulation is administered over about 120 minutes to about 150 minutes. In some embodiments, the formulation is administered over less than about 150 minutes, less than about 120 minutes, less than about 90 minutes, less than about 60 minutes, less than about 45 minutes, or less than about 30 minutes.

In some embodiments, the formulation comprises about 5% (w/v) to about 15% (w/v) substantially purified trehalose, or any value in between, for example, about 5, about 6, about 7, about 8, about 9, about 10, about 11, about 12, about 13, about 14, or about 15% (w/v) substantially purified trehalose. In some embodiments, the formulation comprises about 6% (w/v) to about 12% (w/v) substantially purified trehalose. In other embodiments, the formulation comprises about 7% (w/v) to about 11% (w/v) substantially purified trehalose. In still other embodiments, the formulation comprises about 8% (w/v) to about 10% (w/v) substantially purified trehalose. In some embodiments, the formulation comprises about 9% (w/v) substantially purified trehalose. In other embodiments, the formulation comprises about 10% (w/v) substantially purified trehalose. In still other embodiments, the formulation comprises about 8% (w/v) substantially purified trehalose.

In some embodiments, the substantially purified trehalose contains less than about 0.5% contaminants, e.g., an undetectable level of contaminants by HPLC to about 0.5% contaminants, or any value in between. In some embodiments, the substantially purified trehalose contains about 0.01, about 0.02, about 0.03, about 0.04, about 0.05, about 0.08, about 0.10, about 0.12, about 0.15, about 0.18, about 0.20, about 0.22, about 0.25, about 0.28, about 0.30, about 0.32, about 0.35, about 0.38, about 0.40, about 0.42, about 0.45, about 0.48, or about 0.5% contaminants. In other embodiments, the substantially purified trehalose contains less than about 0.25% contaminants. In still other embodiments, the substantially purified trehalose contains less than about 0.1% contaminants. In some embodiments, the substantially purified trehalose contains less than about 0.08% contaminants. In other embodiments, the substantially purified trehalose contains less than about 0.05% contaminants. In still other embodiments, the substantially purified trehalose contains less than about 0.02% contaminants. In some embodiments, the substantially purified trehalose contains less than about 0.01% contaminants. In some embodiments, the contaminants in the substantially purified trehalose comprise glucose, maltotriose, or a combination thereof. In some embodiments, the formulation contains less than about 0.01% glucose and less than about 0.01% maltotriose.

In some embodiments, the subject is a pediatric subject. In other embodiments, the subject is under 18 years of age. In still other embodiments, the subject is under 12 years of age. In some embodiments, the subject is under 8 years of age. In other embodiments, the subject is under 6 years of age. In still other embodiments, the subject is under 4 years of age. In some embodiments, the subject is under 2 years of age. In other embodiments, the subject is under 1 year of age. In still other embodiments, the subject is under 8 months of age. In some embodiments, the subject is under 4 months of age. In other embodiments, the subject is under 1 month of age. In still other embodiments, the subject is 1 week of age. In some embodiments, the subject is between about 2 years of age and about 6 years of age. In other embodiments, the subject is about 4 years of age to about 6 years of age.

In some embodiments, the subject is in utero; and wherein the intravenous administration to the subject comprises intravenous administration to the mother.

Some embodiments described herein further comprise administering enzyme replacement therapy to the subject. In some embodiments, described herein, the subject has previously been administered enzyme replacement therapy. In some embodiments, the enzyme replacement therapy is selected from the group consisting of: Aldurazyme, Elaprase, Agalsidase α, Agalsidase β, Imiglucerase, Taliglucerase α, Velaglucerase α, Alglucerase, Sebelipase α, Laronidase, Idursulfase, Elosulfase α, Galsulfase, Alglucosidase α; and combinations of any of the foregoing.

Some embodiments described herein further comprise administering a substrate reduction therapy to the subject. In some embodiments, described herein, the subject has previously been administered a substrate reduction therapy. In some embodiments, the substrate reduction therapy comprises one or more of miglustat, migalastat, miglitol, eliglustat, genistein, (S)-quinuclidin-3-yl(2-(2-(4-fluorophenyl)thiazol-4-yl)propan-2-yl)carbamate (GZ161), quinuclidin-3-yl(2-(4'-fluoro-[1,1'-biphenyl]-3-yl)propan-2-yl)carbamate, ibiglustat, venglustat, eliglustat; or a combination of any of the foregoing; or a pharmaceutically acceptable salt of any of the foregoing.

In some embodiments, the formulation comprises substantially purified trehalose and a trehalase inhibitor as the sole active ingredients. In some embodiments, the trehalase inhibitor is selected from the group consisting of validimycin A, trehazolin, amygdalin; or a combination of any of the foregoing; or a pharmaceutically acceptable salt of any of the foregoing.

Some embodiments further comprise administering a trehalase inhibitor as a non-fixed combination with the pharmaceutical formulation comprising a single active ingredient consisting essentially of substantially purified trehalose. In some embodiments, the trehalase inhibitor is selected from the group consisting of validimycin A, trehazolin, amygdalin; or a combination of any of the foregoing; or a pharmaceutically acceptable salt of any of the foregoing. In some embodiments, the trehalase inhibitor is administered simultaneously or sequentially in either order with the pharmaceutical formulation comprising a single active ingredient consisting essentially of substantially purified trehalose.

Some embodiments provide a ready to use aqueous pharmaceutical formulation for intravenous administration to a subject, wherein the formulation comprises a single active ingredient consisting essentially of substantially purified trehalose, wherein: the pH of the formulation is about 4.5 to 7.0; the formulation contains less than about 0.75 endotoxin units per mL; the formulation has an osmolality of about 280 mOsm/kg to 330 mOsm/kg; wherein the substantially purified trehalose is present in the formulation in an amount of about 5% (w/v) to about 15% (w/v); wherein the substantially purified trehalose contains less than about 0.5% contaminants; wherein the formulation is disposed within a sealed container; and wherein the formulation is sterile.

In some embodiments, the container includes, but is not limited to, glass vials (for example, flint glass vials), ampoules, plastic flexible containers such as PVC (polyvinyl chloride) containers, VisiV™ plastic containers (Hospira, Inc., Lake Forest, Ill.), and CR3 elastomer copolyester ether containers (Hospira, Inc., Lake Forest, Ill.), CZ resin containers, and polypropylene containers. In some embodiments, the container is BPA-free.

In some embodiments, the container is selected form the group consisting of a glass container or a plastic container. In some embodiments, the container is a glass container. In other embodiments, the container is a plastic container. In some embodiments, the formulation is formulated as a total volume of 10 mL to 100 mL, or any value in between. In some embodiments, the formulation is formulated as a total volume selected from the group consisting of 10 mL, 20 mL, 30 mL, or 40 mL. In other embodiments, the formulation is formulated as a total volume of 10 mL. In still other embodiments, the formulation is formulated as a total volume of 20 mL. In some embodiments, the formulation is formulated as a total volume of 30 mL. In other embodiments, the formulation is formulated as a total volume of 40 mL.

In some embodiments, the plastic container is flexible. In some embodiments, the plastic container comprises a copolymer of ethylene and vinyl acetate. In other embodiments, the plastic container comprises a copolymer of an ethylene-propylene and a styrene-ethylene butylene-styrene (SEBS). In some embodiments, the plastic container comprises polypropylene. In some embodiments, the plastic container comprises single or multiple layers of polypropylene. In some embodiments, the plastic container is a film bag. In some embodiments, the plastic container further comprises an injection port and a tube port. In some embodiments, the formulation has been sterilized in moist steam. In other embodiments, the formulation has been aseptically sterilized.

In some embodiments, the formulations described herein are disposed in a container that can maintain the sterility of, or prevent the contamination of the formulation. In some embodiments, the container is a sealed container. In some embodiments, the formulation is disposed in a container, and formulated as a single use dosage. In other embodiments, the formulation is disposed in a container, and formulated as a multiple use dosage.

Accordingly, provided herein are methods for treating a subject diagnosed with (or identified as having) an that include administering to the subject a trehalose formulation as described herein Also provided herein are methods for treating a subject identified or diagnosed as having an MPS that include administering to the subject a formulation as described herein. In some embodiments, the subject that has been identified or diagnosed as having an MPS through the use of a regulatory agency-approved, e.g., FDA-approved test or assay for identifying dysregulation of a particular an MPS-associated gene or an MPS-associated protein, or activity or level same, in a subject or a sample from the subject or by performing any of the non-limiting examples of assays described herein. In some embodiments, the test or assay is provided as a kit. In other embodiments, the subject has been identified or diagnosed as having an MPS by measuring the levels of an aggregation product in a bodily fluid such as blood or urine.

Also provided are methods for treating an MPS in a subject in need thereof, the method comprising: (a) detecting a dysregulation of an MPS-associated gene and/or MPS-associated protein in the subject; and (b) administering to the subject a formulation as described herein. In some embodiments, the subject is determined to have an MPS through the use of a regulatory agency-approved, e.g., FDA-approved test or assay for identifying dysregulation of an MPS-associated gene, an MPS-associated protein, or expression or activity or level of any of the same, in a subject or in a sample from the subject or by performing any of the non-limiting examples of assays described herein. In some embodiments, the test or assay is provided as a kit Also provided are methods of treating a subject that include performing an assay on a sample obtained from the subject to determine whether the subject has a dysregulation of an MPS-associated gene, an MPS-associated protein, or expression or activity or level of any of the same, and administering (e.g., specifically or selectively administering) a trehalose formulation as described herein to the subject determined to have a dysregulation of an MPS-associated gene, an MPS-associated protein, or expression or activity or level of any of the same. Some embodiments of these methods further include administering to the subject another therapy such as enzyme replacement therapy or substrate reduction therapy, as described herein. In some embodiments, the subject is a subject suspected of having an MPS, a subject presenting with one or more symptoms of an MPS, or a subject having an elevated risk of developing an MPS. In some embodiments, the assay is a regulatory agency-approved assay, e.g., FDA-approved kit.

Also provided are trehalose formulations for use in treating an MPS in a subject identified or diagnosed as having an MPS through a step of performing an assay (e.g., an in vitro assay) on a sample obtained from the subject to determine whether the subject has a dysregulation of an MPS-associated gene, an MPS-associated protein, or expression or activity or level of any of the same, where the presence of a dysregulation of an MPS-associated gene, an MPS-associated protein, or expression or activity or level of any of the same, identifies that the subject has an MPS. Also provided is the use of the trehalose formulations described herein for the manufacture of a medicament for treating an MPS in a subject identified or diagnosed as having an MPS through a step of performing an assay on a sample obtained from the subject to determine whether the subject has a dysregulation of an MPS-associated gene, an MPS-associated protein, or expression or activity or level of any of the same where the presence of dysregulation of an MPS-associated gene, an MPS-associated protein, or expression or activity or level of any of the same, identifies that the subject has an MPS. Some embodiments of any of the methods or uses described herein further include recording in the subject's clinical record (e.g., a computer readable medium) that the subject is determined to have a dysregulation of an MPS-associated gene, an MPS-associated protein, or expression or activity or level of any of the same, through the performance of the assay, should be administered a the trehalose formulations described herein. In some embodiments, the assay is a regulatory agency-approved assay, e.g., FDA-approved kit.

Also provided is a the trehalose formulations described herein for use in the treatment of an MPS in a subject in need thereof or a subject identified or diagnosed as having an MPS. Also provided is the use of the trehalose formulations described herein for the manufacture of a medicament for treating an MPS in a subject identified or diagnosed as having an MPS. In some embodiments, a subject is identified or diagnosed as having an MPS through the use of a regulatory agency-approved, e.g., FDA-approved, kit for identifying dysregulation of an MPS-associated gene, an MPS-associated protein, or expression or activity or level of any of the same, in a subject or a sample from the subject.

Also provided herein are methods for treating a pediatric subject diagnosed with (or identified as having) an MPS that include administering to the pediatric subject a the trehalose formulations described herein. Also provided herein are methods for treating a pediatric subject identified or diagnosed as having an MPS that include administering to the pediatric subject a the trehalose formulations described herein. In some embodiments, the pediatric subject that has been identified or diagnosed as having an MPS through the use of a regulatory agency-approved, e.g., FDA-approved test or assay for identifying dysregulation of an MPS-associated gene, an MPS-associated protein, or expression or activity or level of any of the same, in a pediatric subject or a sample from the pediatric subject or by performing any of the non-limiting examples of assays described herein. In some embodiments, the test or assay is provided as a kit.

Also provided are methods for treating a lysosomal storage disorder in a pediatric subject in need thereof, the method comprising: (a) determining if the lysosomal storage disorder in the pediatric subject is an MPS; and (b) if the lysosomal storage disorder is determined to be an MPS, administering to the pediatric subject a the trehalose formulations described herein. Some embodiments of these methods further include administering to the subject another therapy such as enzyme replacement therapy or substrate reduction therapy. In some embodiments, the subject was previously treated with an enzyme replacement therapy (e.g., Aldurazyme, Elaprase, Agalsidase α, Agalsidase β, Imiglucerase, Taliglucerase α, Velaglucerase α, Alglucerase, Sebelipase α, Laronidase, Idursulfase, Elosulfase α, Galsulfase, Alglucosidase α) and/or a substrate reduction therapy (e.g., miglustat, migalastat, miglitol, eliglustat, genistein, (S)-quinuclidin-3-yl(2-(2-(4-fluorophenyl)thiazol-4-yl)propan-2-yl)carbamate (GZ161), quinuclidin-3-yl(2-(4'-fluoro-[1,1'-biphenyl]-3-yl)propan-2-yl)carbamate, ibiglustat, venglustat, eliglustat; or a combination of any of the foregoing; or a pharmaceutically acceptable salt of any of the foregoing).

In some embodiments, the pediatric subject is determined to have an MPS through the use of a regulatory agency-approved, e.g., FDA-approved test or assay for identifying dysregulation of an MPS-associated gene, an MPS-associated protein, or expression or activity or level of any of the same, in a pediatric subject or a sample from the pediatric subject or by performing any of the non-limiting examples of assays described herein. In some embodiments, the test or assay is provided as a kit.

Also provided are methods of treating a pediatric subject that include performing an assay on a sample obtained from the pediatric subject to determine whether the pediatric subject has a dysregulation of an MPS-associated gene, an MPS-associated protein, or expression or activity or level of any of the same, and administering (e.g., specifically or selectively administering) a the trehalose formulations described herein to the pediatric subject determined to have a dysregulation of an MPS-associated gene, an MPS-associated protein, or expression or activity or level of any of the same. Some embodiments of these methods further include administering to the pediatric subject another therapy such as enzyme replacement therapy or substrate reduction therapy. In some embodiments, the pediatric subject was previously treated with an enzyme replacement therapy (e.g., Aldurazyme, Elaprase, Agalsidase α, Agalsidase β, Imiglucerase, Taliglucerase α, Velaglucerase α, Alglucerase, Sebelipase α, Laronidase, Idursulfase, Elosulfase α, Galsulfase, Alglucosidase α) and/or a substrate reduction therapy (e.g., miglustat, migalastat, miglitol, eliglustat, genistein, (S)-quinuclidin-3-yl(2-(2-(4-fluorophenyl)thiazol-4-yl)propan-2-yl)carbamate (GZ161), quinuclidin-3-yl(2-(4'-fluoro-[1,1'-biphenyl]-3-yl)propan-2-yl)carbamate, ibiglustat, venglustat, eliglustat; or a combination of any of the foregoing; or a pharmaceutically acceptable salt of any of the foregoing). In some embodiments, the pediatric subject is a pediatric subject suspected of having an MPS, a pediatric subject presenting with one or more symptoms of an MPS, or a pediatric subject having an elevated risk of developing an MPS. In some embodiments, the assay is a regulatory agency-approved assay, e.g., FDA-approved kit. Additional assays are also known in the art.

Also provided is a the trehalose formulations described herein for use in treating an MPS in a pediatric subject identified or diagnosed as having an MPS through a step of performing an assay (e.g., an in vitro assay) on a sample obtained from the pediatric subject to determine whether the pediatric subject has a dysregulation of an MPS-associated gene, an MPS-associated protein, or expression or activity or level of any of the same, where the presence of a dysregulation of an MPS-associated gene, an MPS-associated protein, or expression or activity or level of any of the same, identifies that the pediatric subject has an MPS. Also provided is the use of a the trehalose formulations described herein for the manufacture of a medicament for treating an MPS in a pediatric subject identified or diagnosed as having an MPS through a step of performing an assay on a sample obtained from the pediatric subject to determine whether the pediatric subject has a dysregulation of an MPS-associated gene, an MPS-associated protein, or expression or activity or level of any of the same where the presence of dysregulation of an MPS-associated gene, an MPS-associated protein, or expression or activity or level of any of the same, identifies that the pediatric subject has an MPS. Some embodiments of any of the methods or uses described herein further include recording in the pediatric subject's clinical record (e.g., a computer readable medium) that the pediatric subject is determined to have a dysregulation of an MPS-associated gene, an MPS-associated protein, or expression or activity or level of any of the same, through the performance of the assay, should be administered a the trehalose formulations described herein. In some embodiments, the assay is a regulatory agency-approved assay, e.g., FDA-approved kit.

Also provided is a the trehalose formulations described herein for use in the treatment of an MPS in a pediatric subject in need thereof or a pediatric subject identified or diagnosed as having an MPS. Also provided is the use of a the trehalose formulations described herein for the manufacture of a medicament for treating an MPS in a pediatric subject identified or diagnosed as having an MPS. In some embodiments, a pediatric subject is identified or diagnosed as having an MPS through the use of a regulatory agency-approved, e.g., FDA-approved, kit for identifying dysregulation of an MPS-associated gene, an MPS-associated protein, or expression or activity or level of any of the same, in a pediatric subject or a sample from the pediatric subject.

In some embodiments of any of the methods or uses described herein, the subject has been identified or diagnosed as having an MPS with a dysregulation of an MPS-associated gene, an MPS-associated protein, or expression or activity or level of any of the same. In some embodiments of any of the methods or uses described herein, the subject has a sample that is positive for a dysregulation of an MPS-associated gene, an MPS-associated protein, or expression or activity or level of any of the same. In some embodiments of any of the methods or uses described herein, the subject can be a subject having a sample that is positive for a dysregulation of an MPS-associated gene, an MPS-associated protein, or expression or activity or level of any of the same. In some embodiments of any of the methods or uses described herein, the subject can be a subject having a dysregulation of an MPS-associated gene, an MPS-associated protein, or expression or activity or level of any of the same. In some embodiments of any of the methods or uses described herein, the subject is suspected of having an MPS (e.g., having one or more mutations in an MPS-associated gene and/or MPS-associated protein, as described herein). In some embodiments, provided herein are methods for treating an MPS in a subject in need of such treatment, the method comprising a) detecting a dysregulation of an MPS-associated gene, an MPS-associated protein, or the expression or activity or level of any of the same in a sample from the subject; and b) administering a the trehalose formulations described herein. In some embodiments, the dysregulation of an MPS-associated gene, an MPS-associated protein, or the expression or activity or level of any of the same includes one or more protein point mutations/insertions/deletions. Non-limiting examples of protein point mutations/insertions/deletions are described in Table 1. In some embodiments, the point mutations/insertions/deletions are selected from the group consisting of those protein mutations described in Table 1.

TABLE 1

| IDUA Mutations | References |
|---|---|
| Amino acid position 51 (e.g., Gly51Asp) | Venturi et al., *Hum. Mutat.*, 20(3): 231 (2002). |
| Amino acid position 75 (e.g., Ala75Thr) | Clarke et al., *Univ. of Wash.*, (2002). |
| Amino acid position 89 (e.g., Arg89Trp) | Bunge et al., *Hum. Mutat.*, 6(1): 91-4 (1995). |
| Amino acid position 218 (e.g., Leu218Pro) | Bunge et al., *Hum. Mutat.*, 6(1): 91-4 (1995). |
| Amino acid position 327 (e.g., Ala327Pro) | Scott et al., *Am. J. Hum. Genet.*, 53(5): 973-86 (1993). |
| Amino acid position 343 (e.g., Tyr343Ter) | Clarke et al., *Univ. of Wash.*, (2002). |
| Amino acid position 388 (e.g., Thr388Lys) | Kwak et al., *BMC Med. Genet.*, 17(1): 58 (2016). |
| Amino acid position 402 (e.g., Trp402Ter) | Scott et al., *Am. J. Hum. Genet.*, 53(5): 973-86 (1993). |
| Amino acid position 490 (e.g., Leu490Pro) | Tieu et al., *Hum. Mutat.*, 6(1): 55-9 (1995). |
| Amino acid position 492 (e.g., Arg492Pro) | Tieu et al., *Hum. Mutat.*, 6(1): 55-9 (1995). |
| Amino acid position 533 (e.g., Pro533Arg) | Richard et al., *Genet. Med.*, 17(5): 405-24 (2015). |
| Amino acid position 600 (e.g., Ser600Terfs) | Pollard et al., J. Inherit Metab. Dis., 36(2): 179-87 (2013). |
| Amino acid position 619 (e.g., Arg619Gly) | Lee-Chen et al., *J. Med. Genet.*, 34(11): 939-41 (1997). |
| Amino acid position 654 (e.g., Ter654Gly) | Bach et al., *Am. J. Hum. Genet.*, 53(2): 330-8 (1993). |
| IDS Mutations | Reference |
| Amino acid position 8 (e.g., Arg8Trpfs) | Amartino et al., *Mol. Genet. Metab. Rep.*, 1: 410-6 (2014). |
| Amino acid position 45 (e.g., Asp45His) | Alcantara-Ortigoza et al., *Clin. Genet.*, 89(5): 574-83 (2016). |
| Amino acid position 61 (e.g., Ser61Pro) | Amartino et al., *Mol. Genet. Metab. Rep.*, 1: 410-6 (2014). |
| Amino acid position 85 (e.g., Ala85Thr) | Amartino et al., *Mol. Genet. Metab. Rep.*, 1: 410-6 (2014). |
| Amino acid position 88 (e.g., Arg88Cys) | Demydchuk et al., *Nat. Commun's.*, 8: 15786 (2017). |
| Amino acid position 120 (e.g., Pro120His) | Amartino et al., *Mol. Genet. Metab. Rep.*, 1: 410-6 (2014). |
| Amino acid position 134 (e.g., Gly134Glu) | Amartino et al., *Mol. Genet. Metab. Rep.*, 1: 410-6 (2014). |
| Amino acid position 135 (e.g., Lys135Arg) | Bunge et al., *Hum. Mol. Genet.*, 1(5): 335-9 (1992). |
| Amino acid position 138 (e.g., His138Thrfs) | Amartino et al., *Mol. Genet. Metab. Rep.*, 1: 410-6 (2014). |
| Amino acid position 142 (e.g., Ser142Tyr) | Amartino et al., *Mol. Genet. Metab. Rep.*, 1: 410-6 (2014). |
| Amino acid position 155 (e.g., Phe155Profs) | Alcantara-Ortigoza et al., *Clin. Genet.*, 89(5): 574-83 (2016). |
| Amino acid position 157 (e.g., Pro157Ser) | Amartino et al., *Mol. Genet. Metab. Rep.*, 1: 410-6 (2014). |
| Amino acid position 160 (e.g., Pro160Arg) | Flomen et al., *Genomics*, 13(3): 543-50 (1992). |
| Amino acid position 170 (e.g., Thr170Metfs) | Bunge et al., *Hum. Mol. Genet.*, 1(5): 335-9 (1992). |
| Amino acid position 172 (e.g., Arg172Ter) | Flomen et al., *Genomics*, 13(3): 543-50 (1992). |
| Amino acid position 196 (e.g., Leu196Ser) | Van Goor et al., *J. Cyst Fibros.*, 13(1): 29-36 (2014). |

TABLE 1-continued

| | |
|---|---|
| Amino acid position 198 (e.g., Asp198Asn) | Amartino et al., *Mol. Genet. Metab. Rep.*, 1: 410-6 (2014). |
| Amino acid position 228 (e.g., Pro228Gln) | Amartino et al., *Mol. Genet. Metab. Rep.*, 1: 410-6 (2014). |
| Amino acid position 234 (e.g., Tyr234Ter) | Li et al., *J. Inherit Metab. Dis.*, 19(1): 93-4 (1996). |
| Amino acid position 252 (e.g., Asp252Terfs) | Alcantara-Ortigoza et al., *Clin. Genet.*, 89(5): 574-83 (2016). |
| Amino acid position 274 (e.g., Glu274Ter) | Amartino et al., *Mol. Genet. Metab. Rep.*, 1: 410-6 (2014). |
| Amino acid position 295 (e.g., Lys295Ile) | Amartino et al., *Mol. Genet. Metab. Rep.*, 1: 410-6 (2014). |
| Amino acid position 303 (e.g., Ser303Cysfs) | Amartino et al., *Mol. Genet. Metab. Rep.*, 1: 410-6 (2014). |
| Amino acid position 312 (e.g., Gly312Asp) | Amartino et al., *Mol. Genet. Metab. Rep.*, 1: 410-6 (2014). |
| Amino acid position 333 (e.g., Ser333Leu) | Amartino et al., *Mol. Genet. Metab. Rep.*, 1: 410-6 (2014). |
| Amino acid position 335 (e.g., His335Tyr) | Alcantara-Ortigoza et al., *Clin. Genet.*, 89(5): 574-83 (2016). |
| Amino acid position 336 (e.g., Gly336Trp) | Alcantara-Ortigoza et al., *Clin. Genet.*, 89(5): 574-83 (2016). |
| Amino acid position 339 (e.g., Leu339Pro) | Amartino et al., *Mol. Genet. Metab. Rep.*, 1: 410-6 (2014). |
| Amino acid position 342 (e.g., His342Pro) | Alcantara-Ortigoza et al., *Clin. Genet.*, 89(5): 574-83 (2016). |
| Amino acid position 345 (e.g., Trp345Arg) | Amartino et al., *Mol. Genet. Metab. Rep.*, 1: 410-6 (2014). |
| Amino acid position 367 (e.g., Thr367Ser) | |
| Amino acid position 369 (e.g., Ser369Ter) | Nykamp et al., *Genet. Med.*, 19(10): 1105-1117 (2017). |
| Amino acid position 374 (e.g., Gly374=) | Amartino et al., *Mol. Genet. Metab. Rep.*, 1: 410-6 (2014). |
| Amino acid position 378 (e.g., Phe378Profs) | Alcantara-Ortigoza et al., *Clin. Genet.*, 89(5): 574-83 (2016). |
| Amino acid position 422 (e.g., Cys422Gly) | Bunge et al., *Hum. Mol. Genet.*, 1(5): 335-9 (1992). |
| Amino acid position 443 (e.g., Arg443Ter) | Bunge et al., *Hum. Mol. Genet.*, 1(5): 335-9 (1992). |
| Amino acid position 465 (e.g., Gln465Ter) | Amartino et al., *Mol. Genet. Metab. Rep.*, 1: 410-6 (2014). |
| Amino acid position 468 (e.g., Arg468Gln) | Van Goor et al., *J. Cyst Fibros.*, 13(1): 29-36 (2014). |
| Amino acid position 468 (e.g., Arg468Leu) | Hopwood et al., *Hum Mutat.*, 2(6): 435-42 (1993). |
| Amino acid position 468 (e.g., Arg468Pro) | Amartino et al., *Mol. Genet. Metab. Rep.*, 1: 410-6 (2014). |
| Amino acid position 468 (e.g., Arg468Trp) | Crotty et al., *Hum. Mol. Genet.*, December; 1(9): 755-7 (1992). |
| Amino acid position 475 (e.g., Trp475Ter) | Amartino et al., *Mol. Genet. Metab. Rep.*, 1: 410-6 (2014). |
| Amino acid position 478 (e.g., Asp478Gly) | Amartino et al., *Mol. Genet. Metab. Rep.*, 1: 410-6 (2014). |
| Amino acid position 488 (e.g., Met488Argfs) | Alcantara-Ortigoza et al., *Clin. Genet.*, 89(5): 574-83 (2016). |
| Amino acid position 502 (e.g., Trp502Ser) | Flomen et al., *Genomics*, 13(3): 543-50 (1992). |
| Amino acid position 503 (e.g., Val503Asp) | Amartino et al., *Mol. Genet. Metab. Rep.*, 1: 410-6 (2014). |
| SGSH Mutations | Reference |
| Amino acid position 7 (e.g., Arg74Cys) | Van Goor et al., *J. Cyst Fibros.*, 13(1): 29-36 (2014). |
| Amino acid position 66 (e.g., Ser66Trp) | Di Natale et al., *Clin, Genet.*, 63(4): 314-8 (2003). |
| Amino acid position 74 (e.g., Arg74His) | Bunge et al., *Hum. Mutat.*, 10(6): 479-85 (1997).. |
| Amino acid position 90 (e.g., Gly90Arg) | Heron et al., *Am. J. Med. Genet. A.*, 155A(1): 58-68 (2011). |
| Amino acid position 122 (e.g., Gly122Arg) | Di Natale et al., *Clin, Genet.*, 63(4): 314-8 (2003). |
| Amino acid position 126 (e.g., Val126Glyfs) | Weber et al., *Hum. Mol. Genet.*, 6(9): 1573-9 (1997). |
| Amino acid position 128 (e.g., Pro128Leu) | Di Natale et al., *Clin, Genet.*, 63(4): 314-8 (2003). |
| Amino acid position 150 (e.g., Arg150Gln) | Di Natale et al., *Clin, Genet.*, 63(4): 314-8 (2003). |
| Amino acid position 191 (e.g., Gly191Arg) | Muschol et al., *Hum. Mutat.*, 23(6): 559-66 (2004). |
| Amino acid position 194 (e.g., Cys194Ter) | Pollard et al., *J. Inherit Metab. Dis.*, 36(2): 179-87 (2013). |
| Amino acid position 206 (e.g., Arg206Pro) | Gabrielli et al., *Am. J. Med. Genet A.*, 133A(1): 85-9 (2005). |
| Amino acid position 210 (e.g., Trp210Ter) | Weber et al., *Hum. Mol. Genet.*, 6(9): 1573-9 (1997). |
| Amino acid position 225 (e.g., Phe225Leu) | Heron et al., *Am. J. Med. Genet. A.*, 155A(1): 58-68 (2011). |
| Amino acid position 233 (e.g., Arg233Ter) | Beesley et al., *J. Med. Genet.*, 37(9): 704-7 (2000). |
| Amino acid position 235 (e.g., Asp235Asn) | Heron et al., *Am. J. Med. Genet. A.*, 155A(1): 58-68 (2011). |
| Amino acid position 245 (e.g., Arg245His) | Van Hove et al., *Am. J. Med. Genet. A.*, 118A(4): 382-7 (2003). |
| Amino acid position 293 (e.g., Pro293Ser) | Richards et al., *Genet. Med.*, 17(5): 405-24 (2015). |
| Amino acid position 298 (e.g., Ser298Pro) | Pollard et al., *J. Inherit Metab. Dis.*, 36(2): 179-87 (2013). |
| Amino acid position 304 (e.g., Arg304Leu) | Di Natale et al., *Clin, Genet.*, 63(4): 314-8 (2003). |
| Amino acid position 343 (e.g., Leu343Profs) | Pollard et al., *J. Inherit Metab. Dis.*, 36(2): 179-87 (2013). |
| Amino acid position 361 (e.g., Val361Serfs) | Pollard et al., *J. Inherit Metab. Dis.*, 36(2): 179-87 (2013). |
| Amino acid position 369 (e.g., Glu369Lys) | Di Natale et al., *Clin, Genet.*, 63(4): 314-8 (2003). |
| Amino acid position 379 (e.g., Val379Cysfs) | Weber et al., *Hum. Mol. Genet.*, 6(9): 1573-9 (1997). |
| Amino acid position 380 (e.g., Gln380Arg) | Weber et al., *Hum. Mol. Genet.*, 6(9): 1573-9 (1997). |
| Amino acid position 389 (e.g., Asn389Lys) | Bunge et al., *Hum. Mutat.*, 10(6): 479-85 (1997).. |
| Amino acid position 389 (e.g., Asn389Ser) | Pollard et al., *J. Inherit Metab. Dis.*, 36(2): 179-87 (2013). |
| Amino acid position 424 (e.g., Tyr424Terfs) | Weber et al., *Hum. Mol. Genet.*, 6(9): 1573-9 (1997). |
| Amino acid position 433 (e.g., Arg433Gln) | Van Goor et al., *J. Cyst Fibros.*, 13(1): 29-36 (2014). |
| Amino acid position 433 (e.g., Arg433Trp) | Richards et al., *Genet. Med.*, 17(5): 405-24 (2015). |
| Amino acid position 447 (e.g., Glu447Lys) | Van Hove et al., *Am. J. Med. Genet. A.*, 118A(4): 382-7 (2003). |

TABLE 1-continued

| | |
|---|---|
| Amino acid position 477 (e.g., Asp477Thrfs) | Pollard et al., *J. Inherit Metab. Dis.*, 36(2): 179-87 (2013). |

| NAGLU Mutations | Reference |
|---|---|
| Amino acid position 48 (e.g., Phe48Leu) | Yogalingam et al., Biochim Biophys Acta., 1502(3): 415-25 (2000). |
| Amino acid position 65 (e.g., Tyr65Thrfs) | Coll et al., *J Inherit Metab Dis.*, 24(1): 83-4 (2001). |
| Amino acid position 74 (e.g., Arg74Profs) | Beesley et al., *J. Med. Genet.*, 35(11): 910-4 (1998). |
| Amino acid position 74 (e.g., Arg74Profs) | Coll et al., *J. Inherit Metab. Dis.*, 24(1): 83-4 (2001). |
| Amino acid position 75 (e.g., Val75Argfs) | Tessitore et al., *Hum Genet.*, 107(6): 568-76 (2000). |
| Amino acid position 115 (e.g., Pro115Ser) | Schmidtchen et al., *Am. J. Hum. Genet.*, 62(1): 64-9 (1998). |
| Amino acid position 120 (e.g., Glu120Ter) | Piotrowska et al., *Acta Paediatr.*, 98(4): 743-9 (2009). |
| Amino acid position 140 (e.g., Tyr140Cys) | Beesley et al., *J. Med. Genet.*, 35(11): 910-4 (1998). |
| Amino acid position 160 (e.g., Asn160Lysfs) | Yassaee et al., Clin Chim Acta. 2017 November; 474: 88-95. |
| Amino acid position 168 (e.g., Trp168Ter) | Coll et al., *J. Inherit Metab. Dis.*, 24(1): 83-4 (2001). |
| Amino acid position 169 (e.g., Ser169Argfs) | Zhao et al., *Proc. Natl. Acad. Sci. USA.*, 93(12): 6101-5 (1996). |
| Amino acid position 234 (e.g., Arg234Cys) | Beesley et al., *J. Med. Genet.*, 35(11): 910-4 (1998). |
| Amino acid position 290 (e.g., Ile290Serfs) | Tang et al., *Clin. Chim. Acta.*, 419: 33-8 (2013). |
| Amino acid position 292 (e.g., Gly292Arg) | Tang et al., *Clin. Chim. Acta.*, 419: 33-8 (2013). |
| Amino acid position 296 (e.g., Leu296Cysfs) | Heron et al., *Am. J. Med. Genet. A.*, 155A(1): 58-68 (2011). |
| Amino acid position 297 (e.g., Arg297Ter) | Beesley et al., *J. Med. Genet.*, 35(11): 910-4 (1998). |
| Amino acid position 314 (e.g., Phe314Leu) | Tanaka et al., *J. Hum. Genet.*, 47(9): 484-7 (2002). |
| Amino acid position 336 (e.g., Glu336Ter) | Tessitore et al., *Hum Genet.*, 107(6): 568-76 (2000). |
| Amino acid position 403 (e.g., Ile403Thr) | Tetreault et al., *Brain*, 138(Pt 6): 1477-83 (2015). |
| Amino acid position 404 (e.g., Trp404Ter) | Bunge et al., *J. Med. Genet.*, 36(1): 28-31 (1999). |
| Amino acid position 414 (e.g., His414Arg) | Pollard et al., *J Inherit Metab Dis.*, 36(2): 179-87 (2013). |
| Amino acid position 482 (e.g., Arg482Trp) | Tanaka et al., *J. Hum. Genet.*, 47(9): 484-7 (2002). |
| Amino acid position 520 (e.g., Arg520Trp) | Tessitore et al., *Hum Genet.*, 107(6): 568-76 (2000). |
| Amino acid position 533 (e.g., Arg533Ter) | Mangas et al., *Clin, Genet.*, 73(3): 251-6 (2008). |
| Amino acid position 558 (e.g., Tyr558Ter) | Ouesleti et al., *Clin Chim Acta.*, 412(23-24): 2326-31 (2011). |
| Amino acid position 565 (e.g., Arg565Gln) | Tang et al., *Clin. Chim. Acta.*, 419: 33-8 (2013). |
| Amino acid position 565 (e.g., Arg565Pro) | Tanaka et al., *J. Hum. Genet.*, 47(9): 484-7 (2002). |
| Amino acid position 565 (e.g., Arg565Trp) | Beesley et al., *J. Med. Genet.*, 35(11): 910-4 (1998). |
| Amino acid position 604 (e.g., Pro604Leu) | Ouesleti et al., *Clin Chim Acta.*, 412(23-24): 2326-31 (2011). |
| Amino acid position 612 (e.g., Ser612Gly) | Nycamp et al., Genet Med. 2017 October; 19(10): 1105-1117. |
| Amino acid position 626 (e.g., Arg626Ter) | Zhao et al., *Proc. Natl. Acad. Sci. USA.*, 93(12): 6101-5 (1996). |
| Amino acid position 639 (e.g., Glu639Ter) | Beesley et al., *J. Med. Genet.*, 35(11): 910-4 (1998). |
| Amino acid position 643 (e.g., Arg643Cys) | Weber et al., *Eur. J. Hum. Genet.*, 7(1): 34-44 (1999). |
| Amino acid position 649 (e.g., Trp649Valfs) | Yassaee et al., *Clin. Chim. Acta..*, 474: 88-95 (2017). |
| Amino acid position 650 (e.g., Gly650Glu) | Pollard et al., *J. Inherit Metab Dis.*, 36(2): 179-87 (2013). |
| Amino acid position 664 (e.g., Ala664Val) | Heron et al., *Am. J. Med. Genet. A.*, 155A(1): 58-68 (2011). |
| Amino acid position 674 (e.g., Arg674Cys) | Pollard et al., *J Inherit Metab Dis.*, 36(2): 179-87 (2013). |
| Amino acid position 674 (e.g., Arg674His) | Beesley et al., *J. Med. Genet.*, 35(11): 910-4 (1998). |
| Amino acid position 706 (e.g., Gln706Ter) | Zhao et al., *Am. J. Hum. Genet.*, January; 62(1): 53-63 (1998). |

| HSGNAT Mutations | Reference |
|---|---|
| Amino acid position 133 (e.g., Gly133Ala) | Haer-Wigman et al., *Hum. Mol. Genet.*, 24(13): 3742-51 (2015). |
| Amino acid position 176 (e.g., Val176Cysfs) | Coutinho et al., *Clin. Genet.*, 74(2): 194-5 (2008). |
| Amino acid position 203 (e.g., Arg203Ter) | Nykamk et al., *Genet. Med.*, 19(10): 1105-1117 (2017). |
| Amino acid position 283 (e.g., Pro283Leu) | Richards et al., *Genet. Med.*, 17(5): 405-24 (2015). |
| Amino acid position 316 (e.g., Arg344His) | Hrebicek et al., *Am. J. Hum. Genet.*, 79(5): 807-19 (2006). |
| Amino acid position 344 (e.g., Arg344Cys) | Feldhammer et al., *Hum. Mutat.*, 30(6): 918-25 (2009). |
| Amino acid position 384 (e.g., Arg384Ter) | Hrebicek et al., *Am. J. Hum. Genet.*, 79(5): 807-19 (2006). |
| Amino acid position 454 (e.g., Gln454Ter) | Velasco et al., *J. Child Neurol.*, 32(2): 177-183 (2017). |
| Amino acid position 471 (e.g., Glu471Lys) | Feldhammer et al., *Hum. Mutat.*, 30(6): 918-25 (2009). |
| Amino acid position 482 (e.g., Met482Lys) | Hrebicek et al., *Am. J. Hum. Genet.*, 79(5): 807-19 (2006). |

TABLE 1-continued

| | |
|---|---|
| Amino acid position 506 (e.g., Arg506Ter) | Hrebicek et al., *Am. J. Hum. Genet.*, 79(5): 807-19 (2006). |
| Amino acid position 518 (e.g., Ser518Phe) | Feldhammer et al., *Hum. Mutat.*, 30(6): 918-25 (2009). |
| Amino acid position 545 (e.g., Thr545Lys) | Feldhammer et al., *Hum. Mutat.*, 30(6): 918-25 (2009). |
| Amino acid position 558 (e.g., Trp558Ter) | Feldhammer et al., *Hum. Mutat.*, 30(6): 918-25 (2009). |

| GNS Mutations | Reference |
|---|---|
| Amino acid position 354 (e.g., Arg355Ter) | Kresse et al., *Proc. Natl. Acad. Sci. USA.*, 77(11): 6822-6 (1980). |
| Amino acid position 380 (e.g., Asp380Glyfs) | Jansen et al., *Arch. Neurol.*, 64(11): 1629-34 (2007). |
| Amino acid position 390 (e.g., Gln390Argfs) | Beesley et al., *J. Med. Genet.*, 40(3): 192-4 (2003). |
| Amino acid position 390 (e.g., Gln390Ter) | Kaplan et al., *J. Pediatr.*, 110(2): 267-71 (1987). |
| Amino acid position 410 (e.g., Ser410Ilefs) | Elcioglu et al., *Genet. Couns.*, 20(2): 133-9 (2009). |

| GALNS Mutations | Reference |
|---|---|
| Amino acid position 16 (e.g., Val16Glu) | Tomatsu et al., *Hum. Mutat.*, 10(5): 368-75 (1997). |
| Amino acid position 36 (e.g., Leu36Arg) | Morrone et al., *Mol. Genet. Metab.*, 112(2): 160-70 (2014). |
| Amino acid position 41 (e.g., Met41Lys) | Wraith, *Arch. Dis. Child.*, 72(3): 263-7 (1995). |
| Amino acid position 60 (e.g., Asp60Asn) | Montano et al., *Hum. Genet.*, 113(2): 162-9 (2003). |
| Amino acid position 69 (e.g., Phe69Val) | Kato et al., *Hum. Genet.*, 101(1): 97-101 (1997). |
| Amino acid position 90 (e.g., Arg90Trp) | Wraith, *Arch. Dis. Child.*, 72(3): 263-7 (1995). |
| Amino acid position 94 (e.g., Arg94Gly) | Bunge et al., *Hum. Mutat.*, 10(3): 223-32 (1997). |
| Amino acid position 111 (e.g., Gln111Ter) | Nykamp et al., *Genet. Med.*, 19(10): 1105-1117 (2017). |
| Amino acid position 139 (e.g., Gly139Ser) | Lee et al., *Korean J. Pediatr.*, 55(11): 430-7 (2012). |
| Amino acid position 141 (e.g., Trp141Arg) | Bunge et al., *Hum. Mutat.*, 10(3): 223-32 (1997). |
| Amino acid position 151 (e.g., Pro151Thr) | Lee et al., *Korean J. Pediatr.*, 55(11): 430-7 (2012). |
| Amino acid position 155 (e.g., Gly155Arg) | Van Goor et al., *J. Cyst Fibros.*, 13(1): 29-36 (2014). |
| Amino acid position 156 (e.g., Phe156Cys) | Yamada et al., *Hum. Mutat.*, 11(3): 202-8 (1998). |
| Amino acid position 159 (e.g., Trp159Ter) | Nykamp et al., *Genet. Med.*, 19(10): 1105-1117 (2017). |
| Amino acid position 162 (e.g., Ser162Phe) | Nykamp et al., *Genet. Med.*, 19(10): 1105-1117 (2017). |
| Amino acid position 181 (e.g., Tyr181Cys) | Seyedhassani et al., Clin Chim Acta. 2015 Oct. 23; 450: 121-4. |
| Amino acid position 204 (e.g., Asn204Lys) | Fukuda et al., *J. Clin. Invest.*, 90(3): 1049-53 (1992). |
| Amino acid position 230 (e.g., Trp230Ter) | Montano et al., *Hum. Genet.*, 113(2): 162-9 (2003). |
| Amino acid position 247 (e.g., Gly247Asp) | Van Goor et al., *J. Cyst Fibros.*, 13(1): 29-36 (2014). |
| Amino acid position 259 (e.g., Arg259Gln) | Bunge et al., *Hum. Mutat.*, 10(3): 223-32 (1997). |
| Amino acid position 287 (e.g., Ser287Leu) | Nykamp et al., *Genet. Med.*, 19(10): 1105-1117 (2017). |
| Amino acid position 291 (e.g., Ala291Thr) | Montano et al., *Hum. Genet.*, 113(2): 162-9 (2003). |
| Amino acid position 295 (e.g., Ser295Phe) | Wraith, *Arch. Dis. Child.*, 72(3): 263-7 (1995). |
| Amino acid position 301 (e.g., Gly301Cys) | Bunge et al., *Hum. Mutat.*, 10(3): 223-32 (1997). |
| Amino acid position 312 (e.g., Thr312Ser) | Yamada et al., *Hum. Mutat.*, 11(3): 202-8 (1998). |
| Amino acid position 334 (e.g., Gln334Ter) | Lee et al., *Korean J. Pediatr.*, 55(11): 430-7 (2012). |
| Amino acid position 340 (e.g., Gly340Asp) | Wang et al., *J. Hum. Genet.*, 55(8): 534-40 (2010). |
| Amino acid position 386 (e.g., Arg386Cys) | Van Goor et al., *J. Cyst Fibros.*, 13(1): 29-36 (2014). |
| Amino acid position 391 (e.g., Met391Val) | Van Goor et al., *J. Cyst Fibros.*, 13(1): 29-36 (2014). |
| Amino acid position 473 (e.g., Gln473Ter) | Tomatsu et al., *Hum. Mutat.*, 6(2): 195-6 (1995). |
| Amino acid position 487 (e.g., Asn487Ser) | Tomatsu et al., *Hum. Mutat.*, 6(2): 195-6 (1995). |

| GLB1 Mutations | References |
|---|---|
| Amino acid position 51 (e.g., Ile51Thr) | Yoshida et al., *Am. J. Hum. Genet.*, 49(2): 435-42 (1991). |
| Amino acid position 57 (e.g., Tyr57Ter) | Van Goor et al., *J. Cyst Fibros.*, 13(1): 29-36 (2014). |
| Amino acid position 59 (e.g., Arg59Cys) | Santamaria et al., *Hum. Mutat.*, 27(10): 1060 (2006). |
| Amino acid position 59 (e.g., Arg59His) | Morrone et al., Hum. Mutat., 15(4): 354-66 (2000). |
| Amino acid position 68 (e.g., Arg68Trp) | Caciotti et al., *Biochem. Biophys. Acta.*, 1812(7): 782-90 (2011). |
| Amino acid position 83 (e.g., Tyr83His) | Ishii et al., *Clin. Genet.*, 48(2): 103-8 (1995). |
| Amino acid position 95 (e.g., Gln95Thrfs) | Yoshida et al., *Am. J. Hum. Genet.*, 49(2): 435-42 (1991). |
| Amino acid position 107 (e.g., Phe107Leu) | Hofer et al., *Clin. Genet.*, 78(3): 236-46 (2010). |
| Amino acid position 148 (e.g., Arg148Cys) | Hofer et al., *Clin. Genet.*, 78(3): 236-46 (2010). |
| Amino acid position 148 (e.g., Arg148His) | Richards et al., *Genet, Med.*, 17(5): 405-24 (2015). |
| Amino acid position 148 (e.g., Arg148Ser) | Hinek et al., *Am. J. Hum. Genet.*, 67(1): 23-36 (2000). |
| Amino acid position 18 (e.g., Leu18Serfs) | Bean et al., *Hum. Mutat.*, 34(9): 1183-8 (2013). |
| Amino acid position 201 (e.g., Arg201His) | Kaye et al., *J. Child Neurol.*, 12(4): 242-7 (1997). |
| Amino acid position 208 (e.g., Arg208Cys) | Van Goor et al., *J. Cyst Fibros.*, 13(1): 29-36 (2014). |
| Amino acid position 255 (e.g., Gln255His) | Hofer et al., *Hum. Mutat.*, 30(8): 1214-21 (2009). |
| Amino acid position 270 (e.g., Tyr270Asp) | Van Goor et al., *J. Cyst Fibros.*, 13(1): 29-36 (2014). |
| Amino acid position 273 (e.g., Trp273Leu) | Oshima et al., *Am. J. Hum. Genet.*, 49(5): 1091-3 (1991). |
| Amino acid position 273 (e.g., Trp273Leu) | Caciotti et al., *Biochem. Biophys. Acta.*, 1812(7): 782-90 (2011). |
| Amino acid position 283 (e.g., Thr283Glnfs) | Santamaria et al., *Hum. Mutat.*, 27(10): 1060 (2006). |
| Amino acid position 301 (e.g., Ala301Val) | Santamaria et al., *Hum. Mutat.*, 27(10): 1060 (2006). |
| Amino acid position 316 (e.g., Tyr316Cys) | Yoshida et al., *Am. J. Hum. Genet.*, 49(2): 435-42 (1991). |
| Amino acid position 329 (e.g., His329Tyr) | Caciotti et al., *Biochem. Biophys. Acta.*, 1812(7): 782-90 (2011). |

TABLE 1-continued

| | |
|---|---|
| Amino acid position 346 (e.g., Lys346Asn) | Santamaria et al., *Hum. Mutat.*, 27(10): 1060 (2006). |
| Amino acid position 346 (e.g., Lys346Asn) | Santamaria et al., *Hum. Mutat.*, 27(10): 1060 (2006). |
| Amino acid position 351 (e.g., Arg351Ter) | Caciotti et al., *Biochem. Biophys. Acta.*, 1812(7): 782-90 (2011). |
| Amino acid position 438 (e.g., Gly438Glu) | Hinek et al., *Am. J. Hum. Genet.*, 67(1): 23-36 (2000). |
| Amino acid position 441 (e.g., Asp441Asn) | Santamaria et al., *Hum. Mutat.*, 27(10): 1060 (2006). |
| Amino acid position 442 (e.g., Arg442Gln) | Caciotti et al., *Biochem. Biophys. Acta.*, 1812(7): 782-90 (2011). |
| Amino acid position 457 (e.g., Arg457Gln) | Yoshida et al., *Am. J. Hum. Genet.*, 49(2): 435-42 (1991). |
| Amino acid position 457 (e.g., Arg457Ter) | Santamaria et al., *Hum. Mutat.*, 27(10): 1060 (2006). |
| Amino acid position 482 (e.g., Arg482His) | Van Goor et al., *J. Cyst Fibros.*, 13(1): 29-36 (2014). |
| Amino acid position 489 (e.g., Ile489Metfs) | Bean et al., *Hum. Mutat.*, 34(9): 1183-8 (2013). |
| Amino acid position 500 (e.g., Thr500Ala) | Hofer et al., *Clin. Genet.*, 78(3): 236-46 (2010). |
| Amino acid position 504 (e.g., Asn504Argfs) | Santamaria et al., *Hum. Mutat.*, 27(10): 1060 (2006). |
| Amino acid position 509 (e.g., Trp509Cys) | Oshima et al., *Am. J. Hum. Genet.*, 49(5): 1091-3 (1991). |
| Amino acid position 527 (e.g., Trp527Leufs) | Silva et al., *Hum. Mutat.*, 13(5): 401-9 (1999). |
| Amino acid position 549 (e.g., Pro549Leu) | Santamaria et al., *Hum. Mutat.*, 27(10): 1060 (2006). |
| Amino acid position 578 (e.g., Lys578Arg) | Caciotti et al., *Biochem. Biophys. Acta.*, 1812(7): 782-90 (2011). |
| Amino acid position 582 (e.g., Trp582Ter) | Hofer et al., *Clin. Genet.*, 78(3): 236-46 (2010). |
| Amino acid position 590 (e.g., Arg590Cys) | Van Goor et al., *J. Cyst Fibros.*, 13(1): 29-36 (2014). |
| Amino acid position 591 (e.g., Tyr591Asn) | Van Goor et al., *J. Cyst Fibros.*, 13(1): 29-36 (2014). |
| ARSB Mutations | Reference |
| Amino acid position 39 (e.g., Ala39Glufs) | Tomanin et al., *Hum. Mutat.*, 39(12): 1788-1802 (2018). |
| Amino acid position 39 (e.g., Ala39Profs) | Tomanin et al., *Hum. Mutat.*, 39(12): 1788-1802 (2018). |
| Amino acid position 50 (e.g., Leu50Ter) | Tomanin et al., *Hum. Mutat.*, 39(12): 1788-1802 (2018). |
| Amino acid position 53 (e.g., Asp53Asn) | Tomanin et al., *Hum. Mutat.*, 39(12): 1788-1802 (2018). |
| Amino acid position 54 (e.g., Asp54Asn) | Tomanin et al., *Hum. Mutat.*, 39(12): 1788-1802 (2018). |
| Amino acid position 59 (e.g., Asp59Val) | Tomanin et al., *Hum. Mutat.*, 39(12): 1788-1802 (2018). |
| Amino acid position 72 (e.g., Leu72Alafs) | Tomanin et al., *Hum. Mutat.*, 39(12): 1788-1802 (2018). |
| Amino acid position 72 (e.g., Leu72Arg) | Tomanin et al., *Hum. Mutat.*, 39(12): 1788-1802 (2018). |
| Amino acid position 73 (e.g., Asp73Glufs) | Tomanin et al., *Hum. Mutat.*, 39(12): 1788-1802 (2018). |
| Amino acid position 75 (e.g., Leu75Alafs) | Tomanin et al., *Hum. Mutat.*, 39(12): 1788-1802 (2018). |
| Amino acid position 80 (e.g., Val80Trpfs) | Tomanin et al., *Hum. Mutat.*, 39(12): 1788-1802 (2018). |
| Amino acid position 82 (e.g., Leu82Arg) | Garrido et al., *Mol. Genet. Metab.*, 94(3): 305-12 (2008). |
| Amino acid position 82 (e.g., Leu82Argfs) | Tomanin et al., *Hum. Mutat.*, 39(12): 1788-1802 (2018). |
| Amino acid position 83 (e.g., Asp83Glnfs) | Tomanin et al., *Hum. Mutat.*, 39(12): 1788-1802 (2018). |
| Amino acid position 85 (e.g., Tyr85His) | Tomanin et al., *Hum. Mutat.*, 39(12): 1788-1802 (2018). |
| Amino acid position 88 (e.g., Gln88Ter) | Tomanin et al., *Hum. Mutat.*, 39(12): 1788-1802 (2018). |
| Amino acid position 89 (e.g., Pro89Alafs) | Tomanin et al., *Hum. Mutat.*, 39(12): 1788-1802 (2018). |
| Amino acid position 91 (e.g., Cys91Alafs) | Al-Sannaa et al., *J. Community Genet.*, 9(1): 65-70 (2018). |
| Amino acid position 95 (e.g., Arg95Gln) | Tomanin et al., *Hum. Mutat.*, 39(12): 1788-1802 (2018). |
| Amino acid position 97 (e.g., Gln97Ter) | Tomanin et al., *Hum. Mutat.*, 39(12): 1788-1802 (2018). |
| Amino acid position 98 (e.g., Leu98Arg) | Tomanin et al., *Hum. Mutat.*, 39(12): 1788-1802 (2018). |
| Amino acid position 98 (e.g., Leu98Gln) | Tomanin et al., *Hum. Mutat.*, 39(12): 1788-1802 (2018). |
| Amino acid position 110 (e.g., Gln110Ter) | Tomanin et al., *Hum. Mutat.*, 39(12): 1788-1802 (2018). |
| Amino acid position 117 (e.g., Cys117Arg) | Tomanin et al., *Hum. Mutat.*, 39(12): 1788-1802 (2018). |
| Amino acid position 126 (e.g., Glu126Terfs) | Tomanin et al., *Hum. Mutat.*, 39(12): 1788-1802 (2018). |
| Amino acid position 132 (e.g., Leu132Pro) | Tomanin et al., *Hum. Mutat.*, 39(12): 1788-1802 (2018). |
| Amino acid position 143 (e.g., Val143Serfs) | Tomanin et al., *Hum. Mutat.*, 39(12): 1788-1802 (2018). |
| Amino acid position 144 (e.g., Gly144Arg) | Tomanin et al., *Hum. Mutat.*, 39(12): 1788-1802 (2018). |
| Amino acid position 146 (e.g., Trp146Ter) | Tomanin et al., *Hum. Mutat.*, 39(12): 1788-1802 (2018). |
| Amino acid position 152 (e.g., Arg152Trp) | Brands et al., *Orphanet J. Rare Dis.*, 8: 51 (2013). |
| Amino acid position 160 (e.g., Arg160Gln) | Tomanin et al., *Hum. Mutat.*, 39(12): 1788-1802 (2018). |
| Amino acid position 160 (e.g., Arg160Ter) | Tomanin et al., *Hum. Mutat.*, 39(12): 1788-1802 (2018). |
| Amino acid position 166 (e.g., Phe166Leufs) | Tomanin et al., *Hum. Mutat.*, 39(12): 1788-1802 (2018). |
| Amino acid position 170 (e.g., Leu170Arg) | Tomanin et al., *Hum. Mutat.*, 39(12): 1788-1802 (2018). |
| Amino acid position 171 (e.g., Gly171Ser) | Tomanin et al., *Hum. Mutat.*, 39(12): 1788-1802 (2018). |
| Amino acid position 178 (e.g., His178Asp) | Tomanin et al., *Hum. Mutat.*, 39(12): 1788-1802 (2018). |
| Amino acid position 178 (e.g., His178Leu) | Tomanin et al., *Hum. Mutat.*, 39(12): 1788-1802 (2018). |
| Amino acid position 191 (e.g., Arg191Ter) | Ferla et al., *Hum. Gene Ther.*, 26(3): 145-52 (2005). |
| Amino acid position 192 (e.g., Cys192Arg) | Tomanin et al., *Hum Mutat.*, 39(12): 1788-1802 (2018). |
| Amino acid position 197 (e.g., Arg197Ter) | Petry et al., *J Inherit Metab. Dis.*, 28(6): 1027-34 (2005). |
| Amino acid position 210 (e.g., Tyr210Cys) | Litjens et al., *Am. J. Hum. Genet.*, 58(6): 1127-34 (1996). |
| Amino acid position 210 (e.g., Tyr210Terfs) | Tomanin et al., *Hum. Mutat.*, 39(12): 1788-1802 (2018). |
| Amino acid position 220 (e.g., Ile220Serfs) | Tomanin et al., *Hum. Mutat.*, 39(12): 1788-1802 (2018). |
| Amino acid position 223 (e.g., Ile223Val) | Tomanin et al., *Hum. Mutat.*, 39(12): 1788-1802 (2018). |
| Amino acid position 248 (e.g., Pro248Leufs) | Tomanin et al., *Hum. Mutat.*, 39(12): 1788-1802 (2018). |
| Amino acid position 250 (e.g., Glu250Aspfs) | Tomanin et al., *Hum. Mutat.*, 39(12): 1788-1802 (2018). |
| Amino acid position 250 (e.g., Glu250Aspfs) | Tomanin et al., *Hum. Mutat.*, 39(12): 1788-1802 (2018). |
| Amino acid position 251 (e.g., Tyr251Ter) | Al-Sannaa et al., *J Community Genet.*, 9(1): 65-70 (2018). |
| Amino acid position 255 (e.g., Tyr255Ter) | Tomanin et al., *Hum. Mutat.*, 39(12): 1788-1802 (2018). |
| Amino acid position 262 (e.g., Asn262Lysfs) | Tomanin et al., *Hum. Mutat.*, 39(12): 1788-1802 (2018). |
| Amino acid position 296 (e.g., Ile296Asn) | Tomanin et al., *Hum. Mutat.*, 39(12): 1788-1802 (2018). |
| Amino acid position 296 (e.g., Ile296Serfs) | Tomanin et al., *Hum. Mutat.*, 39(12): 1788-1802 (2018). |

TABLE 1-continued

| | |
|---|---|
| Amino acid position 301 (e.g., Asn301Lys) | Tomanin et al., *Hum. Mutat.*, 39(12): 1788-1802 (2018). |
| Amino acid position 303 (e.g., Gly303Glu) | Tomanin et al., *Hum. Mutat.*, 39(12): 1788-1802 (2018). |
| Amino acid position 312 (e.g., Trp312Cys) | Karageorgos et al., Hum Mutat. 2004 March; 23(3): 229-33. |
| Amino acid position 313 (e.g., Pro313Ala) | Tomanin et al., *Hum. Mutat.*, 39(12): 1788-1802 (2018). |
| Amino acid position 315 (e.g., Arg315Gln) | Villani et al., *Genet. Test Mol. Biomark.*, 14(1): 113-20 (2010). |
| Amino acid position 315 (e.g., Arg315Ter) | Tomanin et al., *Hum. Mutat.*, 39(12): 1788-1802 (2018). |
| Amino acid position 321 (e.g., Leu321Pro) | Tomanin et al., *Hum. Mutat.*, 39(12): 1788-1802 (2018). |
| Amino acid position 322 (e.g., Trp322Ter) | Tomanin et al., *Hum. Mutat.*, 39(12): 1788-1802 (2018). |
| Amino acid position 324 (e.g., Gly324Val) | Tomanin et al., *Hum. Mutat.*, 39(12): 1788-1802 (2018). |
| Amino acid position 327 (e.g., Arg327Ter) | Karageorgos et al., *Hum. Mutat.*, 23(3): 229-33 (2004). |
| Amino acid position 332 (e.g., Val332Gly) | Tomanin et al., *Hum. Mutat.*, 39(12): 1788-1802 (2018). |
| Amino acid position 350 (e.g., Ile350Phe) | Tomanin et al., *Hum. Mutat.*, 39(12): 1788-1802 (2018). |
| Amino acid position 351 (e.g., Ser351Phe) | Tomanin et al., *Hum. Mutat.*, 39(12): 1788-1802 (2018). |
| Amino acid position 353 (e.g., Trp353Ter) | Tomanin et al., *Hum. Mutat.*, 39(12): 1788-1802 (2018). |
| Amino acid position 360 (e.g., Leu360Pro) | Tomanin et al., *Hum. Mutat.*, 39(12): 1788-1802 (2018). |
| Amino acid position 376 (e.g., Val376Glu) | Tomanin et al., *Hum. Mutat.*, 39(12): 1788-1802 (2018). |
| Amino acid position 377 (e.g., Trp377Ter) | Tomanin et al., *Hum. Mutat.*, 39(12): 1788-1802 (2018). |
| Amino acid position 388 (e.g., Arg388Glnfs) | Tomanin et al., *Hum. Mutat.*, 39(12): 1788-1802 (2018). |
| Amino acid position 39 (e.g., Ala39Glufs) | Tomanin et al., *Hum. Mutat.*, 39(12): 1788-1802 (2018). |
| Amino acid position 390 (e.g., Glu390Lys) | Tomanin et al., *Hum. Mutat.*, 39(12): 1788-1802 (2018). |
| Amino acid position 399 (e.g., Phe399Leu) | Tomanin et al., *Hum. Mutat.*, 39(12): 1788-1802 (2018). |
| Amino acid position 403 (e.g., Ser403Ter) | Tomanin et al., *Hum. Mutat.*, 39(12): 1788-1802 (2018). |
| Amino acid position 403 (e.g., Ser403Tyrfs) | Tomanin et al., *Hum. Mutat.*, 39(12): 1788-1802 (2018). |
| Amino acid position 421 (e.g., Glu421Ter) | Tomanin et al., *Hum. Mutat.*, 39(12): 1788-1802 (2018). |
| Amino acid position 427 (e.g., Thr427Hisfs) | Tomanin et al., *Hum. Mutat.*, 39(12): 1788-1802 (2018). |
| Amino acid position 430 (e.g., His430Arg) | Tomanin et al., *Hum. Mutat.*, 39(12): 1788-1802 (2018). |
| Amino acid position 430 (e.g., His430Profs) | Tomanin et al., *Hum. Mutat.*, 39(12): 1788-1802 (2018). |
| Amino acid position 450 (e.g., Trp450Cys) | Mathew et al., *Mol. Genet. Metab. Rep.*, 4: 53-61 (2015). |
| Amino acid position 464 (e.g., Ser464Ter) | Tomanin et al., *Hum. Mutat.*, 39(12): 1788-1802 (2018). |
| Amino acid position 465 (e.g., Ser465Ter) | Tomanin et al., *Hum. Mutat.*, 39(12): 1788-1802 (2018). |
| Amino acid position 472 (e.g., Leu472Pro) | Tomanin et al., *Hum. Mutat.*, 39(12): 1788-1802 (2018). |
| Amino acid position 492 (e.g., Pro492Leufs) | Tomanin et al., *Hum. Mutat.*, 39(12): 1788-1802 (2018). |
| Amino acid position 494 (e.g., Ile494Metfs) | Tomanin et al., *Hum. Mutat.*, 39(12): 1788-1802 (2018). |
| Amino acid position 498 (e.g., Leu498Pro) | Tomanin et al., *Hum. Mutat.*, 39(12): 1788-1802 (2018). |
| Amino acid position 503 (e.g., Gln503Ter) | Tomanin et al., *Hum. Mutat.*, 39(12): 1788-1802 (2018). |
| Amino acid position 513 (e.g., Tyr513Ter) | Tomanin et al., *Hum. Mutat.*, 39(12): 1788-1802 (2018). |
| Amino acid position 526 (e.g., Thr526Metfs) | Tomanin et al., *Hum. Mutat.*, 39(12): 1788-1802 (2018). |
| GUSB Mutations | References |
| Amino acid position 103 (e.g., Arg103Trp) | Shamseldin et al., *Genome Biol.*, 16: 116 (2015). |
| Amino acid position 133 (e.g., Trp133Ser) | Shamseldin et al., *Genome Biol.*, 16: 116 (2015). |
| Amino acid position 148 (e.g., Pro148Ser) | Yamada et al., *Hum. Mol. Genet.*, 4(4): 651-5 (1995). |
| Amino acid position 176 (e.g., Leu176Phe) | Richard et al., *Genet Med.*, 17(5): 405-24 (2015). |
| Amino acid position 216 (e.g., Arg216Trp) | Vervkoort et al., *Hum Genet.*, 103(6): 686-93 (1998). |
| Amino acid position 350 (e.g., Lys350Asn) | Stroch et al., *Hum Genet.*, 112(2): 190-4 (2003). |
| Amino acid position 354 (e.g., Ala354Val) | Wu et al., *Hum Mutat.*, 2(6): 446-57 (1993). |
| Amino acid position 357 (e.g., Arg357Ter) | Shamseldin et al., *Genome Biol.*, 16: 116 (2015). |
| Amino acid position 382 (e.g., Arg382Cys) | Shamseldin et al., *Genome Biol.*, 16: 116 (2015). |
| Amino acid position 446 (e.g., Trp446Ter) | Vervkoort et al., *Hum Genet.*, 103(6): 686-93 (1998). |
| Amino acid position 446 (e.g., Trp446Ter) | Vervkoort et al., *Hum Genet.*, 103(6): 686-93 (1998). |
| Amino acid position 495 (e.g., Tyr495Cys) | Yamada et al., *Hum. Mol. Genet.*, 4(4): 651-5 (1995). |
| Amino acid position 507 (e.g., Trp507Ter) | Yamada et al., *Hum. Mol. Genet.*, 4(4): 651-5 (1995). |
| Amino acid position 512 (e.g., Gly512Arg) | Shamseldin et al., *Genome Biol.*, 16: 116 (2015). |
| Amino acid position 529 (e.g., Tyr529Cys) | Shamseldin et al., *Genome Biol.*, 16: 116 (2015). |
| Amino acid position 539 (e.g., Ser539Argfs*8) | Yamada et al., *Hum. Mol. Genet.*, 4(4): 651-5 (1995). |
| Amino acid position 577 (e.g., Arg577Leu) | Stroch et al., *Hum Genet.*, 112(2): 190-4 (2003). |
| Amino acid position 611 (e.g., Arg611Trp) | Wu et al., *Hum Mutat.*, 2(6): 446-57 (1993). |
| Amino acid position 619 (e.g., Ala619Val) | Tomatsu et al., *Am. J. Hum. Genet.*, 48(1): 89-96 (1991). |
| Amino acid position 627 (e.g., Trp627Cys) | Shipley et al., *Am. J. Hum. Genet.*, 52(3): 517-26 (1993). |
| HYAL1 Mutations | References |
| Amino acid position 251 (e.g., Val251Phefs) | Triggs-Raine et al., *Proc Natl Acad Sci.*, 96(11): 6296-300 (1999). |
| Amino acid position 268 (e.g., Glu268Lys) | Natowicz et al., *N Engl J Med.*, 335(14): 1029-33 (1996). |

The ClinVar database provided by the National Center for Biotechnology Information (NCBI) was used to identify known pathogenic genetic variants as shown in Table 1. See Richards et al., *Genet. Med.,* 17(5):405-24 (2015). As used in herein, "fs" refers to a genetic variant that resulted in a frameshift. For example, Val251Phefs refers to a frameshift mutation at amino acid position 251 that resulted in a change from valine to phenylalanine.

In some embodiments of any of the methods or uses described herein, the subject has a clinical record indicating that the subject has a dysregulation of an MPS-associated gene, an MPS-associated protein, or expression or activity or level of any of the same (e.g., having one or more mutations in an MPS-associated gene and/or MPS-associated protein, as described herein). In some embodiments, the clinical record indicates that the subject should be treated with a the trehalose formulations described herein. In some embodiments, the subject with a dysregulation of an MPS-associated gene, an MPS-associated protein, or expression or activity or level of any of the same is a subject having one or more point mutations in an MPS-associated gene and/or an MPS-associated protein. In some embodiments, the subject with a dysregulation of an MPS-associated gene, an MPS-associated protein, or expression or activity or level of any of the same is determined using a regulatory agency-approved, e.g., FDA-approved, assay or kit. In some embodiments, the sample with a dysregulation of an MPS-associated gene, an MPS-associated protein, or expression or activity or level of any of the same is determined using a regulatory agency-approved, e.g., FDA-approved, assay or kit.

Also provided are methods of treating a subject that include administering a the trehalose formulations described herein to a subject having a clinical record that indicates that the subject has a dysregulation of an MPS-associated gene, an MPS-associated protein, or expression or activity or level of any of the same. Also provided is the use of a the trehalose formulations described herein for the manufacture of a medicament for treating an MPS in a subject having a clinical record that indicates that the subject has a dysregulation of an MPS-associated gene, an MPS-associated protein, or expression or activity or level of any of the same. Some embodiments of these methods and uses can further include: a step of performing an assay (e.g., an in vitro assay) on a sample obtained from the subject to determine whether the subject has a dysregulation of an MPS-associated gene, an MPS-associated protein, or expression or activity or level of any of the same, and recording the information in a subject's clinical file (e.g., a computer readable medium) that the subject has been identified to have a dysregulation of an MPS-associated gene, an MPS-associated protein, or expression or activity or level of any of the same. In some embodiments, the assay is an in vitro assay. For example, an assay that utilizes genetic techniques, such as next generation sequencing, or measures GAG levels in a sample, or measures the activity of one or more enzymes in a sample. In some embodiments, the assay is a regulatory agency-approved, e.g., FDA-approved, kit.

Also provided herein is a method of treating a subject. In some embodiments, the method includes performing an assay on a sample obtained from the subject to determine whether the subject has a dysregulation of an MPS-associated gene, an MPS-associated protein, or expression or level of any of the same. In some such embodiments, the method also includes administering to a subject determined to have a dysregulation of an MPS-associated gene, an MPS-associated protein, or activity or level of any of the same. In some embodiments, the method includes determining that a subject has a dysregulation of an MPS-associated gene, an MPS-associated protein, or expression or level of any of the same via an assay performed on a sample obtained from the subject. In such embodiments, the method also includes administering to a subject a the trehalose formulations described herein. In some embodiments, the dysregulation in an MPS-associated gene, an MPS-associated protein, or expression or activity or level of any of the same is one or more point mutation in the MPS-associated gene (e.g., any of the one or more of the point mutations described herein, such as in Table 1). The one or more point mutations in an MPS-associated gene can result, e.g., in the translation of an MPS-associated protein having one or more of the amino acid substitutions described in Table 1. Some embodiments of these methods further include administering to the subject another therapy to the subject, such as an enzyme replacement therapy or substrate reduction therapy, as described herein.

In some embodiments, the methods described herein provide trehalose formulations that exhibit brain and/or central nervous system (CNS) penetrance. Thus, the methods described herein provide trehalose that is capable of crossing the blood brain barrier and providing a therapeutically effective amount of trehalose in the brain and/or other CNS structures. For example, treatment of a subject with an MPS having effects on the brain and/or CNS such as cognitive effects.

In some embodiments, the methods described herein provide trehalose formulations that exhibit penetrance into muscle tissue (including skeletal and smooth muscle). Thus, the methods described herein provide trehalose that is capable of penetrating into muscle tissue, thus providing a therapeutically effective amount of trehalose in the muscle fibers. For example, treatment of a subject with an MPS having effects on the muscles, such as kinesthetic or movement effects.

Also provided are methods (e.g., in vitro methods) of selecting a treatment for a subject identified or diagnosed as having an MPS. Some embodiments can further include administering the selected treatment to the subject identified or diagnosed as having an MPS. For example, the selected treatment can include administration of a the trehalose formulations described herein. Some embodiments can further include a step of performing an assay on a sample obtained from the subject to determine whether the subject has a dysregulation of an MPS-associated gene, an MPS-associated protein, or expression or activity or level of any of the same, and identifying and diagnosing a subject determined to have a dysregulation of an MPS-associated gene, an MPS-associated protein, or expression or activity or level of any of the same, as having an MPS. In some embodiments, the subject has been identified or diagnosed as having an MPS through the use of a regulatory agency-approved, e.g., FDA-approved, kit for identifying dysregulation of an MPS-associated gene, an MPS-associated protein, or expression or activity or level of any of the same, in a subject or a sample from the subject. In some embodiments, the assay is an in vitro assay. For example, an assay that utilizes genetic techniques, such as next generation sequencing, or measures GAG levels in a sample, or measures the activity of one or more enzymes in a sample. In some embodiments, the assay is a regulatory agency-approved, e.g., FDA-approved, kit.

In some embodiments of any of the methods or uses described herein, an assay used to determine whether the subject has a dysregulation of an MPS-associated gene, an MPS-associated protein, or expression or activity or level of any of the same, using a sample from a subject can include, for example, next generation sequencing, immunohistochemistry, fluorescence microscopy, Southern blotting, Western blotting, FACS analysis, Northern blotting, PCR-based amplification (e.g., RT-PCR and quantitative real-time RT-PCR), enzymatic activity assays, and assays to measure GAG levels in a sample. Assays can utilize other detection methods known in the art for detecting dysregulation of an MPS-associated gene, an MPS-associated protein, or expression or activity or levels of any of the same.

In some embodiments, the MPS-associated gene is selected from IDUA, IDS, SGSH, NAGLU, HGSNAT, GNS, GALNS, GLB1, ARSB, GUSB, and HYAL1. In some embodiments, the MPS-associated gene is IDUA. In other embodiments, the MPS-associated gene is IDS. In still other embodiments, the MPS-associated gene is SGSH. In some embodiments, the MPS-associated gene is NAGLU. In other embodiments, the MPS-associated gene is HGSNAT. In still other embodiments, the MPS-associated gene is GNS. In some embodiments, the MPS-associated gene is GALNS. In other embodiments, the MPS-associated gene is GLB1. In still other embodiments, the MPS-associated gene is ARSB. In some embodiments, the MPS-associated gene is GUSB. In other embodiments, the MPS-associated gene is HYAL1.

In some embodiments, the MPS-associated protein is selected from α-L-iduronidase, iduronate sulfatase, heparan sulfamidase, N-acetylglucosaminidase, heparan-α-glucosaminide N-acetyltransferase, N-acetylglucosamine 6-sulfatase, galactose-6-sulfate sulfatase, β-galactosidase, N-acetylgalactosamine-4-sulfatase, β-glucuronidase, and hyaluronidase. In some embodiments, the MPS-associated protein is α-L-iduronidase. In other embodiments, the MPS-associated protein is iduronate sulfatase. In still other embodiments, the MPS-associated protein is N-acetylglucosaminidase. In some embodiments, the MPS-associated protein is heparan-α-glucosaminide N-acetyltransferase. In other embodiments, the MPS-associated protein is N-acetylglucosamine 6-sulfatase. In still other embodiments, the MPS-associated protein is galactose-6-sulfate sulfatase. In some embodiments, the MPS-associated protein is β-galactosidase. In other embodiments, the MPS-associated protein is N-acetylgalactosamine-4-sulfatase. In still other embodiments, the MPS-associated protein is β-glucuronidase. In some embodiments, the MPS-associated protein is hyaluronidase.

In some embodiments, the mucopolysaccharidosis (or "MPS") is selected from the group consisting of: Hurler syndrome (MPS IH), Hurler-Scheie syndrome (MPS IH/S), Scheie syndrome (MPS IS or MPS V), Hunter syndrome (MPS II), Sanfillippo syndrome A (MPS IIIA), Sanfillippo syndrome B (MPS IIIB), Sanfillippo syndrome C (MPS IIIC), Sanfillippo syndrome D (MPS IIID), Morquio syndrome A (MPS IVA), Morquio syndrome B (MPS IVB), Maroteaux-Lamy syndrome (MPS VI), Sly syndrome (MPS VII), and Natowicz syndrome (MPS IX).

In some embodiments, the mucopolysaccharidosis (or "MPS") is Hurler syndrome (MPS IH). In other embodiments, the MPS is Hurler-Scheie syndrome (MPS IHS). In still other embodiments, the MPS is Scheie syndrome (MPS IS or MPS V). In some embodiments, the MPS is Hunter syndrome (MPS II). In some embodiments, the MPS is selected from the group consisting of: Sanfillippo syndrome A (MPS IIIA), Sanfillippo syndrome B (MPS IIIB), Sanfillippo syndrome C (MPS IIIC), and Sanfillippo syndrome D (MPS IIID). In some embodiments, the MPS is Sanfillippo syndrome A (MPS IIIA). In other embodiments, the MPS is Sanfillippo syndrome B (MPS IIIB). In still other embodiments, the MPS is Sanfillippo syndrome C (MPS IIIC). In some embodiments, the MPS is and Sanfillippo syndrome D (MPS IIID). In some embodiments, the MPS is Morquio syndrome A (MPS IVA). In other embodiments, the MPS is Morquio syndrome B (MPS IVB). In still other embodiments, the MPS is Maroteaux-Lamy syndrome (MPS VI). In some embodiments, the MPS is Sly syndrome (MPS VII). In other embodiments, the MPS is and Natowicz syndrome (MPS IX).

Some embodiments described herein include determining that a subject has a lysosomal enzyme deficiency, treating a subject that has been determined to have a lysosomal enzyme deficiency, or alleviating one or more symptoms in a subject that has been determined to have a lysosomal enzyme deficiency. The determination that a subject has a lysosomal deficiency can include various tests, for example, a genetic test, a blood test, a urine test, an in vitro enzymatic assay (e.g., testing a sample of cells and/or tissue(s) and/or bodily fluid(s) for enzymatic activity), or a combination of any of the foregoing. In some embodiments, determining that a subject has a lysosomal enzyme deficiency comprises a genetic test. In other embodiments, determining that a subject has a lysosomal enzyme deficiency comprises a blood test. In still other embodiments, determining that a subject has a lysosomal enzyme deficiency comprises a urine test. In some embodiments, determining that a subject has a lysosomal enzyme deficiency comprises an in vitro enzymatic assay. In some embodiments, determining that a subject has a lysosomal enzyme deficiency comprises amniocentesis, chorionic villus sampling, or a combination thereof.

In some embodiments, the alleviation of one or more symptoms in a subject that has been determined to have a lysosomal enzyme deficiency can include, but is not limited to, reducing the frequency of respiratory infections, sleep apnea, hearing loss, ear infections, corneal clouding, diarrhea, skin growths, irregularities in bone shape and/or size, irregularities in heart valve structure and/or function, hoarse voice, joint stiffness, aggressive behavior, distended abdomen, spinal stenosis, and developmental delays.

In some embodiments, the enzyme deficiency is a deficiency in an enzyme selected from the group consisting of: α-L-iduronidase, iduronate sulfatase, heparan sulfamidase, N-acetylglucosaminidase, heparan-α-glucosaminide N-acetyltransferase, N-acetylglucosamine 6-sulfatase, galactose-6-sulfate sulfatase, β-galactosidase, N-acetylgalactosamine-4-sulfatase, β-glucuronidase, and hyaluronidase. In some embodiments, the enzyme deficiency is a deficiency in α-L-iduronidase. In other embodiments, the enzyme deficiency is a deficiency in iduronate sulfatase. In still other embodiments, the enzyme deficiency is a deficiency in N-acetylglucosaminidase. In some embodiments, the enzyme deficiency is a deficiency in heparan-α-glucosaminide N-acetyltransferase. In other embodiments, the enzyme deficiency is a deficiency in N-acetylglucosamine 6-sulfatase. In still other embodiments, the enzyme deficiency is a deficiency in galactose-6-sulfate sulfatase. In some embodiments, the enzyme deficiency is a deficiency in β-galactosidase. In other embodiments, the enzyme deficiency is a deficiency in N-acetylgalactosamine-4-sulfatase. In still other embodiments, the enzyme deficiency is a deficiency in β-glucuronidase. In some embodiments, the enzyme deficiency is a deficiency in hyaluronidase.

In some embodiments, the methods described herein provide a reduction in one or more of the aggregation products of the MIPS in a subject (e.g., one or more of heparan sulfate, dermatan sulfate, keratan sulfate, chondroitin sulfate, and/or hyaluronic acid). For example, a reduction (e.g., about 20% to about 99% reduction, about 20% to about 95% reduction, about 20% to about a 90% reduction, about 20% to about a 85% reduction, about 20% to about a 80% reduction, about 20% to about a 75% reduction, about 20% reduction to about 70% reduction, about 20% reduction to about 65% reduction, about 20% reduction to about 60% reduction, about 20% reduction to about 55% reduction, about 20% reduction to about 50% reduction, about 20% reduction to about 45% reduction, about 20% reduction to about 40% reduction, about 20% reduction to about 35% reduction, about 1% reduction to about 30% reduction, about 20% reduction to about 25% reduction, about 20% to about 99% reduction, about 25% to about 99% reduction, about 30% to about 99% reduction, about 35% to about 99% reduction, about 40% to about 99% reduction, about 45% to about 99% reduction, about 50% to about 99% reduction, about 55% to about 99% reduction, about 60% to about 99% reduction, about 65% to about 99% reduction, about 70% to about 99% reduction, about 75% to about 95% reduction, about 80% to about 99% reduction, about 90% reduction to about 99% reduction, about 95% to about 99% reduction, about 20% to about 40% reduction, about 25% to about 50% reduction, about 35% to about 55% reduction, about 40% to about 60% reduction, about 50% reduction to about 75% reduction, about 60% reduction to about 80% reduction, or about 65% to about 85% reduction) in levels of one or more of heparan sulfate, dermatan sulfate, keratan sulfate, chondroitin sulfate, and/or hyaluronic acid in a subject.

EXAMPLES

The following examples illustrate the invention.

Example 1: Study to Assess Safety and Efficacy of IV Trehalose Injection in Patients with Sanfilippo Syndrome Type A or Type B Methodology: A three-part study of IV Trehalose Injection 90 mg/mL for the treatment of Sanfilippo syndrome type A and type B is conducted. Patients with genetically confirmed Sanfilippo syndrome type A or B who have elevated excretion of GAGs in the urine and/or elevated levels of HS in plasma and/or urine are eligible for enrollment. The study will be conducted in three parts as described below.

Part 1: Part 1 has a 4-week screening period followed by an initial 30-week dose escalation period (7-week open-label dose escalation period, followed by 23 weeks of treatment) (Table 1). This period of the study will be used to assess the safety and tolerability of escalating dose levels of IV trehalose, to identify patients who will continue as the enriched cohort in Part 2 of the study using MDRI at Week 30, and to assess the association over time between neurocognitive and behavioral symptoms and biomarkers.

During the screening period, urinary GAG, and urinary and plasma HS biomarkers will be collected 3 times, 7 days apart, to establish the baseline excretion and plasma concentration. Patients will have the following baseline assessments: physical exam, safety labs, electrocardiogram (ECG), CT scan of the liver and spleen for volumetric determination, and ABR. Neurocognitive and behavioral assessments will be performed using the VABS-3, either the BSID-III or the KABC-II, and the SBRS. Quality of life will be assessed using the PedsQL™.

Baseline assessment of mobility will include the TUG test. Baseline functional and motor capabilities will be assessed, and the patient will be videotaped during the assessments. The assessments include the 9-hole peg test (9-HPT), TUG test, 10-meter Walk test, and pre-specified items of the Gross Motor Function Measure (GMFM). Subsequently, an independent physical therapist or other qualified clinician will review video of the patient completing the assessments and score the degree of the patient's change in ability to perform assessments using the CGIC scale.

Caregivers will be administered the CaGIS through an interview by a physical therapist or other qualified clinician. Baseline assessment of swallowing will include the 80 mL cold water drinking test and the Sydney Swallowing questionnaire. Baseline assessment of hearing will be performed by the ABR test.

Dose Escalation: The dose escalation will begin on treatment Week 1 with a starting dose of 0.25 g/kg of trehalose administered IV over 60 minutes once weekly. At Week 3 (after the first 2 weekly doses of 0.25 g/kg), patients will have safety labs, selected biomarkers (urinary GAGs, urinary and plasma HS), and PK levels assessed. A Safety Review Committee (SRC) consisting of the sponsor's chief medical officer or designee with a medical degree, the lead principal investigator (PI), an external physician with clinical trial safety data review experience, and a PK expert will be convened. The SRC will review each patient's safety, PK, and biomarker data within 1 week of the Week 3 dose. If there are no safety, PK or biomarker concerns identified, the dose will be increased to 0.50 g/kg at Week 4. Although the committee will make a recommendation, the ultimate decision to escalate the dose, continue the same dose or stop treatment is the responsibility of the local PI at all decision points. At Week 6 (after 2 weekly doses of 0.50 g/kg), patients will have safety labs, biomarkers, and PK levels assessed. The SRC will review each patient's safety, PK, and biomarker data within 1 week of the Week 6 dose. If there are no safety, PK or biomarker issues identified by the SRC, the dose will be increased to 0.75 g/kg at Week 7. At Week 9 (after 2 weekly doses of 0.75 g/kg), patients will have safety labs, biomarkers, and PK levels assessed. The SRC will review each patient's safety, PK, and biomarker data within 1 week of the Week 9 dose. If there are no safety, PK or biomarker issues identified by the SRC, the dose will remain at 0.75 g/kg.

Patients will reach their maximum tolerated dose (MTD) by Week 7 and will continue treatment at their MTD to the end of the 30-week treatment period. At Week 30, all safety and efficacy measures will be performed including: adverse events, physical exam, safety labs, biomarkers, ECG, PK, CT of liver and spleen, ABR, neurocognitive and behavioral testing, swallowing, mobility, and video assessments, as well as quality of life assessment.

Treatment Assignment for Part 2: Once each patient has completed the safety and efficacy assessments at Week 30, an independent DMC will be convened to review patient data. The DMC will be composed of clinical experts and an independent statistician. Using a priori defined criteria (MDRI), the DMC will assign the patient to either receive placebo (enriched cohort) or continue receiving IV trehalose (active treatment cohort) in Part 2 of the study.

The criteria for inclusion in the study are, for example, subjects having (i) at least a pre-specified minimum reduction in any of the following biomarkers (urinary GAGs or HS, plasma HS) at Week 30; or (ii) evidence of slowed or stabilized disease progression or improvement in neurocognitive or behavioral assessments at Week 30. These subjects will receive placebo in Part 2 of the study. This group of patients will constitute the enriched cohort for Part 2 of the study. Patients who do not meet the predefined criteria will continue IV trehalose treatment as part of active treatment cohort in Part 2 of the study.

Part 2: Part 2 is an 18-week assessment period composed of a 2-week transition followed by a 16-week crossover to placebo for the enriched cohort and continuation of IV trehalose for the active treatment cohort (Table 2). This phase of the study will be used to assess the loss of effect (deterioration) in the enriched cohort following a one-way crossover to placebo, assess the continued safety and tolerability and effect of continued IV trehalose in the active treatment cohort, as well as determine the efficacy of IV trehalose as assessed by effects on GAGs and HS and neurocognitive and behavioral symptoms in patients with Sanfilippo syndrome type A and type B.

All patients will receive IV trehalose during the 2-week transition period. Once treatments for Part 2 are assigned, patients will receive placebo or continued IV trehalose during the 16 week treatment period.

The 16-week treatment period occurs from Weeks 33 through 48 with patients assigned to one of two treatment cohorts: (i) The active treatment cohort, receiving weekly IV trehalose 90 mg/mL at individual MTD; and (ii) the enriched cohort, receiving weekly IV placebo (sodium chloride injection, 0.9%, USP).

At each study site, the blinded treatment assignment will be provided to the unblinded pharmacist or designee who will prepare the active drug or placebo for administration. Safety lab, ECG, and efficacy assessments will take place at Weeks 40 and 48 (safety lab assessment also at Week 34), while biomarker assessments will take place every 2 weeks during the treatment crossover period. All results will be monitored by the DMC chair. The one-way crossover to placebo for patients in the enriched cohort is intended to last for 16 weeks. To control for bias during Part 2, only the pharmacist or designee, the pharmacy monitor, and the statistician will be aware of the assignment of study drug because assignment to the active treatment or enriched cohort will not be revealed. The treatment assignment in Part 2 of the study will be blinded to prevent bias in the determination of the MDRI for the assessment of efficacy after 48 weeks on study.

Part 3: During the concluding 24-week open-label extension period, all patients will receive weekly dosing with IV trehalose 90 mg/mL at the individual MTD (Table 3). Safety lab assessments occur at Weeks 50 and 56 and then every 8 weeks for the duration of the open-label extension period. Biomarker assessments occur every 2 weeks for the first 8 weeks, then every 4 weeks for the duration of the open-label extension period. An ECG and all efficacy assessments are performed at Week 72 (final visit).

Patients who complete the 76-week study may continue treatment under a separate treatment extension protocol in lieu of marketing approval.

Exemplary criteria for diagnosis and main criteria for inclusion & exclusion are listed below.

Inclusion:
1. Provided written informed consent signed by parent(s) or legal guardian(s)
2. Genetically confirmed Sanfilippo syndrome type A or type B,
   a. Genomic DNA analysis demonstrating a homozygous or compound heterozygous pathogenic variants in the SGSH (type A) or NAGLU (type B) genes
3. Elevated excretion of urinary GAGs and/or urinary or plasma HS at screening (mean of 3 assessments>upper limit of normal [ULN])
4. Male or female; 6 to 21 years of age, inclusive
5. Negative urine or beta-human chorionic gonadotropin (␤-hCG) pregnancy result at screening for female patients with child-bearing potential
6. Willingness to comply with sexual abstinence or contraception guidelines as instructed Exclusion:
1. Prior administration of stem cell or gene therapy, or enzyme replacement therapy (ERT) for Sanfilippo syndrome type A or type B
2. Previously diagnosed with diabetes or a hemoglobin A1c (HgbA1c) result>6.0% at screening
3. Poorly controlled seizures, defined as one or more seizure per week for the last 4-6 weeks
4. Visual or hearing impairment sufficient to preclude cooperation with neurodevelopmental testing
5. Any other medical condition that, in the opinion of the investigator, would confound interpretation of safety or efficacy data or would place a patient at undue risk
6. Inability to cooperate with protocol-required assessments or procedures
7. Prior treatment with IV trehalose
8. Known hypersensitivity to trehalose
9. Use of genistein-rich soy isoflavone within 30 days before signing of consent
10. Use of oral trehalose within 7 days before signing of consent
11. Evidence of hepatitis B or hepatitis C infection upon serological testing at screening
12. Currently receiving anti-coagulant treatment (e.g., warfarin, enoxaparin), other than anti-platelet treatments, which are not a reason for exclusion
13. Currently participating in another clinical trial or has completed an interventional trial less than 90 days prior to planned first dosing Investigational product, dosage and mode of administration: Trehalose 90 mg/mL solution will be administered IV in Part 1 over 60±5 minutes once weekly in a dose escalation manner as described above starting with a dose of 0.25 g/kg and up to a maximum dose of 0.75 g/kg. Patients will be administered trehalose IV or placebo over 60±5 minutes once weekly in Part 2 (active treatment cohort and enriched cohort, respectively) and IV trehalose for all patients in Part 3. Indwelling catheters are not permitted.

Reference therapy, dosage and mode of administration: Placebo (sodium chloride injection, 0.9%, USP administered IV)

Restricted Medications: There are no known drug-drug interactions with IV trehalose 90 mg/mL. If the patient starts the study on miglustat, the dose must remain the same throughout the study. Patients are not permitted to initiate treatment with miglustat while on study. Cannabidiol (CBD) oil is permitted but the dose must remain the same throughout the study. Behavioral medications (stimulants, non-stimulants, psychotropic medications) are permitted if the patient is taking them at the time of consent. The dose and frequency should remain the same throughout the study if at all possible. Oral trehalose and genistein-rich soy isoflavones are not permitted during the study. Patients should not change concomitant medications during the study unless they experience an exacerbation of epilepsy or an acute illness. Patients may receive concomitant medications that are medically necessary as standard care only to treat symptoms, AEs, inter-current illnesses, and to prevent illness, e.g. vaccines. Over-the-counter (OTC) medications such as vitamins or herbal supplements are permitted if the patient is taking them at the time of consent. The dose and frequency should remain the same throughout the study if at all possible.

Statistical methods: Patients enrolled into this clinical investigation are expected to represent a heterogeneous population relative to their symptoms and clinical presentation. To account for these differences, the evaluation of a patient will use a multi-domain responder index (MDRI). The criterion for establishing response will be documented in the DMC charter, given it will be under the purview of the DMC to sanction patients for participation in the cross-over portion of Part 2 of the study and assess the loss of effect. The DMC will be blinded to treatment assignment in Part 2 of the study to prevent bias in the determination of the MDRI on an intra-patient basis.

Descriptive summaries of continuous safety and efficacy data including number of evaluable subjects, mean, median, standard deviation (SD), maximum and minimum will be provided by treatment and scheduled visit. Summaries for categorical variables will include number evaluable, frequencies, and percentages. Additionally, the same descriptive statistics will be provided for changes from baseline and percent changes from baseline at each post-baseline visit, when appropriate.

The following analysis populations are defined for the study:
  Safety Population: all patients who have received at least 1 dose of study drug, including partial infusions.
  Full Analysis Set (FAS): all patients who have received at least 1 dose of study drug during the Part 1 and who have at least 1 post-baseline efficacy assessment for determination of the MDRI during Part 1 of the study. It is from this pool of patients that response will be examined to determine response during Part 1 and entry into Enriched population.
  Enriched population: Patients who enter the cross-over portion of Part 2 of the study for evaluation of the MDRI. The Enriched population will be the primary population for establishing efficacy.
  PK population: all patients who have received at least 1 dose of study drug and have at least one evaluable blood sample for PK analysis collected.

The focus of the safety analyses will be predicated on the Safety population composed of all consented patients who are enrolled into the study and receive at least 1 dose of the study drug. The safety analysis will be based on AEs, physical examination, ECG, vital signs, and clinical laboratory assessment recorded over the course of the study. Tolerability will be defined with respect to time using two defined treatment patterns: Safety population receiving study drug during the study and the Enriched population that will receive placebo during Part 2. Descriptive statistics will be prepared for all parameters and stratified by disease type, including 2-sided 95% confidence limits.

Example 2: Study to Assess Safety and Efficacy of IV Trehalose Injection Treatment on Functional Outcome in Patients with Sanfilippo Syndrome Type A or Type B Methodology: An 82-week, randomized, double-blind, placebo-controlled trial to assess the safety and efficacy of IV Trehalose Injection 90 mg/mL for the treatment of Sanfilippo syndrome type A and type B is conducted. Patients 3 to 12 years of age with genetically confirmed Sanfilippo syndrome type A or B who are considered to have rapidly progressive disease based on specific mutations or early diagnosis (less than 6 years of age), an AEqs greater than or equal to 24 months on the Vineland-3, and who have elevated excretion of GAGs in the urine and/or elevated levels of HS in plasma and/or urine are eligible for enrollment. Patients will be randomized 1:1 to receive weekly infusions of IV trehalose or placebo. Randomization will be stratified by disease type (A or B).

The study includes a 4-week screening period. During the screening period, urinary GAG, and urinary and plasma HS biomarkers will be collected 3 times, 7 days apart, to establish the baseline excretion and plasma concentration. Patients will have the following baseline assessments: physical exam, safety labs, CSF HS level, and electrocardiogram (ECG). Neurocognitive and behavioral assessments will be performed using the Vineland-3, either the BSID-III or the KABC-II (based on the AEqs on the Vineland-3), and the SBRS. Quality of life will be assessed using the PedsQL™.

Baseline gross and fine motor function will be assessed by a physical therapist and videoed for scoring. The assessments include the 9-hole peg test (9-HIPT), timed up and go (TUG) test, 10-meter walk test, and pre-specified items of the Gross Motor Function Measure (GMFM). An independent physical therapist or other qualified clinician will review video of the patient completing the assessments and score the degree of the patient's change in ability to perform assessments using the CGIC scale.

Dosing and Dose Titration: Following screening, eligible patients will be randomized to receive weekly infusions of either IV trehalose or placebo for the duration of their participation. All patients participating in the study will have their safety data monitored approximately every 3 weeks by the Safety Review Committee (SRC) during the 9-week dose titration period.

During the 9-week dose titration period, patients randomized to IV trehalose will be titrated to 0.75 g/kg of IV trehalose or the MTD. Patients randomized to placebo (normal saline) will receive a weight-based equal volume of placebo. The blinded dose titration will begin on treatment Week 1 with an assigned starting dose of 0.25 g/kg of trehalose or matching placebo administered IV over 60 minutes once weekly. At Week 3 (after the first 2 weekly doses of 0.25 g/kg), patients will have safety labs assessed. The SRC consisting of the sponsor's chief medical officer or designee, the lead principal investigator (PI) (or their designated physician sub-investigator), and an external physician with clinical trial safety data review experience, and a PK expert (unblinded) will be convened. The SRC will review each patient's safety and PK data (as available) within 1 week of the Week 3 dose. If there are no safety concerns identified, the dose will be increased to 0.50 g/kg at Week 4. Although the SRC will make a recommendation, the ultimate decision to escalate the dose, continue the same dose or stop treatment is the responsibility of the local PI at all decision points. At Week 6 (after 2 weekly doses of 0.50 g/kg), patients will have safety labs assessed. The SRC will review each patient's safety data within 1 week of the Week 6 dose. If there are no safety issues identified by the SRC, the dose will be increased to 0.75 g/kg at Week 7. At Week 9 (after 2 weekly doses of 0.75 g/kg for patients assigned to IV trehalose), patients will have safety labs assessed. The SRC will review each patient's safety data within 1 week of the Week 9 dose. If there are no safety issues identified by the SRC, the dose will remain at 0.75 g/kg.

It is expected that patients will reach their MTD by Week 7 and will continue treatment at their MTD to the end of the 78-week treatment period.

Safety and Efficacy: The primary assessment of safety is incidence of serious and non-serious TEAEs.

Efficacy assessments will be performed at Weeks 13, 26, 39, 52, 65, and 78. The primary assessment of efficacy is neurocognitive function evaluated at Week 78. The primary endpoint is a comparison of the mean change from baseline in AEqs on the Vineland 3 (3 domains; Socialization, Daily Living Skills, and Motor Function) between patients treated with IV trehalose vs. placebo at Week 78.

An independent Data Monitoring Committee (DMC) will review safety and PK data at time points to be defined in the DMC Charter. In addition, a futility analysis will be performed when 16 patients have reached Week 52 or have discontinued the trial.

Patients who complete the current trial may be eligible for enrollment in an extension study.

Exemplary criteria for diagnosis and main criteria for inclusion & exclusion are listed below.

Inclusion:
1. Provided written informed consent signed by parent(s) or legal guardian(s)
2. Genetically confirmed Sanfilippo syndrome type A or type B,
   a. Genomic DNA analysis demonstrating a homozygous or compound heterozygous pathogenic variants in the SGSH (type A) or NAGLU (type B) genes
3. Elevated excretion of urinary GAGs and/or urinary or plasma HS at screening (mean of 3 assessments>upper limit of normal [ULN])
4. Male or female; 3 to 12 years of age, inclusive
5. Age-equivalent score (AEq) greater than or equal to 24 months on the Vineland-3 at screening. This will be determined based on the sum of the scores from 4 domains: Communication, Daily Living Skills, Socialization, and Motor Skills.
6. Patients with rapidly progressive Sanfilippo syndrome type A or B as defined by genotype or diagnosis before age 6
7. Negative urine or serum beta-human chorionic gonadotropin (8-hCG) pregnancy result at screening for female patients with child-bearing potential
8. Willingness to comply with sexual abstinence or contraception guidelines as instructed Exclusion:
1. Prior administration of stem cell or gene therapy, or enzyme replacement therapy (ERT) for Sanfilippo syndrome type A or type B
   a. Patients who are at least one-year post ERT therapy at time of consent may be enrolled with documented evidence of a ≥3 month decline in AEqs according to Vineland, BSID, or KABC assessment within the last 12 months
2. Previously diagnosed with diabetes or a hemoglobin A1c (HgbA1c) result>6.0% at screening
3. Poorly controlled seizures, defined as one or more seizure per week for the last 4 6 weeks
4. Visual or hearing impairment sufficient to preclude cooperation with neurodevelopmental testing
5. Any other medical condition that, in the opinion of the investigator, would confound interpretation of safety or efficacy data or would place a patient at undue risk
6. Inability to cooperate with protocol-required assessments or procedures
7. Prior treatment with IV trehalose
8. Known hypersensitivity to trehalose
9. Use of genistein-rich soy isoflavone within 30 days before signing of consent
10. Use of oral trehalose within 7 days before signing of consent
11. Evidence of hepatitis B or hepatitis C infection upon serological testing at screening
12. Currently receiving anti-coagulant treatment (e.g., warfarin, enoxaparin), other than anti-platelet treatments, which are not a reason for exclusion
13. Currently participating in another clinical trial or has completed an interventional trial less than 90 days prior to planned first dosing Investigational product, dosage and mode of administration: Trehalose 90 mg/mL solution will be administered IV over 60±5 minutes once weekly. Trehalose will be administered in a dose titration manner as described above (Week 1 through Week 9) starting with a dose of 0.25 g/kg and up to a maximum dose of 0.75 g/kg. Indwelling catheters are not permitted.

Reference therapy, dosage and mode of administration: Placebo (sodium chloride injection, 0.9%, USP) will be administered IV over 60±5 minutes once weekly. Placebo will be administered in a dose titration manner as described above (Week 1 through Week 9) starting with a weight-based volume equivalent to 0.25 g/kg and up to a maximum weight-based volume equivalent to 0.75 g/kg. Indwelling catheters are not permitted.

Restricted Medications: There are no known drug-drug interactions with IV trehalose 90 mg/mL. If the patient starts the study on miglustat, the dose must remain the same throughout the study. Patients are not permitted to initiate treatment with miglustat while on study. Cannabidiol (CBD) oil is permitted but the dose must remain the same throughout the study. Behavioral medications (stimulants, non-stimulants, psychotropic medications) are permitted if the patient is taking them at the time of consent. The dose and frequency should remain the same throughout the study if at all possible. Oral trehalose and genistein-rich soy isoflavones are not permitted during the study. Patients should not change concomitant medications during the study unless they experience an exacerbation of epilepsy or an acute illness. Patients may receive concomitant medications that are medically necessary as standard care to treat symptoms such as AEs, inter-current illnesses, anxiety and to prevent illness, e.g. vaccines. Over-the-counter (OTC) medications such as vitamins or herbal supplements are permitted if the patient is taking them at the time of consent. The dose and frequency should remain the same throughout the study if at all possible.

Statistical Methods:

Analysis Populations: The following analysis populations will be used for all statistical analyses and presentations:

The full analysis set (FAS) includes all randomized patients who receive any study medication.

The per protocol set (PPS) includes all patients in the FAS, except those who are excluded because of major protocol violations, where a major protocol violation is one that may affect the interpretation of the study results (violating an inclusion criteria, receiving less than a specified amount of study medication during the course of the study, unavailability of the primary assessment).

The safety set (SAF) includes all patients who receive any study medication.

The PK analysis set (PKS) includes all patients in the SAF for whom a sufficient number of plasma trehalose concentrations are available to allow for PK analysis. Patients who are excluded from the PK analysis will be listed in the PK report along with the reason for exclusion.

The FAS will be used for all hypothesis tests of efficacy. The PPS will be used for supportive or sensitivity efficacy analyses. The SAF will be used for all safety analyses.

Sample Size Considerations:

The sample size is primarily based on feasibility; however, it is estimated that 16 patients (8 per treatment group) will have 80% power to detect a difference between treatment groups of at least 4.4 months in the AEqs, using a 2-sided, alpha of 0.05, and assuming a standard deviation of the change from baseline in the AEqs of 2.9 months.

Statistical methods: A detailed description of the planned data analysis for the study will be documented in the Statistical Analysis Plan (SAP). All statistical tests will be 2-sided and use an overall study-wise alpha of 0.05, unless otherwise stated in the SAP. Analysis of efficacy data will be analyzed and the results presented by randomized treatment assignment. Safety data will be summarized by actual treatment received.

The primary efficacy analysis will use a main-effects, mixed-model for repeated measures (MMRM) for the primary endpoint of change from baseline in the AEqs at Week 78. The model will include treatment, disease type, visit (categorical), treatment-by-visit interaction as fixed effects, baseline AEqs as covariate and patient as a random effect. Supportive modelling will include a MMIRM main-effects model with treatment, disease type, time and patient. Model assumptions will be evaluated and if parametric assumptions are inappropriate, analysis based on ranks will be conducted. Supportive sensitivity analyses will include a multiple imputations approach for missing values in a main-effects analysis of covariance (ANCOVA) with baseline AEqs as the covariate on the change from baseline AEqs at Week 78. The same statistical methodology will be applied to analysis of the secondary continuous endpoints. The secondary analysis based on time to progression of 3 months in the AEqs will be a presentation of Kaplan-Meyer curves and inferential treatment comparison by the log rank test. The secondary analysis of the proportion of patients progressing by Week 78 will be by Fisher's exact test and the Cochran-Mantel-Haenszel test.

Multiplicity of the secondary efficacy endpoints will employ a conditional sequence approach to control alpha. The primary analysis of the primary endpoint will be tested first, and conditional on statistical significance will proceed to the secondary endpoints. Details for the control of type I error in analysis of the secondary endpoints will be described in the SAP.

Observed values and changes from baseline for continuous endpoints will be summarized descriptively by treatment group and visit using mean, median, quartiles, and standard deviation. Binary endpoints will be summarized using frequencies and percentages by treatment group and visit.

Independent Data Monitoring Committee and Interim Analysis: An external, independent Data Monitoring Committee (DMC) will review safety and PK data at time points defined in the DMC Charter. In addition, the DMC will review the results of an Interim Analysis (IA) of efficacy data.

An unblinded IA for efficacy futility will be conducted when 16 patients have completed their Week 52 visit or have discontinued from the trial. The IA will consist of an analysis of (1) the mean change from baseline in the AEqs and (2) the time-to-progression of 3 months in the AEqs. The results of the analysis will be presented to the DMC, who will make a recommendation on whether the study should continue as planned or stop for efficacy futility. There is no plan to stop the study for efficacy success nor to provide early unblinded results to the sponsor or others involved in conducting the study. Further details of the statistical methodology for the IA, including suggested stopping boundaries, will be included in the DMC Charter and Interim Analysis Plan (IAP).

Example 3: Study to Assess Safety and Efficacy of Intravenous Trehalose Injection Treatment on Functional Outcome in Patients with Sanfilippo Syndrome Methodology: A 78-week, open-label, single-arm study to assess the safety and efficacy of IV Trehalose Injection 90 mg/mL for the treatment of Sanfilippo syndrome is conducted. Patients 3 to 25 years of age with genetically confirmed Sanfilippo syndrome (any type) who have an AEqs≥12 months on the Vineland 3 are eligible for enrollment. Any patient 3 to 12 years of age, inclusive, with a confirmed diagnosis of Sanfilippo type A or B who has an AEqs of ≥24 months on the Vineland-3 must be considered for enrollment in the study described in above Examples first. If such a patient is a screen failure for the study described in above Examples, they may be considered for enrollment in this study. In addition, patients who have completed the study described in above Examples are eligible for enrollment in the current study irrespective of AEqs at completion of the study described in above Examples.

The study includes up to a 6-week screening period for de novo patients. During the screening period, urinary GAG, and urinary and plasma HS biomarkers will be collected 3 times, 7 days apart, to establish the baseline excretion and plasma concentration. Patients will have the following baseline assessments: physical exam, safety labs, and electrocardiogram (ECG). Neurocognitive and behavioral assessments will be performed using the Vineland 3 and the SBRS. Quality of life will be assessed using the PedsQL™, CaGIS and CaGIC. Baseline gross motor function will be assessed using the 10-meter walk test. Patients who screen fail may be rescreened once.

Patients who participated in the study described in above Examples will continue to be administered the BSID-II or KABC II in this study. Their last assessment (e.g., laboratory analyses, screening labs, Vineland-3, BSID-III and/or KABC-II scores, 10-meter walk test, CaGIS and CaGIC) will serve as their baseline data for the current study; therefore, there is no screening period for these patients in the current study. Patients who participated in the study described in above Examples must be enrolled in the current study within 3 weeks of completion of the study described in above Examples.

Dosing and Dose Titration: Following screening, eligible patients will receive weekly infusions of IV trehalose for the duration of their participation. All patients participating in the study will have their safety data monitored approximately every 3 weeks by the Safety Review Committee (SRC) during the 12-week dose titration period.

During the 12-week dose titration period, all patients will be titrated to 0.75 g/kg of IV trehalose or the MTD, including patients who completed the study described in above Examples (to maintain study blinding). Dose titration will begin on treatment Week 1 with a starting dose of 0.25 g/kg of trehalose administered IV over 60 minutes. At Week 4 (after the first 3 weekly doses of 0.25 g/kg), patients will have PK samples drawn with that infusion and safety labs assessed. The SRC consisting of the sponsor's chief medical officer or designee, the site principal investigator (PI) (or their designated physician sub-investigator), and an external physician with clinical study safety data review experience, and a PK expert will be convened. The SRC will review each patient's safety and PK data within 1 week of the Week 4 dose. If there are no safety concerns identified, the dose will be increased to 0.50 g/kg at Week 5. Although the SRC will make a recommendation, the ultimate decision to escalate the dose, continue the same dose or stop treatment is the responsibility of the local PI at all decision points. At Week 8 (after 3 weekly doses of 0.50 g/kg), patients will have PK samples drawn and safety labs assessed. The SRC will review each patient's safety data within 1 week of the Week 8 dose. If there are no safety issues identified by the SRC, the dose will be increased to 0.75 g/kg at Week 9. At Week 12 (after 3 weekly doses of 0.75 g/kg for patients assigned to IV trehalose), patients will have PK samples drawn and safety labs assessed. The SRC will review each patient's safety data within 1 week of the Week 12 dose. If there are no safety issues identified by the SRC, the dose will remain at 0.75 g/kg.

It is expected that patients will reach their MTD by Week 12 and will continue treatment at their MTD to the end of the 72-week treatment period.

Safety and Efficacy: The primary safety endpoint is incidence of serious and non-serious TEAEs.

Efficacy assessments will be performed at Weeks 12, 24, 48, and 72. The primary efficacy endpoint is the change from baseline in the ABC score at Week 72 on the Vineland 3. The ABC is calculated from the standard scores of the Communication, Daily Living Skills, and Socialization domains.

Exemplary criteria for diagnosis and main criteria for inclusion & exclusion are listed below.

Inclusion:
1. Provided written informed consent signed by parent(s) or legal guardian(s).
2. Genetically confirmed Sanfilippo syndrome type A, B, C, or D.
   a. Genomic DNA analysis demonstrating a homozygous or compound heterozygous pathogenic variants.
3. Patients with a score≥24 months on the Vineland-3 must have either completed the study described in the above Examples or failed to meet other screening criteria for the study described in the above Examples.
4. Male or female; 3 to 25 years of age, inclusive.
5. Have an AEqs that meets either:
   a. ≥12 months on the Vineland-3 AEqs at screening. This will be determined based on the mean of the AEqs from the 3 sub-domains: Communication, Daily Living Skills, and Socialization
   b. Any AEqs provided the patient has completed the study described in the above Examples.
6. Negative urine or serum beta-human chorionic gonadotropin (8-hCG) pregnancy result at screening for female patients with child-bearing potential.
7. Parent or legally authorized representative oversees and provides either assurance of sexual abstinence or acceptance of contraception guidelines as instructed.

Exclusion:
1. Prior administration of stem cell or gene therapy, or enzyme replacement therapy (ERT) for Sanfilippo syndrome type A, B, C, or D.
   a. Patients who are at least one-year post ERT therapy at time of consent may be enrolled provided there is no evidence of clinical benefit.
2. Previously diagnosed with diabetes or a hemoglobin A1c (HgbA1c) result>6.0% at screening.
3. Poorly controlled seizures, defined as one or more seizure per week for the last 4 6 weeks.
4. Visual or hearing impairment sufficient to preclude cooperation with neurodevelopmental testing.
5. Any other medical condition that, in the opinion of the investigator, would confound interpretation of safety or efficacy data or would place a patient at undue risk.
6. Inability to cooperate with protocol-required assessments or procedures.
7. Prior treatment with IV trehalose except for patients previously enrolled in the study described in the above Examples, where treatment assignment in the study described in the above Examples will not be revealed at the time of enrollment in the current study.
8. Known hypersensitivity to trehalose.
9. Use of genistein-rich soy isoflavone within 30 days before signing of consent.
10. Use of oral trehalose within 7 days before signing of consent.
11. Evidence of hepatitis B or hepatitis C infection upon serological testing at screening.
12. Currently participating in another clinical trial or has completed an interventional trial less than 90 days prior to planned first dose in the current study excepting patients who completed the study described in the above Examples and enrolled in the current study within 3 weeks of completion of the study described in the above Examples.

Investigational product, dosage, and mode of administration: Trehalose 90 mg/mL solution will be administered IV over 60±5 minutes once weekly. Trehalose will be administered in a dose titration manner as described above (Week 1 through Week 12) starting with a dose of 0.25 g/kg and up to a maximum dose of 0.75 g/kg. Indwelling catheters are not permitted.

Restricted Medications: There are no known drug-drug interactions with IV trehalose 90 mg/mL. If the patient starts the study on miglustat, the dose must remain the same throughout the study. Patients are not permitted to initiate treatment with miglustat while on study. Cannabidiol (CBD) oil is permitted but the dose must remain the same throughout the study. Behavioral medications (stimulants, non-stimulants, psychotropic medications) are permitted if the patient is taking them at the time of consent. The dose and frequency should remain the same throughout the study if at all possible. Oral trehalose and genistein-rich soy isoflavones are not permitted during the study. Patients should not change concomitant medications during the study unless they experience an exacerbation of epilepsy or an acute illness. Patients may receive concomitant medications that are medically necessary as standard care to treat symptoms such as adverse events (AEs), inter-current illnesses, anxiety and to prevent illness, e.g. vaccines. Over-the-counter (OTC) medications such as vitamins or herbal supplements are permitted if the patient is taking them at the time of consent. The dose and frequency should remain the same throughout the study if at all possible.

Statistical Methods:

Analysis populations: The following analysis populations will be used for all analyses and presentations:

The full analysis set (FAS) and the safety set (SAF) are the same and include all patients who receive any study medication during the study.

The PK analysis set (PKS) includes all patients in the FAS/SAF for whom a sufficient number of plasma trehalose concentrations are available to allow for PK analysis. Patients who are excluded from the PK analysis will be listed in the PK report along with the reason for exclusion.

Sample size considerations: The sample size for this open-label, single-arm study is based on feasibility. All patients who completed the study described in the above Examples will be allowed to enroll as well as direct de novo enrollees, for a maximum of 24 total patients.

Statistical methods: A detailed description of the planned data analysis for the study will be documented in the Statistical Analysis Plan (SAP).

Observed values and changes from baseline for continuous efficacy and pharmacodynamic endpoints will be summarized descriptively by study visit using mean, median, quartiles, minimum, maximum, standard deviation, standard error, and 95% confidence intervals. Binary endpoints will be summarized using frequencies and percentages by visit. Descriptive statistics will be presented for the following subgroups defined by their entry category:

Patients who completed the study described in the above Examples, who received double-blind trehalose during that study Patients who completed the study described in the above Examples, who received double-blind placebo during that study De novo patients who had not previously enrolled in the study described in the above Examples.

Safety data will be summarized by study visit for the entire population, as well as by the above subgroups.

Example 4: Safety and Efficacy Study of Intravenous Trehalose Injection on Functional Out Come and Biomarkers in Patients with Sanfilippo Syndrome Type A or Type B Methodology: A 57-week, open label trial to assess the safety and efficacy of IV Trehalose Injection 90 mg/mL for the treatment of Sanfilippo syndrome type A and type B is conducted.

Patients 3 to 16 years of age with genetically confirmed Sanfilippo syndrome type A or B who are considered to have rapidly progressive disease based on specific mutations or early diagnosis (less than 6 years of age), and who have elevated excretion of GAGs in the urine and/or elevated levels of HS in plasma and/or urine are eligible for enrollment. Patients will receive weekly infusions of IV trehalose.

The safety population will consist of all patients who receive at least one infusion or partial infusion of trehalose. The primary efficacy population will consist of the subgroup of patients in the safety population who are age 3 through 7 at time of consent (Cohort 1).

The study includes a 4-week screening period. During the screening period, urinary GAG, and urinary and plasma HS biomarkers will be collected 3 times, 7 days apart, to establish the baseline excretion and plasma concentration. Patients will have the following baseline assessments: physical exam, safety labs, and electrocardiogram (ECG).

Neurocognitive and behavioral assessments will be performed using the Vineland-3, the BSID-III and the SBRS. Sleep will be assessed using the Promis® Parent Proxy Sleep Disturbance Short Form 8A. A Rater Training Plan will outline the educational and experience requirements for site raters, as well as the process for training and certification.

Dosing and Dose Titration: Following screening, eligible patients will receive weekly infusions of IV trehalose for 52 weeks. An end of study assessment will be performed at week 53, 1 week after the final infusion.

The first 9 weeks are a dose titration period. The dose of trehalose will be titrated up from 0.25 g/kg to 0.75 g/kg or the maximum tolerated dose (MTD). The dose titration will begin on treatment Week 1 with the starting dose of 0.25 g/kg administered IV over 60 minutes once weekly. At Week 3 (after the first 2 weekly doses of 0.25 g/kg), patients will have safety labs assessed. The Safety Review Committee (SRC) consisting of the sponsor's chief medical officer or designee, the principal investigator (PI) (or their designated physician subinvestigator), and an external physician with clinical trial safety data review experience, and a PK expert will be convened. The SRC will review each patient's safety and PK data (as available) within 1 week of the Week 3 dose. If there are no safety concerns identified, the dose will be increased to 0.50 g/kg at Week 4. Although the SRC will make a recommendation, the ultimate decision to escalate the dose, continue the same dose or stop treatment is the responsibility of the local PI at all decision points. At Week 6 (after 2 weekly doses of 0.50 g/kg), patients will have safety labs assessed. The SRC will review each patient's safety data within 1 week of the Week 6 dose. If there are no safety issues identified by the SRC, the dose will be increased to 0.75 g/kg at Week 7. At Week 9 (after 2 weekly doses of 0.75 g/kg for patients assigned to IV trehalose), patients will have safety labs assessed. The SRC will review each patient's safety data within 1 week of the Week 9 dose. If there are no safety issues identified by the SRC, the dose will remain at 0.75 g/kg. It is expected that patients will reach their MTD by Week 7 and will continue treatment at their MTD to the end of the 52-week treatment period. End of study assessments will be performed 1 week after the final infusion (Week 53).

Safety and Efficacy: The primary assessment of safety is incidence of serious and non-serious TEAEs, physical examination findings, vital signs, and clinical laboratory tests. The study will enroll patients from 3 to 16 years of age divided into 2 cohorts, 3 to 7 years of age (Cohort 1) and 8 to 16 years of age (Cohort 2) inclusive. Efficacy will be assessed using the Vineland-3, BSID-III and SBRS. Efficacy assessments will be performed at Weeks 13, 26, 39, and 52 in all patients. However due to the rapidly progressive nature of this disease, the primary assessment of efficacy will be restricted to the 3 to 7 year age cohort. Based on the two natural history studies in Sanfilippo Type A and Type B patients, (Shapiro et. al 2016 and Whitely et. al 2018) 69% of patients between the ages of 3 to 7 are expected to decline>3 months on the Vineland-3 in a 12-month period. Therefore, the primary assessment of efficacy is neurocognitive function evaluated on the Vineland-3 (3 domains; Socialization, Daily Living Skills, and Motor Function). The primary endpoint is a comparison of the percent of patients with >3 month decline on the Vineland-3 over a period of 52 weeks compared to the natural history data. Additional secondary efficacy endpoints include the change from baseline in the AEqs of the Vineland-3 at various time points and change in biomarkers. Exploratory endpoints include assessment of the change from baseline in the BSID-III and the SBRS. In addition, efficacy will be explored in the 8 to 16-year-old cohort using descriptive statistics for change from baseline in each of the scales.

Biomarker levels measured in plasma and urine will be monitored at Weeks 3, 6, 9, 13, 26, 39, and 52.

Since patients with Sanfilippo experience significant sleep disturbances, the Promis® Parent Proxy Sleep Disturbance Short Form 8A will be used to determine the effect of treatment on sleep patterns at Week 13, 26, 39, and 52.

In addition to the SRC, an independent Data Monitoring Committee (DMC) will review safety data at time points to be defined in the DMC Charters (at least at weeks 13, 26, and 39). Patients who complete the current trial may be eligible for enrollment in an extension study.

Sample Size Justification: Up to 20 patients with Sanfilippo Type A or Type B will be enrolled. The sample size is not based on statistical considerations due to the orphan nature of the disease. However at least 10 patients between the ages of 3 years and 7 years need to be enrolled for the primary assessment of efficacy.

Exemplary criteria for diagnosis and main criteria for inclusion & exclusion are listed below.

Inclusion:
1. Provided written informed consent signed by parent(s) or legal guardian(s)
2. Genetically confirmed Sanfilippo syndrome type A or type B
   a. Genomic DNA analysis demonstrating a homozygous or compound heterozygous pathogenic variants in the SGSH (type A) or NAGLU (type B) genes
3. Elevated excretion of urinary GAGs and/or urinary or plasma HS at screening (mean of 3 assessments>upper limit of normal [ULN])
4. Male or female; 3 to 16 years of age, inclusive
5. Patients with rapidly progressive Sanfilippo syndrome type A or B as defined by genotype or diagnosis before age 6
6. Negative urine or serum beta-human chorionic gonadotropin (β-hCG) pregnancy result at screening for female patients with child-bearing potential
7. Willingness to comply with sexual abstinence or contraception guidelines outlined in the protocol Exclusion:
1. Prior administration of stem cell or gene therapy, or enzyme replacement therapy (ERT) for Sanfilippo syndrome type A or type B
   a. Patients who are at least one-year post ERT therapy at time of consent may be enrolled with no demonstrable effect of treatment.
2. Previously diagnosed with diabetes or a hemoglobin A1c (HgbA1c) result>6.0% at screening
3. Poorly controlled seizures, defined as one or more seizure per week for the last 4-6 weeks
4. Visual or hearing impairment sufficient to preclude cooperation with neurodevelopmental testing
5. Any other medical condition that, in the opinion of the investigator, would confound interpretation of safety or efficacy data or would place a patient at undue risk
6. Inability to cooperate with protocol-required assessments or procedures
7. Prior treatment with IV trehalose
8. Known hypersensitivity to trehalose
9. Use of genistein-rich soy isoflavone within 30 days before signing of consent
10. Use of oral trehalose within 7 days before signing of consent
11. Evidence of hepatitis B or hepatitis C infection upon serological testing at screening
12. Currently receiving anti-coagulant treatment (e.g., warfarin, enoxaparin), other than anti-platelet treatments, which are not a reason for exclusion
13. Currently participating in another clinical trial or has completed an interventional trial less than 90 days prior to planned first dosing Investigational product, dosage and mode of administration: Trehalose 90 mg/mL solution will be administered IV over 60±5 minutes once weekly.

Trehalose will be administered in a dose titration manner as described above (Week 1 through Week 9) starting with a dose of 0.25 g/kg and up to a maximum dose of 0.75 g/kg. Indwelling catheters are not permitted.

Duration of treatment: The study includes a 4-week screening period and 52-week treatment period which includes the 9 week dose titration period.

Restricted Medications: There are no known drug-drug interactions with IV trehalose 90 mg/mL. If the patient starts the study on miglustat, the dose must remain the same throughout the study. Patients are not permitted to initiate treatment with miglustat while on study. Cannabidiol (CBD) oil is permitted but the dose must remain the same throughout the study. Behavioral medications (stimulants, non-stimulants, psychotropic medications) are permitted if the patient is taking them at the time of consent. The dose and frequency should remain the same throughout the study if at all possible. Oral trehalose and genistein-rich soy isoflavones are not permitted during the study. Patients should not change concomitant medications during the study unless they experience an exacerbation of epilepsy or an acute illness. Patients may receive concomitant medications that are medically necessary as standard care to treat symptoms such as AEs, inter-current illnesses, anxiety and to prevent illness, e.g. vaccines. Over-the-counter (OTC) medications such as vitamins or herbal supplements are permitted if the patient is taking them at the time of consent. The dose and frequency should remain the same throughout the study if at all possible.

Statistical methods: The safety population will consist of all patients who receive at least one infusion or partial infusion of trehalose. The primary efficacy population will consist of the subgroup of patients in the safety population who are age 3 through 7 at signing of consent (Cohort 1).

Safety analyses will include descriptive summaries of the incidence and severity of treatment-emergent adverse events, incidence of serious adverse events, physical examination findings, vital signs, and clinical laboratory tests. AEs and SAEs will be tabulated by system organ class, preferred term, severity and relationship to drug.

The primary efficacy endpoint is the proportion of patients (aged 3-7 at signing of consent) with at least a 3 month decline in the Vineland-3 Age Equivalent Score (AEqs) at Week 52. This will be compared to an historical control group, (16 patients) which will be obtained from longitudinal natural history studies (noted above) during which patients were treated with standard of care. The primary analysis will be a comparison between groups using the Cochran-Mantel-Haenszel, Chi-square test with disease type (A or B) as a stratification variable. The Fisher's exact test will be used if there is an inadequate number of patients in any treatment/stratum cell.

The planned sample size is primarily based on feasibility; however, it is estimated that 10 patients in the treated group and 16 patients in the historical control group will have approximately 80% power to detect as significant (2-sided, $\alpha=0.05$) true rates of decline (at least 3 points in the AEqs at Week 52) of 0.09 and 0.69, respectively. With an increase in sample size to 16 in the treated group, the proportion estimated to provide 80% power increases to 0.16. This assumes that the treated and historical control groups are effectively sampled from equivalent patient populations with comparable, if untreated, rates of decline in the Vineland-3 AEqs. The least significant decline rate in the treated group, under the above assumptions, is estimated to be 0.21 and 0.28 for sample sizes of 10 and 16, respectively.

A secondary analysis will be conducted for the difference between the treated group and the historical control group for mean change from baseline in the AEqs. This will use a mixed-effects model for repeated measures (MMRM) including treatment, disease type (A or B), visit (categorical), and treatment-by-visit interaction as fixed effects, baseline AEqs as covariate, and patient as a random effect. An additional supportive model will assess the treatment effect on the slope of the AEqs change using an MMRM with treatment, disease type, time (continuous), and baseline AEqs.

Analysis of the secondary and exploratory endpoints will be presented descriptively and analyzed with the same statistical models described above.

Given the small sample size of the study, the occurrence of dropouts and missing values may potentially have a large impact on the efficacy inferences and estimates. It will, therefore, be important to obtain the Week 52 Vineland-3 assessment for all treated patients. Every effort will be made to bring patients who have discontinued back to the clinic for their Week 52 safety and efficacy assessments. These assessments will be used in the primary efficacy analysis. For patients who have discontinued and for whom the Week 52 Vineland-3 assessment remains missing, the AEqs will be imputed as having declined by 3 months for the primary analysis. Additional sensitivity analyses will be conducted of the impact of missing data on the conclusions from the primary and secondary analysis of change in Vineland-3 AEqs. The methods for these will be described in the SAP.

What is claimed is:

1. A method of treating a mucopolysaccharidosis in a subject in need thereof, comprising administering intravenously to the subject an aqueous pharmaceutical formulation comprising a single active ingredient consisting essentially of substantially purified trehalose, wherein:
the pH of the formulation is about 4.5 to 7.0;
the formulation contains less than about 0.75 endotoxin units per mL;
the formulation has an osmolality of about 280 mOsm/kg to 330 mOsm/kg;
the formulation is administered over about 15 minutes to about 150 minutes;
wherein the substantially purified trehalose is present in the formulation in an amount of about 5% (w/v) to about 15% (w/v); and
wherein the substantially purified trehalose contains less than about 0.5% contaminants.

2. A method of treating a mucopolysaccharidosis in a subject in need thereof, comprising administering intravenously to the subject an aqueous pharmaceutical formulation comprising substantially purified trehalose and a trehalase inhibitor as the sole active ingredients, wherein:
the pH of the formulation is about 4.5 to 7.0;
the formulation contains less than about 0.75 endotoxin units per mL;
the formulation has an osmolality of about 280 mOsm/kg to 330 mOsm/kg;
the formulation is administered over about 15 minutes to about 150 minutes;
wherein the substantially purified trehalose is present in the formulation in an amount of about 5% (w/v) to about 15% (w/v); and
wherein the substantially purified trehalose contains less than about 0.5% contaminants.

3. A method of treating a mucopolysaccharidosis in a subject in need thereof, comprising
(a) determining that the subject has a lysosomal enzyme deficiency; and
(b) administering intravenously an aqueous pharmaceutical formulation to the subject, wherein the formulation comprises a single active ingredient consisting essentially of substantially purified trehalose, wherein:
the pH of the formulation is about 4.5 to 7.0;
the formulation contains less than about 0.75 endotoxin units per mL;
the formulation has an osmolality of about 280 mOsm/kg to 330 mOsm/kg;
the formulation is administered intravenously over about 15 minutes to about 150 minutes;
wherein the substantially purified trehalose is present in the formulation in an amount of about 5% (w/v) to about 15% (w/v); and
wherein the substantially purified trehalose contains less than about 0.5% contaminants.

4. The method of claim 1, wherein the mucopolysaccharidosis is selected from the group consisting of: Hurler syndrome (MPS IH), Hurler-Scheie syndrome (MPS IH/S), Scheie syndrome (MPS IS or MPS V), Hunter syndrome (MPS II), Sanfilippo syndrome A (MPS IIIA), Sanfilippo syndrome B (MPS IIIB), Sanfilippo syndrome C (MPS IIIC), Sanfilippo syndrome D (MPS IIID), Morquio syndrome A (MPS IVA), Morquio syndrome B (MPS IVB), Maroteaux-Lamy syndrome (MPS VI), Sly syndrome (MPS VII), and Natowicz syndrome (MPS IX).

5. The method of claim 4, wherein the mucopolysaccharidosis is Hurler syndrome (MPS IH).

6. The method of claim 4, wherein the mucopolysaccharidosis is Scheie syndrome (MPS IS or MPS V).

7. The method of claim 4, wherein the mucopolysaccharidosis is Hunter syndrome (MPS II).

8. The method of claim 4, wherein the mucopolysaccharidosis is Sanfilippo syndrome A (MPS IIIA).

9. The method of claim 4, wherein the mucopolysaccharidosis is Sanfilippo syndrome B (MPS IIIB).

10. The method of claim 4, wherein the mucopolysaccharidosis is Sanfilippo syndrome C (MPS IIIC).

11. The method of claim 4, wherein the mucopolysaccharidosis is Sanfilippo syndrome D (MPS IIID).

12. The method of claim 4, wherein the mucopolysaccharidosis is Morquio syndrome A (MPS IVA).

13. The method of claim 4, wherein the mucopolysaccharidosis is Morquio syndrome B (MPS IVB).

14. The method of claim 4, wherein the mucopolysaccharidosis is Maroteaux-Lamy syndrome (MPS VI).

15. The method of claim 4, wherein the mucopolysaccharidosis is Sly syndrome (MPS VII).

16. The method of claim 4, wherein the mucopolysaccharidosis is and Natowicz syndrome (MPS IX).

17. The method of claim 1, wherein the formulation comprises about 8% (w/v) to about 10% (w/v) substantially purified trehalose.

18. The method of claim 1, wherein the formulation comprises about 9% (w/v) substantially purified trehalose.

19. The method of claim 2, wherein the mucopolysaccharidosis is selected from the group consisting of: Hurler syndrome (MPS IH), Hurler-Scheie syndrome (MPS IH/S), Scheie syndrome (MPS IS or MPS V), Hunter syndrome (MPS II), Sanfilippo syndrome A (MPS IIIA), Sanfilippo syndrome B (MPS IIIB), Sanfilippo syndrome C (MPS IIIC), Sanfilippo syndrome D (MPS IIID), Morquio syndrome A (MPS IVA), Morquio syndrome B (MPS IVB), Maroteaux-Lamy syndrome (MPS VI), Sly syndrome (MPS VII), and Natowicz syndrome (MPS IX).

20. The method of claim 3, wherein the mucopolysaccharidosis is selected from the group consisting of: Hurler syndrome (MPS IH), Hurler-Scheie syndrome (MPS IH/S), Scheie syndrome (MPS IS or MPS V), Hunter syndrome (MPS II), Sanfilippo syndrome A (MPS IIIA), Sanfillippo syndrome B (MPS IIIB), Sanfillippo syndrome C (MPS IIIC), Sanfillippo syndrome D (MPS IIID), Morquio syndrome A (MPS IVA), Morquio syndrome B (MPS IVB), Maroteaux-Lamy syndrome (MPS VI), Sly syndrome (MPS VII), and Natowicz syndrome (MPS IX).

\* \* \* \* \*